United States Patent [19]
Alderete

[11] Patent Number: 5,922,563
[45] Date of Patent: Jul. 13, 1999

[54] ADHESIN GENES AND PROTEINS INVOLVED IN *TRICHOMONAS VAGINALIS* CYTOADHERENCE

[75] Inventor: John F. Alderete, San Antonio, Tex.

[73] Assignee: Board of Regents, The University of Texas System, Austin, Tex.

[21] Appl. No.: 08/504,459

[22] Filed: Jul. 20, 1995

[51] Int. Cl.$^6$ .................................................. C12N 15/00
[52] U.S. Cl. .................. 435/69.1; 435/320.1; 435/252.3; 435/254.11; 435/254.2; 536/23.1; 536/23.7; 536/24.3
[58] Field of Search .............................. 435/69.1, 320.1, 435/240.2, 252.3, 254.11, 240.4, 254.2; 536/23.1, 23.7, 24.3

[56] References Cited

U.S. PATENT DOCUMENTS

| | | | |
|---|---|---|---|
| 5,342,782 | 8/1994 | Thach | 435/320.1 |
| 5,580,752 | 12/1996 | Thach | 435/69.1 |

OTHER PUBLICATIONS

Alderete et al., "Iron Mediates *Trichomonas vaginalis* Resistance to Complement Lysis", *Microbial Pathogenesis*, 19:93–103, 1995.
Alderete et al., "Cloning and Molecular Characterization of Two Genes Encoding Adhesion Proteins Involved in *Trichomonas vaginalis* Cytoadherence", *Molecular Microbiology*, 17(1):69–83, 1995.
Alderete et al., "Vaginal Antibody of Patients With Trichomoniasis Is to a Prominent Surface Immunogen of *Trichomonas vaginalis*", *Genitourin Med.*, 67:220–225, 1991.
Alderete et al., "Phenotypes and Protein–Epitope Phenotypic Variation Among Fresh Isolates of *Trichomonas vaginalis*", *Infection and Immunity*, 55(5):1037–1041, May 1987.
Alderete et al., "Specific Parasitism of Purified Vagina Epithelial Cells by *Trichomonas vaginalis*", *Infection and Immunity*, 56(10):2258–2562, Oct. 1988.
Alderete and Garza, "Identification and Properties of *Trichomonas vaginalis* Proteins Involved in Cytadherence", *Infection and Immunity*, 56(1):28–33, Jan. 1988.
Alderete et al., "Monoclonal Antibody to a Major Surface Glycoprotein Immunogen Differentiates Isolates and Subpopulations of *Trichomonas vaginalis*", *Infection and Immunity*, 52(1):70–75, Apr. 1986.
Alderete et al., "Phenotypic Variation and Diversity Among *Trichomonas vaginalis* Isolates and Correlation of Phenotype with Trichomonal Virulence Determinants", *Infection and Immunity*, 53(2):285–293, Aug. 1986.
Alderete and Garza, "Specific Nature of *Trichomonas vaginalis* Parasitism of Host Cell Surfaces", *Infection and Immunity*, 50(3):701–708, Dec. 1985.
Arroyo et al., "Signalling of *Trichomonas vaginalis* for Amoeboid Transformation and Adhesin Synthesis Follows Cytoadherence", *Molecular Microbiology*, 7(2):299–309, 1993.
Arroyo et al., "Molecular Basis of Host Epithelial Cell Recognition by *Trichomonas vaginalis*", *Molecular Microbiology*, 6(7):853–862, 1992.
Arroyo and Alderete, "*Trichomonas vaginalis* Surface Proteinase Activity is Necessary for Parasite Adherence to Epithelial Cells", *Infection and Immunity*, 57(10):2991–2997, Oct. 1989.
Buttle et al., "Selective Cleavage of Glycyl Bonds by Papaya Proteinase IV", *FEBS*, 260(2):195–197, Jan. 1990.
Camara et al., "A Neuraminidase From *Streptococcus pneumoniae* Has the Features of a Surface Protein", *Infection and Immunity*, 62(9):3688–3695, Sep. 1994.
Chomczynski and Sacchi, "Single–Step Method of RNA Isolation by Acid Guanidinium Thiocyanate–Phenol–Chloroform Extraction", *Analytical Biochemistry*, 162:156–159, 1987.
Dailey and Alderete, "The Phenotypically Variable Surface Protein of *Trichomonas vaginalis* Has a Single, Tandemly Repeated Immunodominant Epitope", *Infection and Immunity*, 59(6):2083–2088, Jun. 1991.
Damian, "Molecular Mimicry: Parasite Evasion and Host Defense", *Current Topics in Microbiology and Immunology*, 145:101–115, 1989.
Diamond, "The Establishment of Various Trichomonads of Animals and Man in Axenic Cultures", *Journal of Parasitol*, 43:488–490, 1957.
Eisenberg et al., "Analysis of Membrane and Surface Protein Sequences With the Hydrophobic Moment Plot", *Journal of Molecular Biology*, 179:125–142, 1984.
Goudot–Crozel et al., "The Major Parasite Surface Antigen Associated With Human Resistance to Schistosomiasis Is A 37–KD Glyceraldehyde–3P–Dehydrogenase", *J. Exp. Med.*, 170:2065–2080, Dec. 1989.
Hrdý and Müller, "Primary Structure of the Hydrogenosomal Malic Enzyme of *Trichomonas vaginalis* and Its Relationship to Homologous Enzymes", *J. Euk Microbiology*, 42(5):593–603, 1995.
Huitorel and Pantaloni, "Bundling of Microtubules by Glyceraldehyde–3 Phosphate Dehydrogenase and Its Modulation by ATP", *European Journal of Biochemistry*, 150:265–269, 1985.
Joe et al., "Nucleotide Sequence of a *Porphyromonas gingivalis* Gene Encoding a Surface–Associated Glutamate Dehydrogenase and Construction of a Glutamate Dehydrogenase–Deficient Isogenic Mutant", *Infection and Immunity*, 62(4):1358–1368, Apr. 1994.

(List continued on next page.)

*Primary Examiner*—Robert A. Wax
*Assistant Examiner*—Enrique D. Longton
*Attorney, Agent, or Firm*—Arnold, White & Durkee

[57] ABSTRACT

Disclosed are novel *Trichomonas vaginalis* adhesin cDNA and amino acid sequences, vectors and host cells. Also disclosed is an iron up-regulated promoter sequence. Methods of differential expression of a gene in the presence of iron and methods of inhibiting Trichomonas cytoadherence are also disclosed.

41 Claims, 11 Drawing Sheets

OTHER PUBLICATIONS

Johnson et al., "Biogenesis of the Hydrogenosome In the Anaerobic Protist *Trichomonas vaginalis*", *Journal of Parasitology*, 79(5):664–670, 1993.

Johnson et al., "Molecular Analysis of the Hydrogenosomal Ferredoxin of the Anaerobic Protist *Trichomonas vaginalis*", *Proc Natl Acad Sci, USA*, 87:6097–6101, Aug. 1990.

Katiyar and Porter, "Fatty Acid Synthetase, Malic Enzyme and Other NADP Binding Dehydrogenases Have Similar Antigenic Determinant(s) At the NADPH Binding Domain", *Biochemical and Biophysical Research Communications*, 112(3):1007–1012, 1983.

Kendrick and Ratledge, "Desaturation of Polyunsaturated Fatty Acids in *Mucor circinelloides* and the Involvement of a Novel Membrane–Bound Malic Enzyme", *European Journal of Biochemisty*, 209:667–673, 1992.

Khoshnan and Alderete, "Characterization of Double–Stranded RNA Satellites Associated With the *Trichomonas vaginalis* Virus", *Journal of Virology*, 69(11):6892–6897, Nov. 1995.

Khoshnan and Alderete, "Multiple Double–Stranded RNA Segments Are Associated With Virus Particles Infecting *Trichomonas vaginalis*", *Journal of Virology*, 67(12):6950–6955, Dec. 1993.

Khoshnan and Alderete, "*Trichomonas vaginalis* With a Double–Stranded RNA Virus Has Upregulated Levels of Phenotypically Variable Immunogen mRNA", *Journal of Virology*, 68(6):4035–4038, Jun. 1994.

Klein et al., "The Detection and Classification of Membrane–Spanning Proteins", *Biochimica et Biophysica Acta*, 815:468–476, 1985.

Kyte and Doolittle, "A Simple Method for Displaying the Hydropathic Character of a Protein", *Journal of Molecular Biology*, 157:105–132, 1982.

Laemmli, "Cleavage of Structural Proteins During the Assembly of the Head of Bacteriophage T4", *Nature*, 227:680–685, Aug. 1970.

Lahti et al., "β–Succinyl–Coenzyme A Synthetase From *Trichomonas vaginalis* Is a Soluble Hydrogenosomal Protein With an Amino–Terminal Sequence That Resembles Mitochondrial Presequences", *Journal of Bacteriology*, 174(21):6822–6830, Nov. 1992.

Länge et al., "Primary Structure of the Hydrogenosomal Adenylate Kinase of *Trichomonas vaginalis* and its Phylogenetic Relationships", *Molecular and Biochemical Parasitology*, 66:297–308, 1994.

Lehker and Alderete, "Iron Regulates Growth of *Trichomonas vaginalis* and the Expression of Immunogenic Trichomonad Proteins", *Molecular Microbiology*, 6(1):123–132, 1992.

Lehker et al., "The Regulation by Iron of the Synthesis of Adhesins and Cytoadherence Levels in the Protozoan *Trichomonas vaginalis*", *Joural of Exp Med*, 174:311–318, Aug. 1991.

Lipman and Pearson, "Rapid and Sensitive Protein similarity Searches", *Science*, 227:1435–1441, Mar. 1985.

Loeber et al., "Human NAD+–Dependent Mitochondrial Malic Enzyme: cDNA Cloning, Primary Structure, and Expression in *Escherichia Coli*", *Journal of Biological Chemistry*, 266(5):3016–3021, Feb. 1991.

Lottenberg et al., "Cloning, Sequence Analysis, and Expression in *Escherichia coli* of a Streptococcal Plasmin Receptor", *Journal of Bacteriology*, 174(16):5204–5210, Aug. 1992.

Mallinson et al., "Identification and Molecular Cloning of Four Cysteine Proteinase Genes From the Pathogenic Protozoon *Trichomonas vaginalis*", *Microbiology*, 140:2725–2735, 1994.

Maniatis et al., "Molecular Cloning: A Laboratory Manual", Cold Spring Harbor Laboratory Press. Cold Spring Harbor, N.Y., 2nd Edition, p. 190, 1982.

Markoŏ et al., "A Glyceraldehyde–3–Phosphate Dehydrogenase With Eubacterial Features in the Amitochondriate Eukaryote, *Trichomonas vaginalis*", *Journal of Molecular Evolution*, 37:631–643, 1993.

McDoneli et al., "Analysis of Restriction Fragments of T7 DNA and Determination of Molecular Weights by Electrophoresis in Neutral and Alkaline Gels", *Journal of Molecular Biology*, 110:119–146 1977.

Meyer–Siegler et al., "A Human Nuclear Uracil DNA Glycosylase is the 37–kDa Subunit of Glyceraldehyde–3–Phosphate Dehydrogenase", *Proc Natl Acad Sci, USA*, 88:8460–8464, Oct. 1991.

Miles et al., "Role of Cell–Surface Lysines in Plasminogen Binding to Cells: Identification of α–Enolase as a Candidate Plasminogen Receptor", *Biochemistry*, 30:1682–1691, 1991.

Mohana Rao and Argos, "A Conformational Preference Parameter to Predict Helices in Integral Membrane Proteins", *Biochimica et Biophysica Acta*, 869:197–214, 1986.

Neale and Alderete, "Analysis of the Proteinases of Representative *Trichomonas vaginalis* Isolates", *Infection and Immunity*, 58(1):157–162, Jan. 1990.

Pancholi and Fischetti, "Glyceraldehyde–3–Phosphate Dehydrogenase on the Surface of Group A Streptococci Is Also an ADP–Ribosylating Enzyme", *Proc Natl Acad Sci, USA*, 90:8154–8158, Sep. 1993.

Pancholi and Fischetti, "A Major Surface Protein on Group A Streptococci Is a Glyceraldehyde–3–Phosphate–Dehydrogenase With Multiple Binding Activity", *Journal of Exp Med*, 176:415–426, Aug. 1992.

Piatigorsky and Wistow, "Enzyme/Crystallins: Gene Sharing as an Evolutionary Strategy", *Cell*, 57:197–199, 1989.

Provenzano and Alderete, "Analysis of Human Immunoglobulin–Degrading Cysteine Proteinases of *Trichomonas vaginalis*", *Infection and Immunity*, 63(9):3388–3395, Sep.1995.

Quon et al., "Similarity Between a Ubiquitous Promoter Element in an Ancient Eukaryote and Mammalian Initiator Elements", *Proc Natl Acad Sci, USA*, 91:4579–4583, May 1994.

Rubino et al., "Molecular Probe for Identification of *Trichomonas vaginalis* DNA", *Journal of Clinical Microbiology*, 29(4):702–706, Apr. 1991.

Satterlee and Hsu, "Duck Liver Malic Enzyme: Sequence of a Tryptic Peptide Containing the Cysteine Residue Labeled by the Substrate Analog Bromopyruvate", *Biochimica et Biophysica Acta*, 1079:247–252, 1991.

Southern, "Gel Electrophoresis of Restriction Fragments", *Methods in Enzymology*, 68:152–177, 1979.

Towbin et al., "Electrophoretic Transfer of Proteins From Polyacrylamide Gels to Nitrocellulose Sheets: Procedure and Some Applications", *Proc Natl Acad Sci, USA*, 76(9):4350–4354, Sep. 1979.

Vacca–Smith et al., "Glucosyltransferase Mediates Adhesion of *Streptococcus gordonii* To Human Endothelial Cells in Vitro", *Infection and Immunity*, 62(6):2187–2194, Jun. 1994.

Von Heijne, "A New Method For Predicting Signal Sequence Cleavage Sites", *Nucleic Acids Research*, 14(11):4683–4690, 1986.

Von Heijne et al., "Domain Structure of Mitochondrial and Chloroplast Targeting Peptides", *European Journal of Biochemistry*, 180:535–545, 1989.

Wagner et al., "Antisense Gene Inhibition by Oligonucleotides Containing C-5 Propyne Pyrimidines", *Science*, 260:1510–1513, Jun. 1993.

Wang and Wang, "The Double–Stranded RNA in *Trichomonas vaginalis* May originate From Virus–Like Particles", *Proc Natl Acad Sci, USA*, 83:7956–7960, Oct. 1986.

Wang et al., "*Trichomonas vaginalis* Phenotypic Variation Occurs Only Among Trichomonads Infected With the Double–Stranded RNA Virus", *Journal Exp Med*, 166:142–150, Jul. 1987.

Wierenga et al., "Interaction of Pyrophosphate Moieties With α–Helixes in Dinucleotide Binding Proteins", *Biochemistry*, 24:1346–1357, 1985.

Wistow, "Lens Crystallins: Gene Recruitment and Evolutionary Dynamism", *TIBS*, 18:301–306, Aug. 1993.

Wistow and Piatigorsky, "Recruitment of Enzymes as Lens Structural Proteins", *Science*, 236:1554–1556, Jun. 1987.

Wood et al., "Base Composition–Independent Hybridization in Tetramethylammonium Chloride: A Method for Oligonucleotide Screening of Highly Complex Gene Libraries", *Proc Natl Acad Sci, USA*, 82:1585–1588, Mar. 1985.

Zhou et al., "Mini–Prep in Ten Minutes", *BioTechniques*, 8(2):172–173, 1990.

Kawamoto and Caswell, "Autophosphorylation of Glyceraldehydephosphate Dehydrogenase and Phosphorylation of Protein from Skeletal Muscle Microsomes", *Biochemistry*, 25:656–661, 1986.

Arroyo, et al. Characterization of cDNAs encoding adhesin proteins involved in *trichomonas vaginalis* cytoadherance. Archives of Medical Research (Mexico), 1995, 26/4 pp. 361–369 (Abstract).

Maniatis et al. (1982) Molecular Cloning A Laboratory Manual. Cold Spring Harbor Laboratory.

Rappelli et al. (Jun. 1, 1995) FEMS Microbiology Letters. vol. 129, pp. 21–26.

Rapelli et al. (1995) Accession Number X83108, GenBank.

Ozaki et al. (1993) Development. vol. 117, No. 4, pp. 1299–1308.

Ozaki et al. (1993) Accession No. D13973, GenBank.

Suske et al. (1987) Eur. J. Biochem. vol. 168, No. 1, pp. 233–237.

Suske et al. (1994) Accession No. X06146, GenBank.

van de Locht et al. (1990) EMBO J. vol. 9, No. 9, pp. 2945–2950.

van de Locht et al. (1991) Accession No. X58698, GenBank.

Lahti et al. (Aug. 1994) Mol. Biochem. Parasitol. vol. 66, No. 2, pp. 309–318.

Lahti et al. (1994) Accession No. L31930, GenBank.

Yanagisawa et al. (1993) J. Biol. Chem. vol. 268, No. 21, pp. 16028–16036.

Yanagisawa et al. (1995) Accession No. X66077, GenBank.

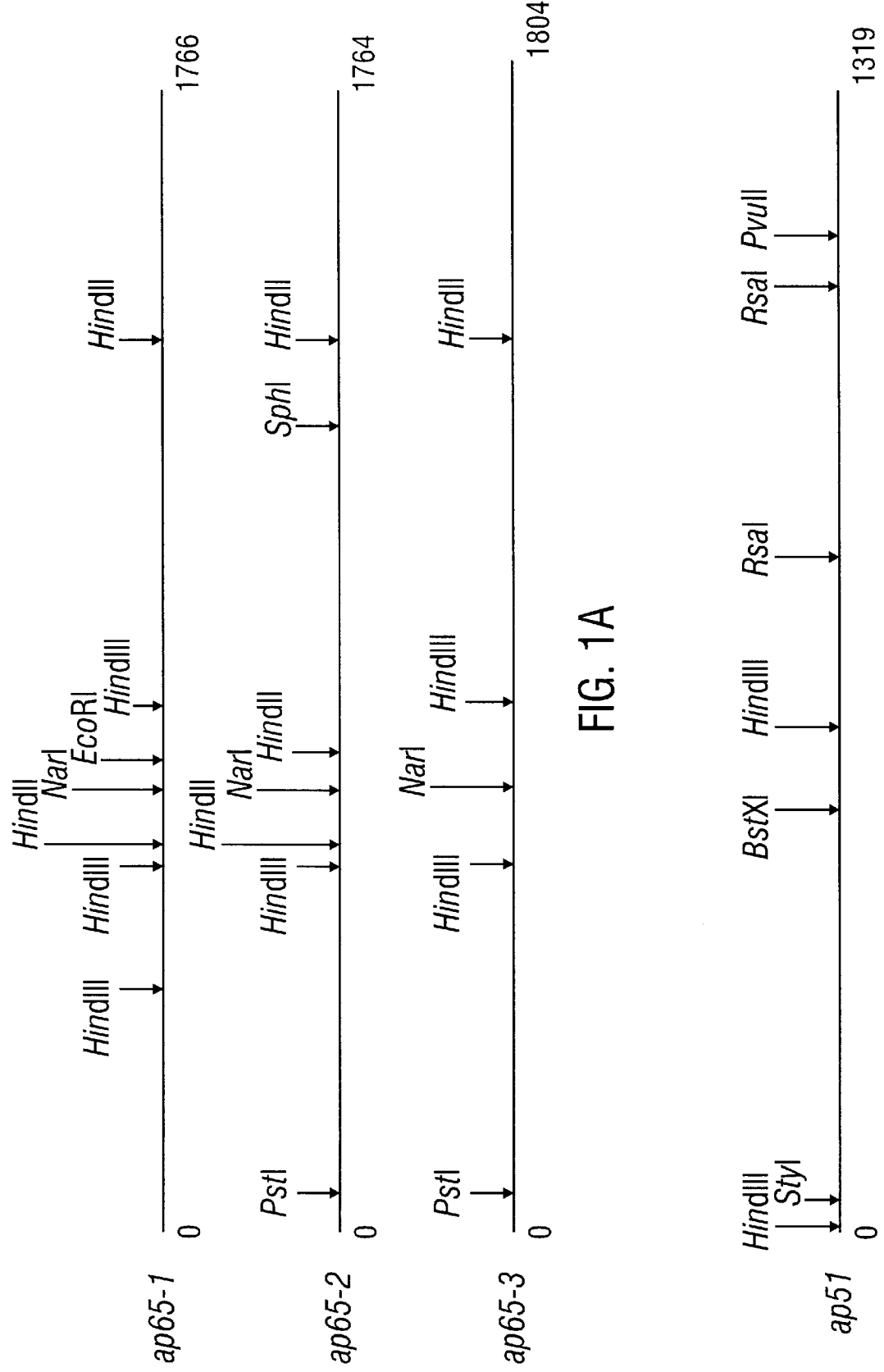

SEQUENCE LISTING (1) GENERAL INFORMATION:

(iii) NUMBER OF SEQUENCES: 30

(2) INFORMATION FOR SEQ ID NO:1:

(i) SEQUENCE CHARACTERISTICS:
      (A) LENGTH: 1766 base pairs
      (B) TYPE: nucleic acid
      (C) STRANDEDNESS: single

```
    (D) TOPOLOGY: linear (ii) MOLECULE TYPE: other nucleic acid
    (A) DESCRIPTION: /desc = "DNA"

(ix) FEATURE:
    (A) NAME/KEY: CDS
    (B) LOCATION: 14..1714

(xi) SEQUENCE DESCRIPTION: SEQ ID NO:1:

TTTTTGATTA AAG ATG CTT ACA TCT TCA GTC TCT CTT CCA GCA CGT GAA         49
           Met Leu Thr Ser Ser Val Ser Leu Pro Ala Arg Glu
           1               5                   10

CTC TCC CGC AAG GTT CTC CCA ACC CTC AAG ACA GGA ATG ACC TTA CTT        97
Leu Ser Arg Lys Val Leu Pro Thr Leu Lys Thr Gly Met Thr Leu Leu
        15              20                  25

CAG GAT GGA GAT CTC AAC AAA GGT ACA GCT TTC ACA AAA GAA GAA CGT        145
Gln Asp Gly Asp Leu Asn Lys Gly Thr Ala Phe Thr Lys Glu Glu Arg
    30              35                  40

GAC CGC TTC AAT CTT CGT GGC CTC CTC CCA TAC AAG GTC TTC ACA AAG        193
Asp Arg Phe Asn Leu Arg Gly Leu Leu Pro Tyr Lys Val Phe Thr Lys
45              50                  55                  60

GAT GAA CAA GCT GCT CGT ATC CGC CGC CAG TTC GAG TTG ATG CCA ACA        241
Asp Glu Gln Ala Ala Arg Ile Arg Arg Gln Phe Glu Leu Met Pro Thr
                65                  70                  75

CCA CTC CTC AAG TAC ATC TTC CTC GCC AAC GAG CGT GAG AAG AAC TCA        289
Pro Leu Leu Lys Tyr Ile Phe Leu Ala Asn Glu Arg Glu Lys Asn Ser
            80                  85                  90

CAG TCC TTC TGG AGA TTC CTC TTC ACA CAC CCA CCA GAG GAA ACA ATG        337
Gln Ser Phe Trp Arg Phe Leu Phe Thr His Pro Pro Glu Glu Thr Met
        95                  100                 105

CCA ATT CTT TAC ACA CCA ACT GTC GGT GAA GCT TGC CAG AAG TGG GCT        385
Pro Ile Leu Tyr Thr Pro Thr Val Gly Glu Ala Cys Gln Lys Trp Ala
    110                 115                 120

ACA CAC CGT CAA TCA TAC CGC GGC ATC TAC ATC ACA CCA GAA GAT TCT        433
Thr His Arg Gln Ser Tyr Arg Gly Ile Tyr Ile Thr Pro Glu Asp Ser
125                 130                 135                 140

GGC AAG ATC AAG GAC ATC CTC CGC AAC TAC CCA CGC CAG GAC ATC CGC        481
Gly Lys Ile Lys Asp Ile Leu Arg Asn Tyr Pro Arg Gln Asp Ile Arg
                145                 150                 155

TGC ATT GTC GTT ACA GAT GCT GGC CGT ATT CTC GGT CTC GGC GAT CTC        529
Cys Ile Val Val Thr Asp Ala Gly Arg Ile Leu Gly Leu Gly Asp Leu
            160                 165                 170

GGT GCT TCC GGC CTT GGT ATT CCA GTT GGT AAG CTT ATG CTT TAC ACA        577
Gly Ala Ser Gly Leu Gly Ile Pro Val Gly Lys Leu Met Leu Tyr Thr
        175                 180                 185

CTT ATC GGC CAA GTT GAC CCA GAT CAG ACA CTT CCA GTC CAG TTA GAT        625
Leu Ile Gly Gln Val Asp Pro Asp Gln Thr Leu Pro Val Gln Leu Asp
    190                 195                 200

ATG GGT ACA GAC AGA AAG GAA ATC CTC GCC GAC CCA CTC TAC CAC GGC        673
Met Gly Thr Asp Arg Lys Glu Ile Leu Ala Asp Pro Leu Tyr His Gly
205                 210                 215                 220

TGG CGC CAT CCA CGT GTA CGT GGC GCT GAG CAC CTC AAG TTC GTC ACA        721
Trp Arg His Pro Arg Val Arg Gly Ala Glu His Leu Lys Phe Val Thr
                225                 230                 235

GAA TTC GTT GAG GCA GTC AAG GAA GTC TTC GGT GAC ACA TGC CTT GTC        769
Glu Phe Val Glu Ala Val Lys Glu Val Phe Gly Asp Thr Cys Leu Val
            240                 245                 250

CAG TTC GAA GAT TTC GAA ATG GAA ACT GCT TTC AAG CTT CTC GAC CAC        817
Gln Phe Glu Asp Phe Glu Met Glu Thr Ala Phe Lys Leu Leu Asp His
        255                 260                 265

TTC AGA TGG CGC TGC AAC TGC TTC AAC GAT GAT ATC GAA GGT ACA GCT        865
```

```
Phe Arg Trp Arg Cys Asn Cys Phe Asn Asp Asp Ile Glu Gly Thr Ala
    270                 275                 280

GCC GTT GCT GCT GCT ACA CTT GCT TCA GCT ACA CAC ATG GAA GGT GTT      913
Ala Val Ala Ala Ala Thr Leu Ala Ser Ala Thr His Met Glu Gly Val
285                 290                 295                 300

CCA GAT CTC AAG AAC CAG AAG ATC ATC TTC ATC GGT GCT GGC TCT GCT      961
Pro Asp Leu Lys Asn Gln Lys Ile Ile Phe Ile Gly Ala Gly Ser Ala
                305                 310                 315

GCC ATA GGC ATT GCT AAC CTC ATT GTC GAT ATG ACA GTT TCC CGC GGT     1009
Ala Ile Gly Ile Ala Asn Leu Ile Val Asp Met Thr Val Ser Arg Gly
                320                 325                 330

GGC ATC ACC AAG GAG CAA GCC TTC AAG AAC ATC ATC ATG TTC GAT CAC     1057
Gly Ile Thr Lys Glu Gln Ala Phe Lys Asn Ile Ile Met Phe Asp His
            335                 340                 345

CGT GGC ATG GTC CAT GCT GGC CGT AAG GAT CTC TAC GAC TTC AAC AAG     1105
Arg Gly Met Val His Ala Gly Arg Lys Asp Leu Tyr Asp Phe Asn Lys
        350                 355                 360

CCA TAC ATG CAC GAC ATG GAA GTC TAC GGC TCA GTT CTC GAG GCC GTC     1153
Pro Tyr Met His Asp Met Glu Val Tyr Gly Ser Val Leu Glu Ala Val
365                 370                 375                 380

AAG AAG TTC AAG GCT ACA TGC GTC ATT GGT GTT TCC GGT GTT CCA GGA     1201
Lys Lys Phe Lys Ala Thr Cys Val Ile Gly Val Ser Gly Val Pro Gly
                385                 390                 395

CTC ATC ACA AAG GAA ATC GTC CAG GCA ACA TTA AAG AAT GCT GAG CAC     1249
Leu Ile Thr Lys Glu Ile Val Gln Ala Thr Leu Lys Asn Ala Glu His
                400                 405                 410

CCA GTC ATC ATG CCA CTT TCC AAC CCA ACA CCA AAG GCT GAA GCT ACA     1297
Pro Val Ile Met Pro Leu Ser Asn Pro Thr Pro Lys Ala Glu Ala Thr
            415                 420                 425

CCA CAC GAT GTT TAC CTT TGG TCC AAT GGC AAG GCC CTC TGC GCT ACA     1345
Pro His Asp Val Tyr Leu Trp Ser Asn Gly Lys Ala Leu Cys Ala Thr
        430                 435                 440

GGC TCA CCA TTC CCA GCC GAA CAA GTC AAC GGC AGA AAG GTC ATC ACT     1393
Gly Ser Pro Phe Pro Ala Glu Gln Val Asn Gly Arg Lys Val Ile Thr
445                 450                 455                 460

GCC CAA GCT AAC AAC TCC TGG ATC TTC CCA GCT GTT GGT TAC GCT CTT     1441
Ala Gln Ala Asn Asn Ser Trp Ile Phe Pro Ala Val Gly Tyr Ala Leu
                465                 470                 475

GTT ACA ACA AAG GCT CGC CAC TGC CCA GCT AAG GTC TTC GAA ATC GCC     1489
Val Thr Thr Lys Ala Arg His Cys Pro Ala Lys Val Phe Glu Ile Ala
                480                 485                 490

GCT GAA TCT CTT GCT TCC CTC GTC AAG AAG GAG GAT CAC GAT CAG GGC     1537
Ala Glu Ser Leu Ala Ser Leu Val Lys Lys Glu Asp His Asp Gln Gly
            495                 500                 505

AAT CTT CTC CCA CCA CTC AAC AAG ATC CGT GAC TAC TCA TTC GGC ATC     1585
Asn Leu Leu Pro Pro Leu Asn Lys Ile Arg Asp Tyr Ser Phe Gly Ile
        510                 515                 520

GCT TAC GAT GTT TCC AAG TAC CTC ATC GAC AAC GAG CTC GCA ACA GCT     1633
Ala Tyr Asp Val Ser Lys Tyr Leu Ile Asp Asn Glu Leu Ala Thr Ala
525                 530                 535                 540

GTT CCA CCA AAG GGT ACA TCT CTC AAG GAC TGG CTC AAG GCT CAG CTC     1681
Val Pro Pro Lys Gly Thr Ser Leu Lys Asp Trp Leu Lys Ala Gln Leu
                545                 550                 555

TTC GAA CCA TCA GCT GAC TAC GAA CCA CTT TAC TAAGCGCGAT TTTTAAACAC   1734
Phe Glu Pro Ser Ala Asp Tyr Glu Pro Leu Tyr
                560                 565

TTAGCTTTCT TAATTTAAAA AAAAAAAAAA AA                                 1766

(2) INFORMATION FOR SEQ ID NO:2:
```

(i) SEQUENCE CHARACTERISTICS:
    (A) LENGTH: 567 amino acids
    (B) TYPE: amino acid
    (D) TOPOLOGY: linear (ii) MOLECULE TYPE: protein (xi) SEQUENCE DESCRIPTION: SEQ ID NO:2:

```
Met Leu Thr Ser Ser Val Ser Leu Pro Ala Arg Glu Leu Ser Arg Lys
 1               5                  10                  15

Val Leu Pro Thr Leu Lys Thr Gly Met Thr Leu Leu Gln Asp Gly Asp
            20                  25                  30

Leu Asn Lys Gly Thr Ala Phe Thr Lys Glu Glu Arg Asp Arg Phe Asn
        35                  40                  45

Leu Arg Gly Leu Leu Pro Tyr Lys Val Phe Thr Lys Asp Glu Gln Ala
    50                  55                  60

Ala Arg Ile Arg Arg Gln Phe Glu Leu Met Pro Thr Pro Leu Leu Lys
65                  70                  75                  80

Tyr Ile Phe Leu Ala Asn Glu Arg Glu Lys Asn Ser Gln Ser Phe Trp
                85                  90                  95

Arg Phe Leu Phe Thr His Pro Glu Glu Thr Met Pro Ile Leu Tyr
            100                 105                 110

Thr Pro Thr Val Gly Glu Ala Cys Gln Lys Trp Ala Thr His Arg Gln
            115                 120                 125

Ser Tyr Arg Gly Ile Tyr Ile Thr Pro Glu Asp Ser Gly Lys Ile Lys
        130                 135                 140

Asp Ile Leu Arg Asn Tyr Pro Arg Gln Asp Ile Arg Cys Ile Val Val
145                 150                 155                 160

Thr Asp Ala Gly Arg Ile Leu Gly Leu Gly Asp Leu Gly Ala Ser Gly
                165                 170                 175

Leu Gly Ile Pro Val Gly Lys Leu Met Leu Tyr Thr Leu Ile Gly Gln
            180                 185                 190

Val Asp Pro Asp Gln Thr Leu Pro Val Gln Leu Asp Met Gly Thr Asp
            195                 200                 205

Arg Lys Glu Ile Leu Ala Asp Pro Leu Tyr His Gly Trp Arg His Pro
        210                 215                 220

Arg Val Arg Gly Ala Glu His Leu Lys Phe Val Thr Glu Phe Val Glu
225                 230                 235                 240

Ala Val Lys Glu Val Phe Gly Asp Thr Cys Leu Val Gln Phe Glu Asp
                245                 250                 255

Phe Glu Met Glu Thr Ala Phe Lys Leu Leu Asp His Phe Arg Trp Arg
            260                 265                 270

Cys Asn Cys Phe Asn Asp Asp Ile Glu Gly Thr Ala Ala Val Ala Ala
        275                 280                 285

Ala Thr Leu Ala Ser Ala Thr His Met Glu Gly Val Pro Asp Leu Lys
    290                 295                 300

Asn Gln Lys Ile Ile Phe Ile Gly Ala Gly Ser Ala Ala Ile Gly Ile
305                 310                 315                 320

Ala Asn Leu Ile Val Asp Met Thr Val Ser Arg Gly Ile Thr Lys
                325                 330                 335

Glu Gln Ala Phe Lys Asn Ile Ile Met Phe Asp His Arg Gly Met Val
            340                 345                 350

His Ala Gly Arg Lys Asp Leu Tyr Asp Phe Asn Lys Pro Tyr Met His
        355                 360                 365

Asp Met Glu Val Tyr Gly Ser Val Leu Glu Ala Val Lys Lys Phe Lys
    370                 375                 380
```

```
Ala Thr Cys Val Ile Gly Val Ser Gly Val Pro Gly Leu Ile Thr Lys
385                 390                 395                 400

Glu Ile Val Gln Ala Thr Leu Lys Asn Ala Glu His Pro Val Ile Met
            405                 410                 415

Pro Leu Ser Asn Pro Thr Pro Lys Ala Glu Ala Thr Pro His Asp Val
            420                 425                 430

Tyr Leu Trp Ser Asn Gly Lys Ala Leu Cys Ala Thr Gly Ser Pro Phe
            435                 440                 445

Pro Ala Glu Gln Val Asn Gly Arg Lys Val Ile Thr Ala Gln Ala Asn
            450                 455                 460

Asn Ser Trp Ile Phe Pro Ala Val Gly Tyr Ala Leu Val Thr Thr Lys
465                 470                 475                 480

Ala Arg His Cys Pro Ala Lys Val Phe Glu Ile Ala Ala Glu Ser Leu
                485                 490                 495

Ala Ser Leu Val Lys Lys Glu Asp His Asp Gln Gly Asn Leu Leu Pro
                500                 505                 510

Pro Leu Asn Lys Ile Arg Asp Tyr Ser Phe Gly Ile Ala Tyr Asp Val
            515                 520                 525

Ser Lys Tyr Leu Ile Asp Asn Glu Leu Ala Thr Ala Val Pro Pro Lys
530                 535                 540

Gly Thr Ser Leu Lys Asp Trp Leu Lys Ala Gln Leu Phe Glu Pro Ser
545                 550                 555                 560

Ala Asp Tyr Glu Pro Leu Tyr
                565
```

(2) INFORMATION FOR SEQ ID NO:3:

(i) SEQUENCE CHARACTERISTICS:
        (A) LENGTH: 1764 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(ix) FEATURE:
        (A) NAME/KEY: CDS
        (B) LOCATION: 15..1715

(xi) SEQUENCE DESCRIPTION: SEQ ID NO:3:

```
TTTTCAGATT AAAG ATG CTC ACA TCT TCA GTC TCT GTT CCA GTC CGC AAC       50
               Met Leu Thr Ser Ser Val Ser Val Pro Val Arg Asn
                1               5                   10

ATC TGC AGG GCT AAG GTC CCA ACC CTC AAG ACA GGC ATG ACA CTC CTT       98
Ile Cys Arg Ala Lys Val Pro Thr Leu Lys Thr Gly Met Thr Leu Leu
        15                  20                  25

CAG GAT GGT GAT CTT TCC AAG GGT TCT GCC TTC ACA AAG GAG GAA CGT      146
Gln Asp Gly Asp Leu Ser Lys Gly Ser Ala Phe Thr Lys Glu Glu Arg
    30                  35                  40

GAC CGC CTT AAC CTC CGC GGC CTT CTC CCA TAC AAG GTC TTC ACA AAG      194
Asp Arg Leu Asn Leu Arg Gly Leu Leu Pro Tyr Lys Val Phe Thr Lys
45                  50                  55                  60

GAT GAA CAA GCT GCT CGT ATC CGC CGC CAG TTC GAA TTA ATG CCA ACA      242
Asp Glu Gln Ala Ala Arg Ile Arg Arg Gln Phe Glu Leu Met Pro Thr
                65                  70                  75

CCA CTC CTC AAG TAC ATC TTC CTC GCT AAC GAG CGT GAG AAA AAC TCA      290
Pro Leu Leu Lys Tyr Ile Phe Leu Ala Asn Glu Arg Glu Lys Asn Ser
            80                  85                  90

CAG TCC TTC TGG AGA TTC CTC TTC ACA CAC CCA CCA GAG GAG ACA ATG      338
```

```
        Gln Ser Phe Trp Arg Phe Leu Phe Thr His Pro Pro Glu Glu Thr Met
                 95                  100                 105

CCA GTT CTC TAC ACA CCA ACA GTT GGT GAA GCC TGC CAG AAG TGG GCT         386
Pro Val Leu Tyr Thr Pro Thr Val Gly Glu Ala Cys Gln Lys Trp Ala
        110                 115                 120

ACA CAC CGC CAG TCA TAC CGT GGC ATC TAC ATC ACA CCA GAA GAC TCT         434
Thr His Arg Gln Ser Tyr Arg Gly Ile Tyr Ile Thr Pro Glu Asp Ser
125                 130                 135                 140

GGC AAG ATC AAG GAC ATC CTC CGC AAC TAC CCA CGC CAG GAC ATC CGC         482
Gly Lys Ile Lys Asp Ile Leu Arg Asn Tyr Pro Arg Gln Asp Ile Arg
                145                 150                 155

TGC ATC GTC GTT ACA GAT GCT GGC CGT ATT CTC GGT CTC GGT GAT CTC         530
Cys Ile Val Val Thr Asp Ala Gly Arg Ile Leu Gly Leu Gly Asp Leu
        160                 165                 170

GGT GCT TCC GGC CTT GGT ATC CCA GTC GGC AAG CTT ATG CTC TAC ACA         578
Gly Ala Ser Gly Leu Gly Ile Pro Val Gly Lys Leu Met Leu Tyr Thr
        175                 180                 185

CTC ATC GGT CAG GTT AAC CCA GAC CAG ACA CTC CCA GTC CAG TTA GAT         626
Leu Ile Gly Gln Val Asn Pro Asp Gln Thr Leu Pro Val Gln Leu Asp
        190                 195                 200

ATG GGT ACA GAC CGC AAG GAA ATC CTT GCC GAC CCA CTC TAC CAC GGC         674
Met Gly Thr Asp Arg Lys Glu Ile Leu Ala Asp Pro Leu Tyr His Gly
205                 210                 215                 220

TGG CGC CAT CCA AGA ATA CGT GGC CCA GAA CAC ACA AAG TTC GTT GCC         722
Trp Arg His Pro Arg Ile Arg Gly Pro Glu His Thr Lys Phe Val Ala
                225                 230                 235

GAG TTC GTT GAC GCT GTC AAG GAA GTC TTT GGC GAG ACA TGC CTT GTC         770
Glu Phe Val Asp Ala Val Lys Glu Val Phe Gly Glu Thr Cys Leu Val
        240                 245                 250

CAG TTC GAA GAC TTC GAA ATG GAA ACA GCC TTC ACA CTC CTC GAC CAC         818
Gln Phe Glu Asp Phe Glu Met Glu Thr Ala Phe Thr Leu Leu Asp His
        255                 260                 265

TTC CGC TGG CGC TGC AAC TGC TTC AAC GAT GAT ATC GAA GGC ACA GCT         866
Phe Arg Trp Arg Cys Asn Cys Phe Asn Asp Asp Ile Glu Gly Thr Ala
        270                 275                 280

GCC GTC GCT GCT GCT ACA CTC GCT TCC GCT ACA CAC ATG GAA GGC GTT         914
Ala Val Ala Ala Ala Thr Leu Ala Ser Ala Thr His Met Glu Gly Val
285                 290                 295                 300

CCA GAT CTC AAG AAC CAG AAG ATC ATC TTC ATT GGC GCT GGC TCT GCT         962
Pro Asp Leu Lys Asn Gln Lys Ile Ile Phe Ile Gly Ala Gly Ser Ala
                305                 310                 315

GCT ACA GGC ATT GCT AAC CTC ATC GTT GAT ATG GCT GTT TCC CGC GGT        1010
Ala Thr Gly Ile Ala Asn Leu Ile Val Asp Met Ala Val Ser Arg Gly
        320                 325                 330

GGC ATC ACA AAG GAA CAG GCT TAC AAG AAC ATC ATC ATG TTC GAT CAC        1058
Gly Ile Thr Lys Glu Gln Ala Tyr Lys Asn Ile Ile Met Phe Asp His
        335                 340                 345

AAG GGT ATG GTC CAT GCT GGC CGT AAG GAT CTC TAC GAC TTC AAC AAG        1106
Lys Gly Met Val His Ala Gly Arg Lys Asp Leu Tyr Asp Phe Asn Lys
350                 355                 360

CCA TAC ATG CAC AAC ATG GAA GTC TAC GGC TCC GTC CTT GAG GGT GTC        1154
Pro Tyr Met His Asn Met Glu Val Tyr Gly Ser Val Leu Glu Gly Val
365                 370                 375                 380

AAG AAG TTC AAG GCT ACC TCC GTC ATC GGC GTT TCT GGT GTT CCA GGA        1202
Lys Lys Phe Lys Ala Thr Ser Val Ile Gly Val Ser Gly Val Pro Gly
                385                 390                 395

CTC ATC ACA AAG GAA ATC GTC CAG GCT GCA TGC GCT AAC TGC GAG CGC        1250
Leu Ile Thr Lys Glu Ile Val Gln Ala Ala Cys Ala Asn Cys Glu Arg
        400                 405                 410

CCA GTC ATC ATG CCA CTT TCC AAC CCA ACA GTC AAG GCT GAA GCT AAG        1298
```

```
                Pro Val Ile Met Pro Leu Ser Asn Pro Thr Val Lys Ala Glu Ala Lys
                                415                 420                 425

CCA CAC GAT GTC TAC CAG TGG TCC AAT GGC AAG GCC CTC TGC GCT ACA                    1346
Pro His Asp Val Tyr Gln Trp Ser Asn Gly Lys Ala Leu Cys Ala Thr
    430                 435                 440

GGC TCT CCA TTC CCA GTT GAG ACA GTC AAC GGA AAG AAG ACA ATC ACA                    1394
Gly Ser Pro Phe Pro Val Glu Thr Val Asn Gly Lys Lys Thr Ile Thr
445                 450                 455                 460

GCC CAG GCT AAC AAC TCC TGG ATC TTC CCA GCT GTC GGC TAC GCC CTC                    1442
Ala Gln Ala Asn Asn Ser Trp Ile Phe Pro Ala Val Gly Tyr Ala Leu
                465                 470                 475

GTT ACA ACA CGC GCT CGC CAC TGC CCA GGC AAG GTC TTC GAA GTT GCT                    1490
Val Thr Thr Arg Ala Arg His Cys Pro Gly Lys Val Phe Glu Val Ala
            480                 485                 490

GCT GAA TCC CTT GCT TCC CTT GTT AAG AAG GAA GAC CAC GAT ATG GGC                    1538
Ala Glu Ser Leu Ala Ser Leu Val Lys Lys Glu Asp His Asp Met Gly
        495                 500                 505

AAC CTT CTC CCA CCA CTC AAC AAG ATC CGT GAC TAC TCA TTC GGC ATC                    1586
Asn Leu Leu Pro Pro Leu Asn Lys Ile Arg Asp Tyr Ser Phe Gly Ile
510                 515                 520

GCC CTC GAT GTT GCT AAG TAC CTC ATC AAG AAC GAG CTT GCT ACA GCC                    1634
Ala Leu Asp Val Ala Lys Tyr Leu Ile Lys Asn Glu Leu Ala Thr Ala
525                 530                 535                 540

GTC CCA CCA AAG GGC ACA GAG CTC AAG GAC TGG CTC AAG GCT CAG CTC                    1682
Val Pro Pro Lys Gly Thr Glu Leu Lys Asp Trp Leu Lys Ala Gln Leu
                545                 550                 555

TTC GAT CCA CAG GCT GAA TAC GAG CAA CTC TAT TAAATCTATT AAAGTTTCTG                  1735
Phe Asp Pro Gln Ala Glu Tyr Glu Gln Leu Tyr
            560                 565

GTTGATTATT TATGAAAAAA AAAAAAAAA                                                    1764

(2) INFORMATION FOR SEQ ID NO:4:

(i) SEQUENCE CHARACTERISTICS:
        (A) LENGTH: 567 amino acids
        (B) TYPE: amino acid
        (D) TOPOLOGY: linear (ii) MOLECULE TYPE: protein (xi) SEQUENCE DESCRIPTION: SEQ ID NO:4:

Met Leu Thr Ser Ser Val Ser Val Pro Val Arg Asn Ile Cys Arg Ala
 1               5                  10                  15

Lys Val Pro Thr Leu Lys Thr Gly Met Thr Leu Leu Gln Asp Gly Asp
                20                  25                  30

Leu Ser Lys Gly Ser Ala Phe Thr Lys Glu Glu Arg Asp Arg Leu Asn
            35                  40                  45

Leu Arg Gly Leu Leu Pro Tyr Lys Val Phe Thr Lys Asp Glu Gln Ala
        50                  55                  60

Ala Arg Ile Arg Arg Gln Phe Glu Leu Met Pro Thr Pro Leu Leu Lys
65                  70                  75                  80

Tyr Ile Phe Leu Ala Asn Glu Arg Glu Lys Asn Ser Gln Ser Phe Trp
                85                  90                  95

Arg Phe Leu Phe Thr His Pro Pro Glu Glu Thr Met Pro Val Leu Tyr
            100                 105                 110

Thr Pro Thr Val Gly Glu Ala Cys Gln Lys Trp Ala Thr His Arg Gln
        115                 120                 125

Ser Tyr Arg Gly Ile Tyr Ile Thr Pro Glu Asp Ser Gly Lys Ile Lys
130                 135                 140
```

```
Asp Ile Leu Arg Asn Tyr Pro Arg Gln Asp Ile Arg Cys Ile Val Val
145                 150                 155                 160

Thr Asp Ala Gly Arg Ile Leu Gly Leu Gly Asp Leu Gly Ala Ser Gly
                165                 170                 175

Leu Gly Ile Pro Val Gly Lys Leu Met Leu Tyr Thr Leu Ile Gly Gln
            180                 185                 190

Val Asn Pro Asp Gln Thr Leu Pro Val Gln Leu Asp Met Gly Thr Asp
        195                 200                 205

Arg Lys Glu Ile Leu Ala Asp Pro Leu Tyr His Gly Trp Arg His Pro
210                 215                 220

Arg Ile Arg Gly Pro Glu His Thr Lys Phe Val Ala Glu Phe Val Asp
225                 230                 235                 240

Ala Val Lys Glu Val Phe Gly Glu Thr Cys Leu Val Gln Phe Glu Asp
                245                 250                 255

Phe Glu Met Glu Thr Ala Phe Thr Leu Leu Asp His Phe Arg Trp Arg
            260                 265                 270

Cys Asn Cys Phe Asn Asp Asp Ile Glu Gly Thr Ala Ala Val Ala Ala
        275                 280                 285

Ala Thr Leu Ala Ser Ala Thr His Met Glu Gly Val Pro Asp Leu Lys
290                 295                 300

Asn Gln Lys Ile Ile Phe Ile Gly Ala Gly Ser Ala Ala Thr Gly Ile
305                 310                 315                 320

Ala Asn Leu Ile Val Asp Met Ala Val Ser Arg Gly Gly Ile Thr Lys
                325                 330                 335

Glu Gln Ala Tyr Lys Asn Ile Ile Met Phe Asp His Lys Gly Met Val
            340                 345                 350

His Ala Gly Arg Lys Asp Leu Tyr Asp Phe Asn Lys Pro Tyr Met His
        355                 360                 365

Asn Met Glu Val Tyr Gly Ser Val Leu Glu Gly Val Lys Lys Phe Lys
370                 375                 380

Ala Thr Ser Val Ile Gly Val Ser Gly Val Pro Gly Leu Ile Thr Lys
385                 390                 395                 400

Glu Ile Val Gln Ala Ala Cys Ala Asn Cys Glu Arg Pro Val Ile Met
                405                 410                 415

Pro Leu Ser Asn Pro Thr Val Lys Ala Glu Ala Lys Pro His Asp Val
            420                 425                 430

Tyr Gln Trp Ser Asn Gly Lys Ala Leu Cys Ala Thr Gly Ser Pro Phe
        435                 440                 445

Pro Val Glu Thr Val Asn Gly Lys Lys Thr Ile Thr Ala Gln Ala Asn
450                 455                 460

Asn Ser Trp Ile Phe Pro Ala Val Gly Tyr Ala Leu Val Thr Thr Arg
465                 470                 475                 480

Ala Arg His Cys Pro Gly Lys Val Phe Glu Val Ala Ala Glu Ser Leu
                485                 490                 495

Ala Ser Leu Val Lys Lys Glu Asp His Asp Met Gly Asn Leu Leu Pro
            500                 505                 510

Pro Leu Asn Lys Ile Arg Asp Tyr Ser Phe Gly Ile Ala Leu Asp Val
        515                 520                 525

Ala Lys Tyr Leu Ile Lys Asn Glu Leu Ala Thr Ala Val Pro Pro Lys
530                 535                 540

Gly Thr Glu Leu Lys Asp Trp Leu Lys Ala Gln Leu Phe Asp Pro Gln
545                 550                 555                 560

Ala Glu Tyr Glu Gln Leu Tyr
                565
```

(2) INFORMATION FOR SEQ ID NO:5:

(i) SEQUENCE CHARACTERISTICS:
        (A) LENGTH: 1804 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(ix) FEATURE:
        (A) NAME/KEY: CDS
        (B) LOCATION: 14..1714

(xi) SEQUENCE DESCRIPTION: SEQ ID NO:5:

```
TTTTAGATTA AAG ATG CTC GCA TCT TCA GTC GCT GCT CCA GTC CGC AAC          49
           Met Leu Ala Ser Ser Val Ala Ala Pro Val Arg Asn
             1               5                  10

ATC TGC AGG GCT AAG CTC CCA GCT CTC AAG ACA GGA ATG ACC CTC CTT         97
Ile Cys Arg Ala Lys Leu Pro Ala Leu Lys Thr Gly Met Thr Leu Leu
             15                  20                  25

CAG GAT GGT GAT CTT TCC AAG GGC TCT GCT TTC ACA AAG GAA GAA CGT        145
Gln Asp Gly Asp Leu Ser Lys Gly Ser Ala Phe Thr Lys Glu Glu Arg
     30                  35                  40

GAT CGC CTT AAC CTT CGC GGT CTC CTC CCA TAC AAG GTC TTC ACA AAG        193
Asp Arg Leu Asn Leu Arg Gly Leu Leu Pro Tyr Lys Val Phe Thr Lys
 45                  50                  55                  60

GAT GAA CAA GCT GCT CGT ATC CGC CGC CAG TTC GAG TTG ATG CCA ACA        241
Asp Glu Gln Ala Ala Arg Ile Arg Arg Gln Phe Glu Leu Met Pro Thr
                 60                  65                  70

CCA CTC CTC AAG TAC ATC TTC CTC GCT AAC GAG CGT GAG AAA AAC TCA        289
Pro Leu Leu Lys Tyr Ile Phe Leu Ala Asn Glu Arg Glu Lys Asn Ser
             75                  80                  85

CAG TCC TTC TGG AGA TTC CTC TTC ACA CAC CCA CCA ACA GAG ACA ATG        337
Gln Ser Phe Trp Arg Phe Leu Phe Thr His Pro Pro Thr Glu Thr Met
         95                 100                 105

CCA GTT CTC TAC ACA CCA ACA GTT GGT GAA GCC TGC CAG AAG TGG GCT        385
Pro Val Leu Tyr Thr Pro Thr Val Gly Glu Ala Cys Gln Lys Trp Ala
    110                 115                 120

ACA CAC CGC CAG TCA TAC CGT GGC ATC TAC ATC ACA CCA GAA GAC TCT        433
Thr His Arg Gln Ser Tyr Arg Gly Ile Tyr Ile Thr Pro Glu Asp Ser
125                 130                 135                 140

GGC AAG ATC AAG GAC ATC CTC CGC AAC TAC CCA CGC CAG GAC ATC CGC        481
Gly Lys Ile Lys Asp Ile Leu Arg Asn Tyr Pro Arg Gln Asp Ile Arg
                145                 150                 155

TGC ATC GTC GTT ACA GAT GGT GGC CGT ATC CTC GGT CTC GGT GAT CTC        529
Cys Ile Val Val Thr Asp Gly Gly Arg Ile Leu Gly Leu Gly Asp Leu
            160                 165                 170

GGT GCT TCC GGC CTT GGT ATC CCA GTC GGC AAG CTT ATG CTT TAC ACA        577
Gly Ala Ser Gly Leu Gly Ile Pro Val Gly Lys Leu Met Leu Tyr Thr
        175                 180                 185

CTC ATC GGT CAG GTC CAT CCA GAT CAG ACA CTC CCA GTC CAG TTA GAT        625
Leu Ile Gly Gln Val His Pro Asp Gln Thr Leu Pro Val Gln Leu Asp
    190                 195                 200

ATG GGT ACA GAC CGC AAG GAA ATC CTC GCC GAC CCA CTC TAC CAC GGC        673
Met Gly Thr Asp Arg Lys Glu Ile Leu Ala Asp Pro Leu Tyr His Gly
205                 210                 215                 220

TGG CGC CAT CCA AGA ATA CGT GGC CCA GAA CAC ACA AAG TTC GTT GCC        721
Trp Arg His Pro Arg Ile Arg Gly Pro Glu His Thr Lys Phe Val Ala
                225                 230                 235

GAG TTC GTT GAT GCT GTC AAG GAA GTC TTT GGC GAG ACA TGC CTT GTC        769
```

```

Glu Phe Val Asp Ala Val Lys Glu Val Phe Gly Glu Thr Cys Leu Val
                    240                 245                 250

CAG TTC GAA GAT TTC GAA ATG GAA ACT GCT TTC AAG CTT CTT GAT CAC            817
Gln Phe Glu Asp Phe Glu Met Glu Thr Ala Phe Lys Leu Leu Asp His
            255                 260                 265

TTC CGC TGG CGC TGC AAC TGC TTC AAC GAT GAT ATC GAA GGC ACA GCT            865
Phe Arg Trp Arg Cys Asn Cys Phe Asn Asp Asp Ile Glu Gly Thr Ala
270                 275                 280

GCC GTC GCT GCT GCT ACA CTC GCT TCC GCT ACA CAC ATG GAA GGC GTT            913
Ala Val Ala Ala Ala Thr Leu Ala Ser Ala Thr His Met Glu Gly Val
285                 290                 295                 300

CCA GAT CTC AAG AAC CAG AAG ATC ATC TTC ATC GGC GCT GGC TCT GCT            961
Pro Asp Leu Lys Asn Gln Lys Ile Ile Phe Ile Gly Ala Gly Ser Ala
                305                 310                 315

GCT ACA GGC ATT GCT AAC CTC ATC GTT GAT ATG GCT GTT TCC CGC GGT           1009
Ala Thr Gly Ile Ala Asn Leu Ile Val Asp Met Ala Val Ser Arg Gly
            320                 325                 330

GGC ATC TCA CGC AAG GAT GCT GAG AGA AAC ATC ATC ATG TTC GAT CAC           1057
Gly Ile Ser Arg Lys Asp Ala Glu Arg Asn Ile Ile Met Phe Asp His
        335                 340                 345

AAG GGT ATG GTC CAT GCT GAC CGT AAG GAT CTC TAC GAC TTC AAC AAG           1105
Lys Gly Met Val His Ala Asp Arg Lys Asp Leu Tyr Asp Phe Asn Lys
    350                 355                 360

CCA TAC ATG CAC GAC ATG GAA GTC TAC GGC TCC GTC CTT GAG GGT GTC           1153
Pro Tyr Met His Asp Met Glu Val Tyr Gly Ser Val Leu Glu Gly Val
365                 370                 375                 380

AAG AAG TTC AAG GCT ACA TGC GTC ATC GGC GTT TCT GGT GTT CCA GGA           1201
Lys Lys Phe Lys Ala Thr Cys Val Ile Gly Val Ser Gly Val Pro Gly
                385                 390                 395

CTC ATC ACA AAG GAA ATC GTC CAG GCT ACA TGC GCT AAC TGC GAG CGC           1249
Leu Ile Thr Lys Glu Ile Val Gln Ala Thr Cys Ala Asn Cys Glu Arg
            400                 405                 410

CCA GTC ATC ATG CCA CTT TCC AAC CCA ACA GTC AAG GCT GAA GCT AAG           1297
Pro Val Ile Met Pro Leu Ser Asn Pro Thr Val Lys Ala Glu Ala Lys
        415                 420                 425

CCA CAC GAT GTC TAC CAG TGG TCC AAT GGC AAG GCC CTC TGC GCT ACA           1345
Pro His Asp Val Tyr Gln Trp Ser Asn Gly Lys Ala Leu Cys Ala Thr
    430                 435                 440

GGC TCT CCA TTC CCA GTT GAG ACA GTC AAC GGA AAG AAG ACA ATC ACA           1393
Gly Ser Pro Phe Pro Val Glu Thr Val Asn Gly Lys Lys Thr Ile Thr
445                 450                 455                 460

GCT CAG GCT AAC AAC TCC TGG ATC TTC CCA GCT GTC GGC TAC GCC CTC           1441
Ala Gln Ala Asn Asn Ser Trp Ile Phe Pro Ala Val Gly Tyr Ala Leu
                465                 470                 475

GTT ACA ACA CGC GCT CGC CAC TGC CCA GGC AAG GTC TTC GAA GTT GCT           1489
Val Thr Thr Arg Ala Arg His Cys Pro Gly Lys Val Phe Glu Val Ala
            480                 485                 490

GCT GAA TCC CTT GCT TCC CTT GTT AAG AAG GAA GAC CAC GAT ATG GGC           1537
Ala Glu Ser Leu Ala Ser Leu Val Lys Lys Glu Asp His Asp Met Gly
        495                 500                 505

AAC CTT CTC CCA CCA CTC GAC AAG ATC CGT GAG TAC TCA TTC GGC ATC           1585
Asn Leu Leu Pro Pro Leu Asp Lys Ile Arg Glu Tyr Ser Phe Gly Ile
    510                 515                 520

GCC CTC GAT GTT GCT AAG TAC CTC ATC AAG AAC GAG CTC GCC ACA GCT           1633
Ala Leu Asp Val Ala Lys Tyr Leu Ile Lys Asn Glu Leu Ala Thr Ala
525                 530                 535                 540

CTC CCA CCA AAG GGC ACA GAG CTC AAG GAC TGG CTC AAG GCT CAG CTC           1681
Leu Pro Pro Lys Gly Thr Glu Leu Lys Asp Trp Leu Lys Ala Gln Leu
                545                 550                 555

TTC GAT CCA CAG GCT GAA TAC GAG CAA CTC TAC TAAGCAGTTT TTAAAACTCT         1734
Phe Asp Pro Gln Ala Glu Tyr Glu Gln Leu Tyr
```

-continued

```
Phe Asp Pro Gln Ala Glu Tyr Glu Gln Leu Tyr
        560                 565
```

TTCAATTGTC TTTGAAAAAA AAAAAAAAAA AAAAAAAAAA AAAAAAAAAA AAAAAAAAAA    1794

AAAAAAAAAA    1804

(2) INFORMATION FOR SEQ ID NO:6:

(i) SEQUENCE CHARACTERISTICS:
        (A) LENGTH: 567 amino acids
        (B) TYPE: amino acid
        (D) TOPOLOGY: linear (ii) MOLECULE TYPE: protein (xi) SEQUENCE DESCRIPTION: SEQ ID NO:6:

```
Met Leu Ala Ser Ser Val Ala Ala Pro Val Arg Asn Ile Cys Arg Ala
 1               5                  10                  15

Lys Leu Pro Ala Leu Lys Thr Gly Met Thr Leu Leu Gln Asp Gly Asp
             20                  25                  30

Leu Ser Lys Gly Ser Ala Phe Thr Lys Glu Glu Arg Asp Arg Leu Asn
         35                  40                  45

Leu Arg Gly Leu Leu Pro Tyr Lys Val Phe Thr Lys Asp Glu Gln Ala
     50                  55                  60

Ala Arg Ile Arg Arg Gln Phe Glu Leu Met Pro Thr Pro Leu Leu Lys
 65                  70                  75                  80

Tyr Ile Phe Leu Ala Asn Glu Arg Glu Lys Asn Ser Gln Ser Phe Trp
                 85                  90                  95

Arg Phe Leu Phe Thr His Pro Pro Thr Glu Thr Met Pro Val Leu Tyr
            100                 105                 110

Thr Pro Thr Val Gly Glu Ala Cys Gln Lys Trp Ala Thr His Arg Gln
        115                 120                 125

Ser Tyr Arg Gly Ile Tyr Ile Thr Pro Glu Asp Ser Gly Lys Ile Lys
    130                 135                 140

Asp Ile Leu Arg Asn Tyr Pro Arg Gln Asp Ile Arg Cys Ile Val Val
145                 150                 155                 160

Thr Asp Gly Gly Arg Ile Leu Gly Leu Gly Asp Leu Gly Ala Ser Gly
                165                 170                 175

Leu Gly Ile Pro Val Gly Lys Leu Met Leu Tyr Thr Leu Ile Gly Gln
            180                 185                 190

Val His Pro Asp Gln Thr Leu Pro Val Gln Leu Asp Met Gly Thr Asp
        195                 200                 205

Arg Lys Glu Ile Leu Ala Asp Pro Leu Tyr His Gly Trp Arg His Pro
    210                 215                 220

Arg Ile Arg Gly Pro Glu His Thr Lys Phe Val Ala Glu Phe Val Asp
225                 230                 235                 240

Ala Val Lys Glu Val Phe Gly Glu Thr Cys Leu Val Gln Phe Glu Asp
                245                 250                 255

Phe Glu Met Glu Thr Ala Phe Lys Leu Leu Asp His Phe Arg Trp Arg
            260                 265                 270

Cys Asn Cys Phe Asn Asp Asp Ile Glu Gly Thr Ala Ala Val Ala Ala
        275                 280                 285

Ala Thr Leu Ala Ser Ala Thr His Met Glu Gly Val Pro Asp Leu Lys
    290                 295                 300

Asn Gln Lys Ile Ile Phe Ile Gly Ala Gly Ser Ala Ala Thr Gly Ile
305                 310                 315                 320

Ala Asn Leu Ile Val Asp Met Ala Val Ser Arg Gly Gly Ile Ser Arg
```

```
                    325                 330                 335
Lys Asp Ala Glu Arg Asn Ile Ile Met Phe Asp His Lys Gly Met Val
                340                 345                 350
His Ala Asp Arg Lys Asp Leu Tyr Asp Phe Asn Lys Pro Tyr Met His
            355                 360                 365
Asp Met Glu Val Tyr Gly Ser Val Leu Glu Gly Val Lys Lys Phe Lys
        370                 375                 380
Ala Thr Cys Val Ile Gly Val Ser Gly Val Pro Gly Leu Ile Thr Lys
385                 390                 395                 400
Glu Ile Val Gln Ala Thr Cys Ala Asn Cys Glu Arg Pro Val Ile Met
                405                 410                 415
Pro Leu Ser Asn Pro Thr Val Lys Ala Glu Ala Lys Pro His Asp Val
                420                 425                 430
Tyr Gln Trp Ser Asn Gly Lys Ala Leu Cys Ala Thr Gly Ser Pro Phe
            435                 440                 445
Pro Val Glu Thr Val Asn Gly Lys Lys Thr Ile Thr Ala Gln Ala Asn
        450                 455                 460
Asn Ser Trp Ile Phe Pro Ala Val Gly Tyr Ala Leu Val Thr Thr Arg
465                 470                 475                 480
Ala Arg His Cys Pro Gly Lys Val Phe Glu Val Ala Ala Glu Ser Leu
                485                 490                 495
Ala Ser Leu Val Lys Lys Glu Asp His Asp Met Gly Asn Leu Leu Pro
                500                 505                 510
Pro Leu Asp Lys Ile Arg Glu Tyr Ser Phe Gly Ile Ala Leu Asp Val
            515                 520                 525
Ala Lys Tyr Leu Ile Lys Asn Glu Leu Ala Thr Ala Leu Pro Pro Lys
        530                 535                 540
Gly Thr Glu Leu Lys Asp Trp Leu Lys Ala Gln Leu Phe Asp Pro Gln
545                 550                 555                 560
Ala Glu Tyr Glu Gln Leu Tyr
                565

(2) INFORMATION FOR SEQ ID NO:7:

(i) SEQUENCE CHARACTERISTICS:
        (A) LENGTH: 1319 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(ix) FEATURE:
        (A) NAME/KEY: CDS
        (B) LOCATION: 3..1214

(xi) SEQUENCE DESCRIPTION: SEQ ID NO:7:

GA AGC TTT GCC CGT AAC TTC AAC ATC CTT GAA TGG CAA TCC AAG GAA           47
   Ser Phe Ala Arg Asn Phe Asn Ile Leu Glu Trp Gln Ser Lys Glu
   1               5                  10                  15

ATC TGC GCC AAA TTC AAC GTT GCT GCT GGT ATC AAC CTT GTT GCT CGC          95
Ile Cys Ala Lys Phe Asn Val Ala Ala Gly Ile Asn Leu Val Ala Arg
                20                  25                  30

ACA CCA GAA GAG GCT GCT GCT GCA TTC AAG AAG ATG GGA CTC CCA GCC         143
Thr Pro Glu Glu Ala Ala Ala Ala Phe Lys Lys Met Gly Leu Pro Ala
            35                  40                  45

GCC GTC ATC AAG GCT CAG GTC TAC TGC GGT GGC CGT GGC AAG GGC CAT         191
Ala Val Ile Lys Ala Gln Val Tyr Cys Gly Gly Arg Gly Lys Gly His
        50                  55                  60
```

```
TGG AAG GAA ACA GGC TTC AAG TCT GGC GTT CAC TTC GTA AAG TCC GCC        239
Trp Lys Glu Thr Gly Phe Lys Ser Gly Val His Phe Val Lys Ser Ala
 65                  70                  75

GAT GAG GCC GCC AAG ATC GCT AAG GAG ATG CTT GGC CAC CAC CTT GTT        287
Asp Glu Ala Ala Lys Ile Ala Lys Glu Met Leu Gly His His Leu Val
 80                  85                  90                  95

ACA AAG CAG ACA GGC GCT GAT GGT CTC CTC TGC CAG GCT GTC ATG CTC        335
Thr Lys Gln Thr Gly Ala Asp Gly Leu Leu Cys Gln Ala Val Met Leu
                    100                 105                 110

TCC GAC CCA GTC GAA GTT AAG CGT GAA CTC TAC TTC GCT ATC CTT CTC        383
Ser Asp Pro Val Glu Val Lys Arg Glu Leu Tyr Phe Ala Ile Leu Leu
                115                 120                 125

GAC CGC CAG ACA CAG TCT CCA GTC GTC ATC GCC TCC ACA GAG GGT GGT        431
Asp Arg Gln Thr Gln Ser Pro Val Val Ile Ala Ser Thr Glu Gly Gly
            130                 135                 140

GTC GAA ATT GAA GAA GTC GCT GCC AAG CAC CCA GAG AAG ATC CTC AAG        479
Val Glu Ile Glu Glu Val Ala Ala Lys His Pro Glu Lys Ile Leu Lys
145                 150                 155

TTC CAG CTC GAT GGT GTT GAG GGC ATC ACA CGC GAT GTT GCT GTT AAC        527
Phe Gln Leu Asp Gly Val Glu Gly Ile Thr Arg Asp Val Ala Val Asn
160                 165                 170                 175

ATC TCC AAG CAA CTC GGT CTC ACA GGC AAG GCT TAC GAG AAC GGT ATT        575
Ile Ser Lys Gln Leu Gly Leu Thr Gly Lys Ala Tyr Glu Asn Gly Ile
                180                 185                 190

GAG GAA ATG CAG AAG CTT TGG AAG CTC TTC GTT GGC TCC GAT GCT ACA        623
Glu Glu Met Gln Lys Leu Trp Lys Leu Phe Val Gly Ser Asp Ala Thr
                195                 200                 205

CAG GTC GAG GTT AAC CCA CTC GCC GAG ACA ACA GAT GGC CGC ATC ATC        671
Gln Val Glu Val Asn Pro Leu Ala Glu Thr Thr Asp Gly Arg Ile Ile
            210                 215                 220

ACA GTC GAC TCC AAG TTC AAC TTC GAT GAC TCC GCT CAC TAC CGC CAG        719
Thr Val Asp Ser Lys Phe Asn Phe Asp Asp Ser Ala His Tyr Arg Gln
225                 230                 235

AAG CAG ATC TTC GGC TAT CGT GAC CTC AAG CAA GTC AAC CCA TTC GAA        767
Lys Gln Ile Phe Gly Tyr Arg Asp Leu Lys Gln Val Asn Pro Phe Glu
240                 245                 250                 255

ATC CGC GCT GAG AAG TAC GGT CTT AAC TAC GTC CCA CTC GAT GGT AAC        815
Ile Arg Ala Glu Lys Tyr Gly Leu Asn Tyr Val Pro Leu Asp Gly Asn
                260                 265                 270

GTC GCT TGC CTC GTT AAC GGT GCT GGC CTT GCT ATG GCT ACA ATG GAT        863
Val Ala Cys Leu Val Asn Gly Ala Gly Leu Ala Met Ala Thr Met Asp
                275                 280                 285

GTC ATC CAA CTT GCC GGT GGT GAT CCA GCT AAC TTC CTC GAT CTC GGT        911
Val Ile Gln Leu Ala Gly Gly Asp Pro Ala Asn Phe Leu Asp Leu Gly
            290                 295                 300

GGT GGT GCT TCT GAA GCT GCC GTT ACA GAG GGC TTC ACA ATC ATC TCA        959
Gly Gly Ala Ser Glu Ala Ala Val Thr Glu Gly Phe Thr Ile Ile Ser
305                 310                 315

TCT CAG CCA CAC GTA AAG GCT ATC CTC GTC AAC ATC TTC GGT GGT ATC       1007
Ser Gln Pro His Val Lys Ala Ile Leu Val Asn Ile Phe Gly Gly Ile
320                 325                 330                 335

GTC CGC TGC GAC ATG GTC GCT GCT GGT GTC ATC GCC GCC TTC AAG AAG       1055
Val Arg Cys Asp Met Val Ala Ala Gly Val Ile Ala Ala Phe Lys Lys
                340                 345                 350

GTT GGC CTC AAG GTC CCA CTC GTT GTC CGC CTC GAG GGT ACA AAC GTC       1103
Val Gly Leu Lys Val Pro Leu Val Val Arg Leu Glu Gly Thr Asn Val
                355                 360                 365

GAT GCC GGT AAG AAG CTC ATC CGC GAA TCC GGC CTC CCA ATC ATC CCA       1151
Asp Ala Gly Lys Lys Leu Ile Arg Glu Ser Gly Leu Pro Ile Ile Pro
            370                 375                 380
```

```
GCT GAC AAC CTT ACA GAC GCT GGT ATC AAG GCT GTC AAG GCT GCT AAC    1199
Ala Asp Asn Leu Thr Asp Ala Gly Ile Lys Ala Val Lys Ala Ala Asn
        385                 390                 395

GGT GAG AAG CTC ATC TAAAGAGGTT TGCAAATTAA AATTCTAAAG TTATCAACAT    1254
Gly Glu Lys Leu Ile
400

CTGATTCAAA AAAAAAAAAA AAAAAAAAAA AAAAAAAAAA AAAAAAAAAA AAAAAAAAA   1314

AAAAA                                                              1319

(2) INFORMATION FOR SEQ ID NO:8:

(i) SEQUENCE CHARACTERISTICS:
        (A) LENGTH: 404 amino acids
        (B) TYPE: amino acid
        (D) TOPOLOGY: linear (ii) MOLECULE TYPE: protein (xi) SEQUENCE DESCRIPTION: SEQ ID NO:8:

Ser Phe Ala Arg Asn Phe Asn Ile Leu Glu Trp Gln Ser Lys Glu Ile
 1               5                  10                  15

Cys Ala Lys Phe Asn Val Ala Ala Gly Ile Asn Leu Val Ala Arg Thr
            20                  25                  30

Pro Glu Ala Ala Ala Ala Phe Lys Lys Met Gly Leu Pro Ala Ala
        35                  40                  45

Val Ile Lys Ala Gln Val Tyr Cys Gly Arg Gly Lys Gly His Trp
 50                  55                  60

Lys Glu Thr Gly Phe Lys Ser Gly Val His Phe Val Lys Ser Ala Asp
 65                  70                  75                  80

Glu Ala Ala Lys Ile Ala Lys Glu Met Leu Gly His His Leu Val Thr
                85                  90                  95

Lys Gln Thr Gly Ala Asp Gly Leu Leu Cys Gln Ala Val Met Leu Ser
            100                 105                 110

Asp Pro Val Glu Val Lys Arg Glu Leu Tyr Phe Ala Ile Leu Leu Asp
        115                 120                 125

Arg Gln Thr Gln Ser Pro Val Val Ile Ala Ser Thr Glu Gly Gly Val
130                 135                 140

Glu Ile Glu Glu Val Ala Ala Lys His Pro Glu Lys Ile Leu Lys Phe
145                 150                 155                 160

Gln Leu Asp Gly Val Glu Gly Ile Thr Arg Asp Val Ala Val Asn Ile
                165                 170                 175

Ser Lys Gln Leu Gly Leu Thr Gly Lys Ala Tyr Glu Asn Gly Ile Glu
            180                 185                 190

Glu Met Gln Lys Leu Trp Lys Leu Phe Val Gly Ser Asp Ala Thr Gln
        195                 200                 205

Val Glu Val Asn Pro Leu Ala Glu Thr Thr Asp Gly Arg Ile Ile Thr
    210                 215                 220

Val Asp Ser Lys Phe Asn Phe Asp Asp Ser Ala His Tyr Arg Gln Lys
225                 230                 235                 240

Gln Ile Phe Gly Tyr Arg Asp Leu Lys Gln Val Asn Pro Phe Glu Ile
                245                 250                 255

Arg Ala Glu Lys Tyr Gly Leu Asn Tyr Val Pro Leu Asp Gly Asn Val
            260                 265                 270

Ala Cys Leu Val Asn Gly Ala Gly Leu Ala Met Ala Thr Met Asp Val
        275                 280                 285

Ile Gln Leu Ala Gly Gly Asp Pro Ala Asn Phe Leu Asp Leu Gly Gly
```

```
                    290                 295                 300
Gly Ala Ser Glu Ala Ala Val Thr Glu Gly Phe Thr Ile Ile Ser Ser
305                 310                 315                 320

Gln Pro His Val Lys Ala Ile Leu Val Asn Ile Phe Gly Gly Ile Val
                325                 330                 335

Arg Cys Asp Met Val Ala Ala Gly Val Ile Ala Ala Phe Lys Lys Val
                340                 345                 350

Gly Leu Lys Val Pro Leu Val Val Arg Leu Glu Gly Thr Asn Val Asp
                355                 360                 365

Ala Gly Lys Lys Leu Ile Arg Glu Ser Gly Leu Pro Ile Ile Pro Ala
                370                 375                 380

Asp Asn Leu Thr Asp Ala Gly Ile Lys Ala Val Lys Ala Ala Asn Gly
385                 390                 395                 400

Glu Lys Leu Ile (2) INFORMATION FOR SEQ ID NO:9:

(i) SEQUENCE CHARACTERISTICS:
        (A) LENGTH: 976 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(ix) FEATURE:
        (A) NAME/KEY: CDS
        (B) LOCATION: 1..897

(xi) SEQUENCE DESCRIPTION: SEQ ID NO:9:

CAT CAA CCA CTC CTC TTC ATT GAC AAG GAC ACA AGA GTT GTT ATC CAA        48
His Gln Pro Leu Leu Phe Ile Asp Lys Asp Thr Arg Val Val Ile Gln
  1               5                  10                  15

GGT ATC GGT AAC CAA GGC CAA TAT CAC TCC CGC CTC ATG CGT GAA TAC        96
Gly Ile Gly Asn Gln Gly Gln Tyr His Ser Arg Leu Met Arg Glu Tyr
                 20                  25                  30

GGC ACA AAG GTT GTT GGT GCT GTT CAT CCA AAG AAG GCC GGA AAG ATC       144
Gly Thr Lys Val Val Gly Ala Val His Pro Lys Lys Ala Gly Lys Ile
         35                  40                  45

ATT GCT GGA CTT CCA ATC TTC AAG AAC ATG AAG GAA GTT GTT AAG AGA       192
Ile Ala Gly Leu Pro Ile Phe Lys Asn Met Lys Glu Val Val Lys Arg
 50                  55                  60

ACA GAT GCT AAT GCA TCT CTT ATC TTC GTT CCA GCT CCA GGT GCT GCT       240
Thr Asp Ala Asn Ala Ser Leu Ile Phe Val Pro Ala Pro Gly Ala Ala
 65                  70                  75                  80

GCT GCA TGC ATT GAA GCT GCT GAA GCC GGC ATG GGT CTT GTT GTC TGC       288
Ala Ala Cys Ile Glu Ala Ala Glu Ala Gly Met Gly Leu Val Val Cys
                 85                  90                  95

ATC ACA GAA CAC ATC CCA CAG CAC GAT ATG ATC AAG GTC AAG AAG GTC       336
Ile Thr Glu His Ile Pro Gln His Asp Met Ile Lys Val Lys Lys Val
            100                 105                 110

ATG AAG GAA ACA GGC TGC CAG CTC ATC GGT CCA AAC TGC CCA GGT CTT       384
Met Lys Glu Thr Gly Cys Gln Leu Ile Gly Pro Asn Cys Pro Gly Leu
        115                 120                 125

ATC CAG CCA GGC ACA CAC ACA AAG CTT GGT ATC ATC CCA ACA AAC ATC       432
Ile Gln Pro Gly Thr His Thr Lys Leu Gly Ile Ile Pro Thr Asn Ile
    130                 135                 140

TTC AGA AAC GGT AAG ATC GGT ATT GTT TCC CGC TCT GGT ACA CTT ACA       480
Phe Arg Asn Gly Lys Ile Gly Ile Val Ser Arg Ser Gly Thr Leu Thr
145                 150                 155                 160
```

```
TAT GAA GCT GCT TAT GCT ACA ACA CAA GCT GGC CTT GGT CAG TCC ACA       528
Tyr Glu Ala Ala Tyr Ala Thr Thr Gln Ala Gly Leu Gly Gln Ser Thr
            165                 170                 175

GTT GTC GGC ATT GGT GGT GAT CCA TTC GCA GGA CAG CTC CAC ACA GAT       576
Val Val Gly Ile Gly Gly Asp Pro Phe Ala Gly Gln Leu His Thr Asp
            180                 185                 190

GTC ATC AAG CGC TTT GCT GCA GAT CCA CAG ACC GAG GGT ATC ATC CTT       624
Val Ile Lys Arg Phe Ala Ala Asp Pro Gln Thr Glu Gly Ile Ile Leu
            195                 200                 205

ATC GGT GAA ATC GGT GGC ACA TCC GAA GAA GAT GCC GCT GAG TGG ATC       672
Ile Gly Glu Ile Gly Gly Thr Ser Glu Glu Asp Ala Ala Glu Trp Ile
            210                 215                 220

GCT AAG ACA AAG CTT ACC CAG GAG AAG CCA GTC GTC GCC TTC ATC GCC       720
Ala Lys Thr Lys Leu Thr Gln Glu Lys Pro Val Val Ala Phe Ile Ala
225                 230                 235                 240

GGC GCT ACA GCT CCA CCA GGC AAG CGT ATG GGT CAC GCT GGT GCC ATC       768
Gly Ala Thr Ala Pro Pro Gly Lys Arg Met Gly His Ala Gly Ala Ile
                245                 250                 255

GTT TCT GGC GGC AAG GGC ACA GCT GAG GGC AAG TAC AAG GCT CTT GAA       816
Val Ser Gly Gly Lys Gly Thr Ala Glu Gly Lys Tyr Lys Ala Leu Glu
            260                 265                 270

GCA GCT GGT GTT CGC ATT GCT CGC CAC CCA GGT AAC ATG GGC AAG TTC       864
Ala Ala Gly Val Arg Ile Ala Arg His Pro Gly Asn Met Gly Lys Phe
            275                 280                 285

ATC TTC GAG GAG ATG AAG AGA TTA GGA AAG ATC TAAATCTACT GCTTACTTTA    917
Ile Phe Glu Glu Met Lys Arg Leu Gly Lys Ile
            290                 295

AAAAAAAAAA AAAAAAAAAA AAAAAAAAAA AAAAAAAAAA AAAAAAAAAA AAAAAAAA      976

(2) INFORMATION FOR SEQ ID NO:10:

(i) SEQUENCE CHARACTERISTICS:
        (A) LENGTH: 299 amino acids
        (B) TYPE: amino acid
        (D) TOPOLOGY: linear (ii) MOLECULE TYPE: protein (xi) SEQUENCE DESCRIPTION: SEQ ID NO:10:

His Gln Pro Leu Leu Phe Ile Asp Lys Asp Thr Arg Val Val Ile Gln
 1               5                  10                  15

Gly Ile Gly Asn Gln Gly Gln Tyr His Ser Arg Leu Met Arg Glu Tyr
                20                  25                  30

Gly Thr Lys Val Val Gly Ala Val His Pro Lys Lys Ala Gly Lys Ile
            35                  40                  45

Ile Ala Gly Leu Pro Ile Phe Lys Asn Met Lys Glu Val Val Lys Arg
    50                  55                  60

Thr Asp Ala Asn Ala Ser Leu Ile Phe Val Pro Ala Pro Gly Ala Ala
65                  70                  75                  80

Ala Ala Cys Ile Glu Ala Ala Glu Ala Gly Met Gly Leu Val Val Cys
                85                  90                  95

Ile Thr Glu His Ile Pro Gln His Asp Met Ile Lys Val Lys Lys Val
            100                 105                 110

Met Lys Glu Thr Gly Cys Gln Leu Ile Gly Pro Asn Cys Pro Gly Leu
        115                 120                 125

Ile Gln Pro Gly Thr His Thr Lys Leu Gly Ile Ile Pro Thr Asn Ile
    130                 135                 140

Phe Arg Asn Gly Lys Ile Gly Ile Val Ser Arg Ser Gly Thr Leu Thr
145                 150                 155                 160
```

```
Tyr Glu Ala Ala Tyr Ala Thr Thr Gln Ala Gly Leu Gly Gln Ser Thr
            165                 170                 175

Val Val Gly Ile Gly Gly Asp Pro Phe Ala Gly Gln Leu His Thr Asp
            180                 185                 190

Val Ile Lys Arg Phe Ala Ala Asp Pro Gln Thr Glu Gly Ile Ile Leu
            195                 200                 205

Ile Gly Glu Ile Gly Gly Thr Ser Glu Glu Asp Ala Ala Glu Trp Ile
        210                 215                 220

Ala Lys Thr Lys Leu Thr Gln Glu Lys Pro Val Val Ala Phe Ile Ala
225                 230                 235                 240

Gly Ala Thr Ala Pro Pro Gly Lys Arg Met Gly His Ala Gly Ala Ile
                245                 250                 255

Val Ser Gly Gly Lys Gly Thr Ala Glu Gly Lys Tyr Lys Ala Leu Glu
            260                 265                 270

Ala Ala Gly Val Arg Ile Ala Arg His Pro Gly Asn Met Gly Lys Phe
        275                 280                 285

Ile Phe Glu Glu Met Lys Arg Leu Gly Lys Ile
290                 295
```

(2) INFORMATION FOR SEQ ID NO:11:

(i) SEQUENCE CHARACTERISTICS:
        (A) LENGTH: 947 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(ix) FEATURE:
        (A) NAME/KEY: CDS
        (B) LOCATION: 1..891

(xi) SEQUENCE DESCRIPTION: SEQ ID NO:11:

```
CCA CTC CTT TTC ATC GAC AAG GAC ACC AAG GTC GTC ATC CAG GGT ATC      48
Pro Leu Leu Phe Ile Asp Lys Asp Thr Lys Val Val Ile Gln Gly Ile
 1               5                  10                  15

GGT AAC CAG GGC CAG TTC CAC TCC CGC CTT ATG CGC CAG TAT GGC ACA      96
Gly Asn Gln Gly Gln Phe His Ser Arg Leu Met Arg Gln Tyr Gly Thr
                20                  25                  30

AAG GTT GTT GGT GCC GTC CAT CCA AAG AAG GCC GGC TCA ATC ATT GCT     144
Lys Val Val Gly Ala Val His Pro Lys Lys Ala Gly Ser Ile Ile Ala
            35                  40                  45

GGT CTC CCA ATC TTC AAG AAC ATG AAG GAG GTT GTC AAG AGA ACA GAT     192
Gly Leu Pro Ile Phe Lys Asn Met Lys Glu Val Val Lys Arg Thr Asp
        50                  55                  60

GCT AAT GCC TCC CTC ATT TTC GTC CCA GCT CCA GGC GCT GCT GCT GCT     240
Ala Asn Ala Ser Leu Ile Phe Val Pro Ala Pro Gly Ala Ala Ala Ala
65                  70                  75                  80

TGC ATT GAA GCT GCT CAG GCT GGC ATG GGT CTC GTT GTC TGC ATC ACA     288
Cys Ile Glu Ala Ala Gln Ala Gly Met Gly Leu Val Val Cys Ile Thr
                85                  90                  95

GAA CAC ATC CCA CAG CAC GAC ATG ATC AAG GTC AAG AAG GTC ATG AAG     336
Glu His Ile Pro Gln His Asp Met Ile Lys Val Lys Lys Val Met Lys
                100                 105                 110

GAA ACA GGC TGC CAG CTT ATC GGT CCA AAC TGC CCA GGT CTT ATC CAG     384
Glu Thr Gly Cys Gln Leu Ile Gly Pro Asn Cys Pro Gly Leu Ile Gln
            115                 120                 125

CCA GGC ACA CAC ACA AAG CTT GGT ATC ATC CCA ACA AAC ATC TTC AAC     432
Pro Gly Thr His Thr Lys Leu Gly Ile Ile Pro Thr Asn Ile Phe Asn
        130                 135                 140
```

```
AAC GGT AAG ATC GGT ATT GTT TCC CGC TCC GGC ACA CTC ACA TAC GAA        480
Asn Gly Lys Ile Gly Ile Val Ser Arg Ser Gly Thr Leu Thr Tyr Glu
145                 150                 155                 160

GCT GCC TAC GCT ACA ACA CTC GCT GGC CTT GGT CAG TCC ACA GTT GTC        528
Ala Ala Tyr Ala Thr Thr Leu Ala Gly Leu Gly Gln Ser Thr Val Val
                165                 170                 175

GGC ATC GGT GGT GAT CCA TTC GCA GGC CAA CTC CAC ACA GAT GTT GTC        576
Gly Ile Gly Gly Asp Pro Phe Ala Gly Gln Leu His Thr Asp Val Val
            180                 185                 190

AAG CGC TTC GCT GCA GAC CCA CAG ACC GAG GGT ATC ATC CTC ATC GGT        624
Lys Arg Phe Ala Ala Asp Pro Gln Thr Glu Gly Ile Ile Leu Ile Gly
        195                 200                 205

GAA ATC GGT GGC ACA TCC GAA GAA GAT GCC GCT GAG TGG ATC GCT AAG        672
Glu Ile Gly Gly Thr Ser Glu Glu Asp Ala Ala Glu Trp Ile Ala Lys
    210                 215                 220

ACA AAG CTT ACC CAG GAG AAG CCA GTC GTC GCC TTC ATC GCC GGC GCT        720
Thr Lys Leu Thr Gln Glu Lys Pro Val Val Ala Phe Ile Ala Gly Ala
225                 230                 235                 240

ACA GCT CCA CCA GGC AAG CGT ATG GGT CAC GCT GGT GCC ATC GTT TCT        768
Thr Ala Pro Pro Gly Lys Arg Met Gly His Ala Gly Ala Ile Val Ser
                245                 250                 255

GGC GGC AAG GGC ACA GCT GAG GGC AAG TAC AAG GCT CTT GAA GCA GCT        816
Gly Gly Lys Gly Thr Ala Glu Gly Lys Tyr Lys Ala Leu Glu Ala Ala
            260                 265                 270

GGT GTT CGC ATT GCT CGC CAC CCA GGT AAC ATG GGC AAG TTC ATC TTC        864
Gly Val Arg Ile Ala Arg His Pro Gly Asn Met Gly Lys Phe Ile Phe
        275                 280                 285

GAG GAG ATG AAG AGA ATG GGC AAG ATC TAAATTTCTC ATAAAAGTTC              911
Glu Glu Met Lys Arg Met Gly Lys Ile
    290                 295

ACAATTCAAT AACCTAATTA CAAAAAAAAA AAAAAA                                947

(2) INFORMATION FOR SEQ ID NO:12:

(i) SEQUENCE CHARACTERISTICS:
        (A) LENGTH: 297 amino acids
        (B) TYPE: amino acid
        (D) TOPOLOGY: linear (ii) MOLECULE TYPE: protein (xi) SEQUENCE DESCRIPTION: SEQ ID NO:12:

Pro Leu Leu Phe Ile Asp Lys Asp Thr Lys Val Val Ile Gln Gly Ile
1               5                   10                  15

Gly Asn Gln Gly Gln Phe His Ser Arg Leu Met Arg Gln Tyr Gly Thr
            20                  25                  30

Lys Val Val Gly Ala Val His Pro Lys Lys Ala Gly Ser Ile Ile Ala
        35                  40                  45

Gly Leu Pro Ile Phe Lys Asn Met Lys Glu Val Val Lys Arg Thr Asp
    50                  55                  60

Ala Asn Ala Ser Leu Ile Phe Val Pro Ala Pro Gly Ala Ala Ala Ala
65                  70                  75                  80

Cys Ile Glu Ala Ala Gln Ala Gly Met Gly Leu Val Val Cys Ile Thr
                85                  90                  95

Glu His Ile Pro Gln His Asp Met Ile Lys Val Lys Lys Val Met Lys
            100                 105                 110

Glu Thr Gly Cys Gln Leu Ile Gly Pro Asn Cys Pro Gly Leu Ile Gln
        115                 120                 125

Pro Gly Thr His Thr Lys Leu Gly Ile Ile Pro Thr Asn Ile Phe Asn
```

```
                    130                 135                 140
Asn Gly Lys Ile Gly Ile Val Ser Arg Ser Gly Thr Leu Thr Tyr Glu
145                 150                 155                 160

Ala Ala Tyr Ala Thr Thr Leu Ala Gly Leu Gly Gln Ser Thr Val Val
                165                 170                 175

Gly Ile Gly Gly Asp Pro Phe Ala Gly Gln Leu His Thr Asp Val Val
            180                 185                 190

Lys Arg Phe Ala Ala Asp Pro Gln Thr Glu Gly Ile Ile Leu Ile Gly
        195                 200                 205

Glu Ile Gly Gly Thr Ser Glu Glu Asp Ala Ala Glu Trp Ile Ala Lys
    210                 215                 220

Thr Lys Leu Thr Gln Glu Lys Pro Val Val Ala Phe Ile Ala Gly Ala
225                 230                 235                 240

Thr Ala Pro Pro Gly Lys Arg Met Gly His Ala Gly Ala Ile Val Ser
                245                 250                 255

Gly Gly Lys Gly Thr Ala Glu Gly Lys Tyr Lys Ala Leu Glu Ala Ala
            260                 265                 270

Gly Val Arg Ile Ala Arg His Pro Gly Asn Met Gly Lys Phe Ile Phe
        275                 280                 285

Glu Glu Met Lys Arg Met Gly Lys Ile
    290                 295

(2) INFORMATION FOR SEQ ID NO:13:

(i) SEQUENCE CHARACTERISTICS:
        (A) LENGTH: 974 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "DNA"

(ix) FEATURE:
         (A) NAME/KEY: CDS
         (B) LOCATION: 1..885

(xi) SEQUENCE DESCRIPTION: SEQ ID NO:13:

CTT TTC ATC GAC AAG GAC ACC AAG GTT GTT ATC CAG GGT ATC GGT AAC      48
Leu Phe Ile Asp Lys Asp Thr Lys Val Val Ile Gln Gly Ile Gly Asn
 1               5                  10                  15

CAG GGC CAG TTC CAC TCC CGC CTT ATG CGC CAG TAT GGC ACA AAG GTT      96
Gln Gly Gln Phe His Ser Arg Leu Met Arg Gln Tyr Gly Thr Lys Val
                20                  25                  30

GTT GGT GCT GTC CAT CCA AAG AAG GCT GGC ACA ATC ATT GCT GGT CTC     144
Val Gly Ala Val His Pro Lys Lys Ala Gly Thr Ile Ile Ala Gly Leu
            35                  40                  45

CCA ATC TTC AAG AAC ATG AAG GAG GTT GTT AAG AGA ACA GAT GCT AAT     192
Pro Ile Phe Lys Asn Met Lys Glu Val Val Lys Arg Thr Asp Ala Asn
        50                  55                  60

GCA TCT CTT ATC TTC GTT CCA GCT CCA GGT GCT GCT GCT GCA TGC ATT     240
Ala Ser Leu Ile Phe Val Pro Ala Pro Gly Ala Ala Ala Ala Cys Ile
 65                  70                  75                  80

GAA GCT GCT GAA GCC GGC ATG GGT CTT GTT GTC TGC ATC ACA GAA CAC     288
Glu Ala Ala Glu Ala Gly Met Gly Leu Val Val Cys Ile Thr Glu His
                85                  90                  95

ATC CCA CAG CAC GAC ATG ATC AAG GTC AAG AAG GTC ATG AAG GAA ACA     336
Ile Pro Gln His Asp Met Ile Lys Val Lys Lys Val Met Lys Glu Thr
            100                 105                 110

GGC TGC CAG CTT ATC GGT CCA AAC TGC CCA GGT CTT ATC CAG CCA GGC     384
Gly Cys Gln Leu Ile Gly Pro Asn Cys Pro Gly Leu Ile Gln Pro Gly
```

```
                    115                 120                 125
ACA CAC ACA AAG CTT GGT ATC ATC CCA ACA AAC ATC TTC AAC AAC GGT    432
Thr His Thr Lys Leu Gly Ile Ile Pro Thr Asn Ile Phe Asn Asn Gly
        130                 135                 140

AAG ATC GGT ATT GTT TCC CGC TCC GGC ACA CTC ACA TAC GAA GCT GCC    480
Lys Ile Gly Ile Val Ser Arg Ser Gly Thr Leu Thr Tyr Glu Ala Ala
145                 150                 155                 160

TAC GCT ACA ACA CTC GCT GGC CTT GGT CAG TCC ACA GTT GTC GGC ATC    528
Tyr Ala Thr Thr Leu Ala Gly Leu Gly Gln Ser Thr Val Val Gly Ile
                165                 170                 175

GGT GGT GAT CCA TTC GCA GGC CAA CTC CAC ACA GAT GTT GTC AAG CGC    576
Gly Gly Asp Pro Phe Ala Gly Gln Leu His Thr Asp Val Val Lys Arg
            180                 185                 190

TTC GCT GCA GAC CCA CAG ACC GAG GGT ATC ATC CTC ATC GGT GAA ATC    624
Phe Ala Ala Asp Pro Gln Thr Glu Gly Ile Ile Leu Ile Gly Glu Ile
            195                 200                 205

GGT GGC ACA TCC GAA GAA GAT GCC GCT GAG TGG ATC GCT AAG ACA AAG    672
Gly Gly Thr Ser Glu Glu Asp Ala Ala Glu Trp Ile Ala Lys Thr Lys
    210                 215                 220

CTT ACC CAG GAG AAG CCA GTC GTC GCC TTC ATC GCC GGC GCT ACA GCT    720
Leu Thr Gln Glu Lys Pro Val Val Ala Phe Ile Ala Gly Ala Thr Ala
225                 230                 235                 240

CCA CCA GGC AAG CGT ATG GGC CAC GCT GGT GCC ATC GTT TCT GGC GGC    768
Pro Pro Gly Lys Arg Met Gly His Ala Gly Ala Ile Val Ser Gly Gly
                245                 250                 255

AAG GGC ACA GCT GAG GGC AAG TAC AAG GCT CTT GAA GCA GCT GGT GTT    816
Lys Gly Thr Ala Glu Gly Lys Tyr Lys Ala Leu Glu Ala Ala Gly Val
            260                 265                 270

CGC ATT GCT CGT CAC CCA GGT AAC ATG GGC AAG TTC ATC TTC GAG GAG    864
Arg Ile Ala Arg His Pro Gly Asn Met Gly Lys Phe Ile Phe Glu Glu
            275                 280                 285

ATG AAG AGA ATG GGC AAG ATC TAAAGTTTCC ATATCTTATT AAATCGATTT       915
Met Lys Arg Met Gly Lys Ile
        290                 295

TGAATGTTCA AAAAAAAAAA AAAAAAAAAA AAAAAAAAAA AAAAAAAAAA AAAAAAAA    974

(2) INFORMATION FOR SEQ ID NO:14:

(i) SEQUENCE CHARACTERISTICS:
        (A) LENGTH: 295 amino acids
        (B) TYPE: amino acid
        (D) TOPOLOGY: linear (ii) MOLECULE TYPE: protein (xi) SEQUENCE DESCRIPTION: SEQ ID NO:14:

Leu Phe Ile Asp Lys Asp Thr Lys Val Val Ile Gln Gly Ile Gly Asn
 1               5                  10                  15

Gln Gly Gln Phe His Ser Arg Leu Met Arg Gln Tyr Gly Thr Lys Val
            20                  25                  30

Val Gly Ala Val His Pro Lys Lys Ala Gly Thr Ile Ile Ala Gly Leu
        35                  40                  45

Pro Ile Phe Lys Asn Met Lys Glu Val Val Lys Arg Thr Asp Ala Asn
    50                  55                  60

Ala Ser Leu Ile Phe Val Pro Ala Pro Gly Ala Ala Ala Ala Cys Ile
65                  70                  75                  80

Glu Ala Ala Glu Ala Gly Met Gly Leu Val Val Cys Ile Thr Glu His
                85                  90                  95

Ile Pro Gln His Asp Met Ile Lys Val Lys Lys Val Met Lys Glu Thr
            100                 105                 110
```

Gly Cys Gln Leu Ile Gly Pro Asn Cys Pro Gly Leu Ile Gln Pro Gly
            115                 120                 125

Thr His Thr Lys Leu Gly Ile Ile Pro Thr Asn Ile Phe Asn Asn Gly
            130                 135                 140

Lys Ile Gly Ile Val Ser Arg Ser Gly Thr Leu Thr Tyr Glu Ala Ala
145                 150                 155                 160

Tyr Ala Thr Thr Leu Ala Gly Leu Gly Gln Ser Thr Val Val Gly Ile
                165                 170                 175

Gly Gly Asp Pro Phe Ala Gly Gln Leu His Thr Asp Val Val Lys Arg
            180                 185                 190

Phe Ala Ala Asp Pro Gln Thr Glu Gly Ile Ile Leu Ile Gly Glu Ile
            195                 200                 205

Gly Gly Thr Ser Glu Glu Asp Ala Ala Glu Trp Ile Ala Lys Thr Lys
            210                 215                 220

Leu Thr Gln Glu Lys Pro Val Val Ala Phe Ile Ala Gly Ala Thr Ala
225                 230                 235                 240

Pro Pro Gly Lys Arg Met Gly His Ala Gly Ala Ile Val Ser Gly Gly
            245                 250                 255

Lys Gly Thr Ala Glu Gly Lys Tyr Lys Ala Leu Glu Ala Ala Gly Val
            260                 265                 270

Arg Ile Ala Arg His Pro Gly Asn Met Gly Lys Phe Ile Phe Glu Glu
            275                 280                 285

Met Lys Arg Met Gly Lys Ile
290                 295

(2) INFORMATION FOR SEQ ID NO:15:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:15:

GCGGATACGA GCAGCTTGTT CATCC                                                    25

(2) INFORMATION FOR SEQ ID NO:16:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:16:

GAATTCGAAT TCGAGGAGGC CACGAAGATT GAAGCGG                                        37

(2) INFORMATION FOR SEQ ID NO:17:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:17:

CTCCTTTGTG AAGGCAGAAC CC                                             22

(2) INFORMATION FOR SEQ ID NO:18:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Thr Cys Ala Tyr Thr Trp Tyr Thr Cys Ala Thr Thr Ala
    1               5                  10

(2) INFORMATION FOR SEQ ID NO:19:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Ile Leu Gly Leu Gly Lys Leu Gly Ala Ser Gly Leu Gly Ile Pro Val
    1               5                  10                  15

Gly Lys Leu Met Leu
                20

(2) INFORMATION FOR SEQ ID NO:20:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Ile Leu Gly Leu Gly Asp Leu Gly Ala Ser Gly Leu Gly Ile Pro Val
    1               5                  10                  15

Gly Lys Leu Met Leu
                20

(2) INFORMATION FOR SEQ ID NO:21:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Gly Thr Ala Ala Val Ala Ala Thr Leu Ala Ser Ala Thr
    1               5                  10

(2) INFORMATION FOR SEQ ID NO:22:

(i) SEQUENCE CHARACTERISTICS:
        (A) LENGTH: 22 amino acids (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

Ile Ile Phe Ile Gly Ala Gly Ser Ala Ala Ile Gly Ile Ala Asn Leu
    1               5                   10                  15

Ile Val Asp Met Thr Val
                20

(2) INFORMATION FOR SEQ ID NO:23:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

Ile Ile Phe Ile Gly Ala Gly Ser Ala Ala Thr Gly Ile Ala Asn Leu
    1               5                   10                  15

Ile Val Asp Met Ala Val
                20

(2) INFORMATION FOR SEQ ID NO:24:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

Cys Val Ile Gly Val Ser Gly Val Pro Gly Leu Ile Thr Lys Glu Ile
    1               5                   10                  15

Val Gln Ala Thr Leu
                20

(2) INFORMATION FOR SEQ ID NO:25:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

Val Ile Gly Val Ser Gly Val Pro Gly Leu Ile Thr Lys Glu Ile Val
    1               5                   10                  15

Gln Ala Ala Cys Ala
                20

(2) INFORMATION FOR SEQ ID NO:26:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

Val Ile Gly Val Ser Gly Val Pro Gly Leu Ile Thr Lys Glu Ile Val
1               5                   10                  15

Gln Ala Thr Cys Ala
            20

(2) INFORMATION FOR SEQ ID NO:27:

(i) SEQUENCE CHARACTERISTICS:
      (A) LENGTH: 21 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:27:

Val Ile Thr Ala Gln Ala Asn Asn Ser Trp Ile Phe Pro Ala Val Gly
1               5                   10                  15

Tyr Ala Leu Val Thr
            20

(2) INFORMATION FOR SEQ ID NO:28:

(i) SEQUENCE CHARACTERISTICS:
      (A) LENGTH: 21 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:28:

Thr Ile Thr Ala Gln Ala Asn Asn Ser Trp Ile Phe Pro Ala Val Gly
1               5                   10                  15

Tyr Ala Leu Val Thr
            20

(2) INFORMATION FOR SEQ ID NO:29:

(i) SEQUENCE CHARACTERISTICS:
      (A) LENGTH: 6 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Modified-site
      (B) LOCATION: 2..5
      (D) OTHER INFORMATION: /note= "Xaa = any amino acid"

(xi) SEQUENCE DESCRIPTION: SEQ ID NO:29:

Gly Xaa Gly Xaa Xaa Gly
1               5

(2) INFORMATION FOR SEQ ID NO:30:

(i) SEQUENCE CHARACTERISTICS:
      (A) LENGTH: 6 amino acids
      (B) TYPE: amino acid
      (C) STRANDEDNESS: single
      (D) TOPOLOGY: linear (ii) MOLECULE TYPE: peptide

```
(ix) FEATURE:
    (A) NAME/KEY: Modified-site
    (B) LOCATION: 2..5
    (D) OTHER INFORMATION: /note= "Xaa = any amino acid"

(xi) SEQUENCE DESCRIPTION: SEQ ID NO:30:

Gly Xaa Gly Xaa Xaa Ala
1               5
```

ADHESIN GENES AND PROTEINS INVOLVED IN *TRICHOMONAS VAGINALIS* CYTOADHERENCE

The government owns rights in the present invention pursuant to Public Health Service grant (number 1 RO1 AI-18768) from the National Institutes of Allergy and Infectious Diseases, National Institutes of Health.

BACKGROUND OF THE INVENTION

1. Field of the Invention

The present invention relates generally to the field of sexually transmitted diseases and in particular to the protozoan parasite *Trichomonas vaginalis*. The invention also relates to the field of proteins that mediate the property of cytoadherence and to the ability of *T. vaginalis* parasites to attach to the human vaginal epithelial cells.

2. Description of the Related Art

The flagellated eukaryote, *Trichomonas vaginalis* is the etiologic agent of one of the most common sexually transmitted diseases among humans. In order to establish and maintain infection, the parasite must be able to withstand the hostile environment of the human urogenital tract. This parasite must evade immune surveillance mechanisms, such as resisting lytic antibody and complement (Alderete et al., 1987; 1991) and, equally important, overcome the constant fluid flow of the vagina. Consequently, cytoadherence by the parasite to the vaginal epithelium (Alderete and Garza, 1985; 1988a; Alderete et al., 1988b; Arroyo et al., 1992; 1993; Lehker et al., 1991) is essential for initiation and maintenance of infection and fundamental to parasite survival. The cytoadherence mechanism of *T. vaginalis* is complex and represents a cascade of reactions, which include a role for proteinase activity (Arroyo and Alderete, 1989) and signaling of the parasite after initial attachment (Arroyo et al., 1993).

Trichomonal cytoadherence has been shown to be ligand-receptor in nature (Alderete and Garza, 1988a; Arroyo et al., 1992; Lehker et al., 1991). Four trichomonad proteins (AP65, AP51, AP33, and AP23) have been identified as the adhesins that specifically mediate attachment to receptors on the vaginal epithelial cells (VECs) (Alderete and Garza, 1988a; Arroyo et al., 1992). That these proteins are authentic adhesins was established through fulfillment of criteria, and the relationship between levels of cytoadherence and surface expression of synthesized adhesins was established (Arroyo et al., 1992). Trichomonads expressing low levels of adhesins (Arroyo et al., 1992) have been shown to signal for enhanced synthesis of all adhesins immediately after cytoadherence (Arroyo et al., 1993). Gene expression of the four adhesins was found to be coordinately regulated at the transcriptional level by iron (Lehker et al., 1991), and such regulation may be a mechanism by which the parasite adapts to the constantly changing environment in the vagina. The adhesins are very sensitive to proteinases (Alderete and Garza, 1988; Arroyo et al., 1992) yet, paradoxically, a cysteine-proteinase activity is required for cytoadherence (Arroyo and Alderete, 1989). Finally, the adhesins appear to be immunorecessive, as evidenced by the difficulty of generating high-titered antiserum and monoclonal antibodies (mAbs) in experimental animals (Alderete and Garza, 1988; Arroyo et al., 1992; 1993; Lehker et al., 1991).

Actual numbers of female patients infected with *Trichomonas vaginalis* within the United States are unknown, although estimates range from 4 million to as high as 10 million. Unfortunately, fifty percent of women with trichomoniasis will not be diagnosed using the standard procedure of wet-mount detection. Alternative immunodiagnostic assays and culturing of the parasite from patient vaginal washes are ineffective or too expensive and time-consuming.

Rubino et al., 1991 have reported a 2.3 kb DNA probe isolated by HindIII digestion of total *T. vaginalis* DNA that recognizes *T. vaginalis, Pentatrichomonas hominis* and *Trichomonas foetus*. This probe, as reported, was still in preliminary stages of development, and the authors indicate that this probe is not suitable as a routine diagnostic tool. Thus, at the present time, no rapid, sensitive and accurate test is available for detection of *T. vaginalis* in human fluids, especially among individuals who represent a reservoir for this parasite because of lack of diagnosis and/or treatment. Relationships between this parasite and other STD agents, including HIV and gonorrhea, have also been established, indicating a need for increased epidemiology and surveillance among susceptible individuals. There exists, therefore, an immediate need for a method of quickly identifying patients with trichomoniasis by developing assays utilizing parasite surface proteins or nucleic acids. In addition, there is a need for preventing or controlling infection, by interfering with the adhesins mediating cytoadherence of these parasites to the vaginal epithelium.

SUMMARY OF THE INVENTION

The present invention seeks to overcome these and other drawbacks inherent in the prior art by providing isolated nucleic acid segments encoding *Trichomonas vaginalis* adhesin proteins. The *Trichomonas vaginalis* adhesin proteins have been defined by a variety of established criteria. The four proteins were designated AP65, AP51, AP33 and AP23 because of their relative electrophoretic mobilities to known standards on sodium dodecylsulfate-polyacrylamide gel electrophoresis (SDS-PAGE). The proteins reside on the parasite surface and can be removed by treatment of live organisms with a protease, such as trypsin. This treatment also results in abolishment of parasite attachment to epithelial cells. Regeneration of the proteins and placement of the proteins back on the trichomonal surface restores the ability of organisms to cytoadhere. Polyclonal, monospecific antiserum to each of the proteins, when added to live parasites, reacted to the respective adhesin protein, as shown by indirect immunofluorescence. Importantly, pretreatment of live organisms blocked the recognition and binding of trichomonads to epithelial cells. No immuno-crossreactivity was detected among the four adhesins. Furthermore, peptide mapping analysis revealed that the four adhesins were distinct proteins encoded by different genes. The function as adhesins was further demonstrated by the specific binding of the proteins to the surface of epithelial cells, a procedure referred to as the ligand assay.

It is understood that the four *Trichomonas vaginalis* adhesin proteins are grouped according to the relative molecular weight ($M_r$) into four groups, AP65 (65-kDa), AP51 (51-kDa), AP33 (33-kDa) and AP23 (23-kDa). However, a part of the present discovery is the existence of a plurality of proteins with distinct sequences that comprise at least three of the adhesin families and possibly all four. Therefore, each respective adhesin is a member of a multi-gene family, and, as used herein, the terms AP65, AP51, AP33 and AP23 will designate all members of the $M_r$ *Trichomonas vaginalis* adhesin proteins as understood at the time of the present disclosure, and the members of those families of adhesins as further identified and characterized by the use of the sequences and methods disclosed herein.

The isolated nucleic acid segments of the present invention may encode an AP65 adhesin, preferably AP65-1, AP65-2 or AP65-3, or they may encode an AP51 adhesin, or they may encode an AP33 adhesin, preferably AP33-1, AP33-2 or AP33-3.

The nucleic acid segments of the present discovery may also be characterized as comprising those nucleic acid sequences, or their complements, disclosed herein and designated as SEQ ID NO:1 (AP65-1), SEQ ID NO:3 (AP65-2), and SEQ ID NO:5 (AP65-3); SEQ ID NO:7 (AP51); SEQ ID NO:9 (AP33-1), SEQ ID NO:11 (AP33-2), and SEQ ID NO:13 (AP33-3).

The complement of a nucleic acid sequence is well known in the art and is based on the anti-parallel, Watson-Crick pairing of nucleotides (bases) for a given nucleic acid polymer (strand). Two complementary strands of DNA are formed into a duplex by pairing of bases, e.g. "G" to "C", "C" to "G", "A" to "T" (in the case of DNA) or "U" (in the case of RNA) and all "T" or "U" to "A", in reverse 5' to 3' orientation (anti-parallel). As used herein therefore, the term "complement" defines a second strand of nucleic acid which will hybridize to a first strand of nucleic acid to form a duplex molecule in which base pairs are matched as G:C, C:G, A:T/U or T/U:A.

A complement may also be described as a fragment of DNA (nucleic acid segment) or a synthesized single stranded oligomer that may contain small mismatches or gaps when hybridized to its complement, but that is able to hybridize to the complementary DNA under high stringency conditions. To hybridize is understood to mean the forming of a double stranded molecule or a molecule with partial double stranded nature. High stringency conditions are those that allow hybridization between two homologous nucleic acid sequences, but precludes hybridization of random sequences. For example, hybridization at low temperature and/or high ionic strength is termed low stringency. Hybridization at high temperature and/or low ionic strength is termed high stringency. Low stringency is generally performed at 0.15M to 0.9M NaCl at a temperature range of 20° C. to 50° C. High stringency is generally performed at 0.02M to 0.15M NaCl at a temperature range of 50° C. to 70° C. It is understood that the temperature and ionic strength of a desired stringency are determined in part by the length of the particular probe, the length and base content of the target sequences, and to the presence of formamide, tetramethylammonium chloride or other solvents in the hybridization mixture. It is also understood that these ranges are mentioned by way of example only, and that the desired stringency for a particular hybridization reaction is often determined empirically by comparison to positive and negative controls.

Equations have been derived to relate duplex formation to the major variables of temperature, salt concentration, nucleic acid strand length and composition, and formamide concentration.

Eg
1. Tm=81.5−16.6(log[Na$^+$])+0.41(% GC)−600/N (Tm= temperature for duplex to half denature; N=chain length; % GC=percentage of G:C base pairings)
2. Tm=81.5−16.6(log[Na$^+$]+0.41(% GC)−0.63(% formamide)−600/N One can thus predict whether hybridization will occur under a given set of conditions.

In addition, Wood et al., 1985, (incorporated herein by reference) reported a method of hybridization screening, utilizing tetramethylammonium chloride rather than sodium chloride, that eliminates the preferential binding of G:C pairs over A:T pairs, so that hybridization stringency is dependent on probe length alone. For example, washing with 3.0M Me$_4$NCl, a single internal mismatch in a 17 base probe is reported to lower the Tm by 5–10° C. Under theses conditions, a high stringency temperature would be as low as 45° C.

A nucleic acid sequence will hybridize with a complementary nucleic acid sequence under high stringency conditions even though some mismatches may be present, particularly in complementary stretches of more than about 15 bases. Such closely matched, but not perfectly complementary sequences are also encompassed by the present invention. For example, differences may occur in nucleic acid sequences that encode the same or essentially the same polypeptide, through genetic code degeneracy, or by naturally occurring or man-made mutations, and such mismatched sequences would still be encompassed by the present claimed invention. It is also understood that the nucleic acid segments of the present invention may be defined as having the nucleic acid sequences as disclosed herein and as identified above (AP65-1, SEQ ID NO:1, AP65-2, SEQ ID NO:3 and AP65-3, SEQ ID NO.5 for the AP65 adhesin genes; SEQ ID NO:7 for the available AP51 adhesin gene; and SEQ ID NO:9, AP33-1, SEQ ID NO:11, AP33-2, and SEQ ID NO:13, AP33-3 for the AP33 adhesin genes).

Certain embodiments of the present invention will utilize nucleic acid segments that do not encode the full length adhesin protein. Such segments may encode a certain region of the adhesin protein, such as a transmembrane domain, a cytosolic region, an extracellular domain, dinucleotide-binding domains, one or several peptide sequences that elicit antibody (epitopes), and one or several peptide sequences that recognize the molecule on the epithelial cells and mediate cytoadherence (receptor-binding epitope). Such receptor-binding epitope is derived from an extracellular domain. Certain nucleic acid segments will also be useful as probes to identify other nucleic acid molecules that encode homologous or related sequences to the novel sequences disclosed herein. Certain nucleic acid segments disclosed herein will also be useful as primers for DNA or RNA polymerases, including the use of the polymerase chain reaction (PCR) to amplify a nucleic acid segment of interest. This idea forms the basis of molecular diagnosis of the disease caused by this parasite through detection of specific sequences unique to this organism.

As such, certain embodiments of the invention may be defined as an isolated nucleic acid segment comprising a sequence region that consists of at least a 14 nucleotide long contiguous sequence that has the same sequence as, or is complementary to, a 14 nucleotide long contiguous sequence of SEQ ID NO:1, SEQ ID NO:3, SEQ ID NO:5, SEQ ID NO:7, SEQ ID NO:9, SEQ ID NO:11 or SEQ ID NO:13. Alternatively, certain embodiments may be defined as comprising a sequence region that consists of at least a 17 nucleotide long contiguous sequence that has the same sequence as, or is complementary to, a 17 nucleotide long contiguous sequence of SEQ ID NO:1, SEQ ID NO:3, SEQ ID NO:5, SEQ ID NO:7, SEQ ID NO:9, SEQ ID NO:11 or SEQ ID NO:13.

Certain embodiments of the invention may be defined as comprising a sequence region that consists of at least a 20 nucleotide long contiguous sequence that has the same sequence as, or is complementary to, a 20 nucleotide long contiguous sequence of SEQ ID NO:1, SEQ ID NO:3, SEQ ID NO:5, SEQ ID NO:7, SEQ ID NO:9, SEQ ID NO:11 or SEQ ID NO:13, or even as comprising a sequence region that consists of at least a 30 nucleotide long contiguous sequence that has the same sequence as, or is complementary to, a 30 nucleotide long contiguous sequence of SEQ ID NO:1, SEQ ID NO:3, SEQ ID NO:5, SEQ ID NO:7, SEQ ID NO:9, SEQ ID NO:11 or SEQ ID NO:13. The invention may also be described in certain embodiments as comprising a sequence region that consists of at least a 50 nucleotide long contiguous sequence that has the same sequence as, or is complementary to, a 50 nucleotide long contiguous sequence of SEQ ID NO:1, SEQ ID NO:3, SEQ ID NO:5, SEQ ID NO:7, SEQ ID NO:9, SEQ ID NO:11 or SEQ ID NO:13, or as comprising a sequence region that consists of at least a 75 nucleotide long contiguous sequence that has the same sequence as, or is complementary to, a 75 nucleotide long contiguous sequence of SEQ ID NO:1, SEQ ID NO:3, SEQ ID NO:5, SEQ ID NO:7, SEQ ID NO:9, SEQ ID NO:11 or SEQ ID NO:13.

Alternatively, certain embodiments of the invention may be described as comprising a sequence region that consists of at least a 100 nucleotide long contiguous sequence that has the same sequence as, or is complementary to, a 100 nucleotide long contiguous sequence of SEQ ID NO:1, SEQ ID NO:3, SEQ ID NO:5, SEQ ID NO:7, SEQ ID NO:9, SEQ ID NO:11 or SEQ ID NO:13, or as comprising a sequence region that consists of at least a 200 nucleotide long contiguous sequence that has the same sequence as, or is complementary to, a 200 nucleotide long contiguous sequence of SEQ ID NO:1, SEQ ID NO:3, SEQ ID NO:5, SEQ ID NO:7, SEQ ID NO:9, SEQ ID NO:11 or SEQ ID NO:13, or even as comprising a sequence region that consists of at least a 300 nucleotide long contiguous sequence that has the same sequence as, or is complementary to, a 300 nucleotide long contiguous sequence of SEQ ID NO:1, SEQ ID NO:3, SEQ ID NO:5, SEQ ID NO:7, SEQ ID NO:9, SEQ ID NO:11 or SEQ ID NO:13.

In certain embodiments the invention may be defined as comprising a sequence region that consists of at least a 500 nucleotide long contiguous sequence that has the same sequence as, or is complementary to, a 500 nucleotide long contiguous sequence of SEQ ID NO:1, SEQ ID NO:3, SEQ ID NO:5, SEQ ID NO:7, SEQ ID NO:9, SEQ ID NO:11 or SEQ ID NO:13. Certain embodiments of the invention may also be described as comprising a sequence region that consists of at least a 700 nucleotide long contiguous sequence that has the same sequence as, or is complementary to, a 700 nucleotide long contiguous sequence of SEQ ID NO:1, SEQ ID NO:3, SEQ ID NO:5, SEQ ID NO:7, SEQ ID NO:9, SEQ ID NO:11 or SEQ ID NO:13 or as comprising a sequence region that consists of at least a 947 nucleotide long contiguous sequence that has the same sequence as, or is complementary to, a 947 nucleotide long contiguous sequence of SEQ ID NO:1, SEQ ID NO:3, SEQ ID NO:5, SEQ ID NO:7, SEQ ID NO:9, SEQ ID NO:11 or SEQ ID NO:13.

Certain embodiments may also be defined as comprising a sequence region that consists of at least a 974 nucleotide long contiguous sequence that has the same sequence as, or is complementary to, a 974 nucleotide long contiguous sequence of SEQ ID NO:1, SEQ ID NO:3, SEQ ID NO:5, SEQ ID NO:7, SEQ ID NO:9, or SEQ ID NO:13; or as comprising a sequence region that consists of at least a 976 nucleotide long contiguous sequence that has the same sequence as, or is complementary to, a 976 nucleotide long contiguous sequence of SEQ ID NO:1, SEQ ID NO:3, SEQ ID NO:5, SEQ ID NO:7 or SEQ ID NO:9; or as comprising a sequence region that consists of at least a 1319 nucleotide long contiguous sequence that has the same sequence as, or is complementary to, a 1319 nucleotide long contiguous sequence of SEQ ID NO:1, SEQ ID NO:3, SEQ ID NO:5 or SEQ ID NO:7.

Alternatively, certain embodiments of the invention may be defined as comprising a sequence region that consists of at least a 1764 nucleotide long contiguous sequence that has the same sequence as, or is complementary to, a 1764 nucleotide long contiguous sequence of SEQ ID NO:1, SEQ ID NO:3 or SEQ ID NO:5; or as comprising a sequence region that consists of at least a 1766 nucleotide long contiguous sequence that has the same sequence as, or is complementary to, a 1766 nucleotide long contiguous sequence of SEQ ID NO:1 or SEQ ID NO:5; or even as comprising a sequence region that consists of at least a 1804 nucleotide long contiguous sequence that has the same sequence as, or is complementary to, a 1804 nucleotide long contiguous sequence of SEQ ID NO:5.

It is further understood that the optimal size of the nucleic acid segment to be used for various embodiments, i.e. as a hybridization probe or a primer for PCR, for example, will vary according to the particular application. Therefore, contiguous segments of the nucleic acid sequences disclosed herein as SEQ ID NO:1, SEQ ID NO:3, SEQ ID NO:5, SEQ ID NO:7, SEQ ID NO:9, SEQ ID NO:11 and SEQ ID NO:13 of the following lengths, 14, 15, 16, 17, 18, 19, 20, 25, 30, 35, 40, 45, 50, 55, 60, 65, 70, 75, 80, 85, 90, 95, 100, 125, 150, 175, 200, 250, 300, 350, 400, 450, 500, 550, 600, 650, 700, 750, 800, 850, 900, 950, 1000, 1100, 1200, 1300, 1400, 1500, 1600, 1700, 1800 or even 1804 bases, and all other integers from 14 to 1804, inclusive, will find uses in various applications well known in the art, and would therefore fall within the scope of the appended claims.

It is also understood that the nucleic acid segments of the present invention may be under the control of a promoter. The promoter may be the normal promoter which controls the expression of the nucleic acid segment in its native organism, or it may be a recombinant promoter. By recombinant promoter is meant a promoter derived from another source, either of procaryotic, viral, protozoan or eucaryotic origin, such as from *Escherichia coli* (procaryote) or from another trichomonad species (protozoan) or from epithelial cells (eukaryotic). The promoter sequence is then joined to the nucleic acid segment in an upstream position (5') from the start of the gene. Promoters that may be used include, but are not limited to, cytomegalovirus major immediate early gene promoter, simian virus 40 late gene promoter, baculovirus *Autographa californica* nuclear polyhedrosis virus polyhedrin gene promoter or lac promoters of *Escherichia coli*. Such promoters as exist in the commercially-available expression systems that are used for synthesis of recombinant proteins are routinely employed. Alternatively, the promoter may be a promoter that is up-regulated by iron as defined herein below.

It is understood in the art that to bring a coding sequence under the control of a promoter, one positions the 5' of the transcription initiation site of the transcriptional reading frame of the protein between about 1 and about 50 nucleotides "downstream" (i.e., 3') of the chosen promoter. The joining of such nucleic acid sequences is routinely practiced in the art and involves the cutting and isolation of nucleic acid fragments with restriction endonuclease digestion followed by joining of the appropriate nucleic acid molecules by ligation. Other methods may include the synthesis of synthetic nucleic acid fragments or the use of various polylinker fragments to join two desired nucleic acid fragments in the proper orientation. In addition, where eukaryotic expression is contemplated, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

The nucleic acid segments of the present invention may also comprise a vector capable of replicating within a cell. In particular, the nucleic acid segments may comprise a recombinant vector. A large number of vectors are available commercially and are well known to those in the art. In general, a vector is compatible with a particular cell type such as prokaryotic, eukaryotic, yeast, plant, insect, etc. The matching of compatible vectors and host cells is well known and routinely practiced in the art. The vector may comprise at least 2,000, 3,000, 5,000 or even 10,000 bases and may be further defined as comprising the nucleic acid sequence set forth in DNA sequences of the adhesins as defined herein as SEQ ID NO:1, SEQ ID NO:3, and SEQ ID NO:5 for the AP65 adhesin genes; SEQ ID NO:7 for the AP51 adhesin gene; and SEQ ID NO:9, SEQ ID NO:11 and SEQ ID NO:13 for the AP33 adhesin genes) or as a recombinant expression vector capable of expressing a *Trichomonas vaginalis* adhesin polypeptide on introduction into a host cell, such as a procaryotic organism like *Escherichia coli*. Vectors that may be used in the practice of the invention include those vectors commercially available through the company InVitrogen, which have been used for the adhesin DNAs. A preferred vector in the practice of the present invention is the pcDNAII vector.

In certain embodiments, the vector which comprises the nucleic acid segment of the present invention will be an expression vector capable of expressing an adhesin peptide or polypeptide in *Escherichia coli*. In this embodiment, the nucleic acid segment encoding the adhesin polypeptide will be transcribed into mRNA, and the mRNA will be translated into a polypeptide. Thus, the recombinant bacterium will express the adhesin polypeptide. The vector in this embodiment will comprise the promoter sequences to express the gene in the particular cell type. For instance the promoter regions, translational start and termination sequences, and any signals following the start site, such as for post-translational modifications, including polyadenylation, will be compatible with the trichomonad transcription/ translational machinery.

Certain embodiments of the present invention may be defined as a host cell comprising the nucleic acid segments disclosed herein. Such a host cell would be an engineered or recombinant cell. As used herein, the term "engineered" or "recombinant" cell is intended to refer to a cell into which a recombinant gene, such as a gene encoding an adhesin protein has been introduced. Cell refers to either a procaryote, like *Escherichia coli* that is routinely used for expression of foreign genes, or mammalian cells. Therefore, engineered cells are distinguishable from naturally occurring bacterial or mammalian cells, which do not contain a recombinant gene. Engineered cells are thus cells having a gene or genes introduced through the hand of man. Recombinant genes will either be in the form of a complementary DNA (cDNA) that is synthesized from the messenger RNA. Such cDNAs will not contain introns. Recombinant genes also can be a copy of a genomic copy of a gene derived directly from the DNA of the trichomonad, in which case the genomic DNA will include genes positioned adjacent to a promoter not naturally associated with the particular introduced gene.

Prokaryotic cells (also called hosts) may be preferred for expression of the adhesin proteins. Some examples of prokaryotic hosts are various *Escherichia coli* strains, bacilli such as *Bacillus subtilis*, or other enterobacteriaceae, such as *Salmonella typhimurium* or *Serratia marcescens*. Various Pseudomonas species may be used. Nonetheless, *E. coli* is the most commonly used.

In general, plasmid vectors containing replicon and control sequences which are derived from species compatible with the host cell are used in connection with these hosts. The vector ordinarily carries a replication site, as well as marking sequences, which are capable of providing phenotypic selection in transformed cells. For example, well known plasmids useful for transforming *E. coli* are pBR322 or the pUC series plasmids derived from an *E. coli* species. These plasmids contain genes for ampicillin and tetracycline resistance and thus provide easy means for identifying transformed cells. Alternate plasmids are derived from bacteriophage, such as λ and are commercially available.

Some promoters commonly used in recombinant DNA construction include the B-lactamase (penicillinase) and lactose promoter systems, as well as viral promoters. While these are the most commonly used, other microbial promoters have been discovered and utilized, and details concerning their nucleotide sequences are readily available, enabling a skilled worker to ligate them functionally into plasmid vectors.

Preferred cell lines to be used in the present invention are prokaryotic cells like *E. coli*. The host cell may be further defined as comprising a nucleic acid segment in accordance with adhesin DNA sequences identified herein as SEQ ID NO:1, SEQ ID NO:3, and SEQ ID NO:5 for the AP65 adhesin genes; SEQ ID NO:7 for the AP51 adhesin gene; and SEQ ID NO:9, SEQ ID NO:11 and SEQ ID NO:13 for the AP33 adhesin genes positioned in a recombinant vector. It is understood that the nucleic acid segment may also be integrated into the host genome. The host cell may be defined as comprising a recombinant expression vector and expressing a recombinant adhesin protein.

An alternate embodiment of the present invention is a promoter up-regulated by iron. By up-regulated is meant that the presence of iron will cause an enhancement in the transcription of the genes controlled by the promoter. Preferred promoter sequences will comprise a nucleic acid sequences wherein a portion of said sequence consists essentially of nucleotides 1–13 of SEQ ID NO:1, nucleotides 1–14 of SEQ ID NO:3 or nucleotides 1–13 if SEQ ID NO:5. The promoter may be contained in a plasmid, viral or any other type of vector placed upstream (5') of a multiple cloning site for easy insertion of a gene to be controlled by said promoter. Such techniques are routinely practiced in the art and would require no undue experimentation. The iron may be supplied in the culture medium, for example, and may be in the form of ions including ferrous ions, such as ferrous ammonium sulfate hexahydrate (Fe $(NH_4)_2(SO_4)_2 \cdot 6H_2O$).

The present invention may also be defined, in certain embodiments, as a recombinant *Trichomonas vaginalis* adhesin protein, and preferably an adhesin protein as defined herein as being a member of the gene family for each of the adhesins, e.g. AP65-1, AP65-2, AP65-3, AP51, AP33-1, AP33-2 and AP33-3. The recombinant proteins of the present invention may, in certain embodiments, be defined as consisting essentially of the amino acid sequence given identification numbers (SEQ ID NO:2, SEQ ID NO:4, and SEQ ID NO:6 for the AP65 adhesin gene products; SEQ ID NO:8 for the AP51 adhesin gene product; and SEQ ID NO:10, SEQ ID NO:12 and SEQ ID NO:14 for the AP33 adhesin gene products).

An embodiment of the present invention is also a method of expressing a gene, where transcription is increased by the presence of iron. The present method comprises the steps of operatively linking the gene to be expressed to a promoter capable of being regulated by iron as disclosed herein, and expressing the gene in the presence of an amount of iron sufficient to increase said transcription. A sufficient amount of iron is defined herein as being at least about 1 µM and up to a concentration of about 250 µM, with the limit being the minimum amount that can be tolerated by the trichomonas parasite. It is understood that these amounts are those determined on the basis of growth of the parasite in the complex trypticase-yeast extract-serum medium routinely used for cultivation of *T. vaginalis* isolates. The iron atom may be present in any form that will have the desired effect and is preferably ionic iron, and more preferably ferrous ammonium sulfate hexahydrate.

The present method of increasing expression of a gene in the presence of iron will be particularly useful when the gene is a reporter gene, thereby allowing one to detect the presence of iron in a sample, by comparing the levels of the various indicators produced in the sample to levels of the indicators in samples of known iron content. Preferred reporter genes include, but are not limited to a luc or lux gene, a CAT gene or a β-gal gene.

An embodiment of the present invention is also an antigenic peptide or polypeptide comprising an amino acid sequence wherein a portion of said amino acid sequence consists essentially of a contiguous sequence in accordance with SEQ ID NO:2, SEQ ID NO:4, SEQ ID NO:6, SEQ ID NO:8, SEQ ID NO:10, SEQ ID NO:12 or SEQ ID NO:14, wherein that portion of said peptide or polypeptide according to SEQ ID NO:2, SEQ ID NO:4, SEQ ID NO:6, SEQ ID NO:8, SEQ ID NO:10, SEQ ID NO:12 or SEQ ID NO:14 consists essentially of a globular or surface polypeptide as defined by a Kyte-Doolittle hydropathy plot. Such peptides also may be determined by the method of Hopp, disclosed as U.S. Pat. No. 4,554,101, incorporated herein by reference, combined with the hydrophilicity profile as demonstrated herein as FIG. 2A, FIG. 2B and FIG. 2C. It is understood in the art that such antigenic peptides may be linked to a carrier polypeptide such as bovine serum albumen or keyhole lympet cyanin. The linkage may preferably be done genetically so that the fusion is expressed from a single gene. Peptides defined by this method can be used to determine antigenic sequences that distinguish the various AP65's for example, or members of any of the families of adhesin proteins such as AP51's, AP33's and AP23's. The present invention will allow the use of antibodies directed to specific defined peptide sequences that are unique to each of the members of the adhesin family, and thus differential expression under various conditions can be determined. This will lead to the development of more sophisticated diagnosis and treatment regimens that target specific adhesins under defined physiological conditions.

An embodiment of the present invention is also a method of inhibiting *Trichomonas vaginalis* cytoadhesion comprising blocking *Trichomonas vaginalis* adhesin receptors with a recombinant adhesin polypeptide. The present method may utilize a full length adhesin polypeptide, or may utilize a fragment of an adhesin and preferably a polypeptide derived from SEQ ID NO:2, SEQ ID NO:4, SEQ ID NO:6, SEQ ID NO:8, SEQ ID NO:10, SEQ ID NO:12 or SEQ ID NO:14, wherein that portion of said peptide or polypeptide derived from SEQ ID NO:2, SEQ ID NO:4, SEQ ID NO:6, SEQ ID NO:8, SEQ ID NO:10, SEQ ID NO:12 or SEQ ID NO:14 consists essentially of a globular or surface polypeptide as defined by a Kyte-Doolittle hydropathy plot.

BRIEF DESCRIPTION OF THE DRAWINGS

FIG. 1A. Restriction maps of cDNAs encoding recombinant proteins immunoreactive with antiserum to the AP65 adhesin.

FIG. 1B. Restriction map of cDNA encoding recombinant protein immunoreactive with antiserum to AP51 adhesin.

DETAILED DESCRIPTION OF THE PREFERRED EMBODIMENTS

Figure 1C:
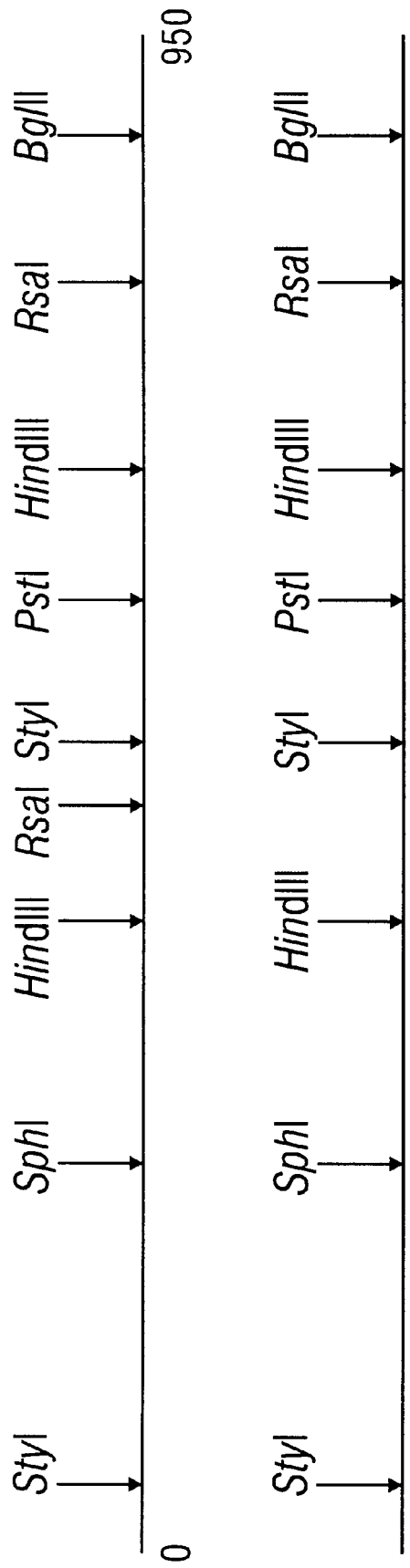
FIG. 1C. Restriction maps of cDNAs encoding recombinant proteins immunoreactive with antiserum to the AP33 adhesin.

The discovery of genetically distinct genes encoding alternate forms within the various families of Trichomonas vaginalis adhesin proteins represents an unexpected advancement in the diagnosis, treatment and prevention of this important disease. Rather than just four adhesins, disclosed herein are 3 distinct AP65 adhesins and 3 AP33 adhesins in addition to AP51 and AP23. It is contemplated that, in light of the present disclosure, the four previously known sizes of adhesins may each comprise a family of adhesin proteins. The discovery of the nucleic acid and amino acid sequences of these previously unknown adhesins will have important implications in the development of therapeutic and preventative agents of this important sexually transmitted disease.

Because previous data had shown that iron up-regulates expression of trichomonad adhesins (Lehker et al., 1991), mRNA derived from a T. vaginalis fresh isolate grown in high-iron conditions was used to make the library of cDNAs from which the cDNAs having sequences disclosed herein were obtained. The four adhesins are coordinately regulated (Arroyo et al., 1992; Lehker et al., 1991) and, therefore, were expected to be represented in the cDNA library. Nonetheless, clones encoding for the AP23 adhesin were not detected during immuno-screening. Given the reported difficulties in immunoblot detection of AP23 (Arroyo et al., 1992), the solubilization and blotting conditions may have resulted in denaturation and absence of epitope recognition on the recombinant colonies.

The isolated cDNAs encode for proteins which fulfilled the functional and immuno-crossreactive criteria expected of the individual trichomonad adhesins (Arroyo et al., 1992). Although adhesins do not elicit high-titered antibody in rabbits immunized with parasites (Alderete and Garza, 1988), antibody to the recombinant E. coli colonies was detected in the antiserum and could be purified from the antiserum. This purified antibody from rabbit antiserum to total trichomonad proteins was immuno-crossreactive between recombinant proteins and the parasite adhesins, as were monospecific antisera and mAbs previously generated (Arroyo et al., 1992). This immuno-crossreactivity reaffirmed that these cDNAs encoded the trichomonad adhesins.

Surprisingly, initial restriction analysis gave different maps for three AP65 cDNA clones, making it essential to fully characterize the three cDNAs. Further mapping and Southern analysis indicated that distinct genes, now called ap65-1, ap65-2 and ap65-3, encoded the previously described AP65 adhesin of T. vaginalis (Arroyo et al., 1992). Further, analysis showed also that each of the AP65 genes was multicopy. Northern analysis detected the presence of a transcript of expected size for each of the genes. Importantly, only when RNA was isolated from trichomonads grown in high-iron-medium was transcription evident, confirming earlier findings on the up-regulation of adhesin gene expression by iron (Lehker et al., 1991).

The discovery that recombinant AP65 proteins bound to HeLa cells allowed the demonstration of competition between recombinant AP proteins with trichomonad adhesins for host cell surfaces. This latter result shows that each recombinant adhesin AP65 encodes a receptor-recognition site, a finding important for epitope mapping of the functional receptor-binding domain of the recombinant proteins. It is contemplated that each of the AP65 adhesins may interact with the same receptor or with different receptors. Nonetheless, the existence of at least one such receptor has been shown (Arroyo et al., 1992).

The availability of recombinant adhesins and the corresponding cDNAs will be important for the development of diagnostic and therapeutic applications. For example, since a cysteine proteinase activity is needed for cytoadherence action (Arroyo and Alderete, 1989), the conditions necessary for proteinase activity can be determined. It is noteworthy that the recombinant adhesins have no detectable proteinase activity. However, it is important to recognize that the absence of proteinase activity of the recombinant proteins in the studies disclosed herein may be due to the use of an inappropriate substrate. Alternatively, the activation pH of the cysteine proteinase assay (Neale and Alderete, 1990) is not the pH at which optimal cytoadherence occurs (Alderete and Garza, 1985). Nonetheless, under these conditions, the recombinant proteins and trichomonad adhesins as presented here, do not represent any of the proteinases that have been previously identified (Neale and Alderete, 1990). Having recombinant proteins and cDNAs also allowed the confirmation that the adhesins are distinct gene products, as evidenced by the absence of any immuno-crossreactivity between the recombinant adhesins and by the lack of hybridization among the cDNAs. The relative importance of each adhesin to one another in cytoadherence may now be determined.

Southern analysis confirmed that the three AP65 cDNAs are distinct and are present in the genome of T. vaginalis. An example of how this was done is the following: Three restriction enzymes (PmaCI, SacII and XcmI) were chosen to generate specific internal fragments of two AP65 cDNAs designated as F11.2 and F11.5. Two fragments, designated a and b, were F11.2-specific, and two other fragments, c and d, were F11.5-specific, based on size differences and intensities of hybridization with respective probes. After electrophoresis in 1% agarose and blotting, the presence of fragments was demonstrated by hybridization of duplicate blots with respective $^{32}$P-labeled F11.2 (probe 1) and $^{32}$P-labeled F11.5 (probe 2). The presence of the fragments was also shown by Southern analysis of 5 μg purified genomic DNA of T. vaginalis T016N digested with the endonucleases. Fragment a was detected only in the PmaCI-digested DNA while fragment d appeared in the XcmI-treated DNA. Both b and c were seen in the hybridization patterns of SacII-digested DNA.

That two distinct genes encoding AP65, now called AP65-1 and AP65-2, are present within the genome and each in multiple copies was verified by using highly specific, non-crosshybridizing PCR products generated to the 5' ends of both F11.2 (AP65-1) and F11.5 (AP65-2) cDNAs. The 5'-end specific probes gave patterns in Southern analysis that reinforced the multicopy nature for each AP65 gene. The data disclosed herein also suggest that the genes encoding all three adhesin families are multicopy. Similar studies were performed with F11.1 cDNA (AP65-3) to show its distinctness from AP65-1 and AP65-2.

Iron is clearly an important signal to T. vaginalis (Lehker and Alderete, 1992), and iron-limited organisms provided with iron increase transcription and synthesis of adhesins (Lehker et al., 1991). In addition, immediately after contact with host cells the parasites undergo a dramatic morphological transformation concomitant with the rapid synthesis of adhesins (Arroyo et al., 1993). Without limiting the discovery to any single theory, it is contemplated that the presence of multiple copies of AP65 genes as well as the other adhesin gene families may ensure the expression and synthesis of adequate amounts of adhesins within a short period of time following contact. Also possible is that the different AP65 genes, although coordinately regulated by iron, respond to yet other undefined environmental signals. It is contemplated, for example, that the genes for each of the three AP65s, but not all three, are directly involved in transcription and expression of the adhesin following contact with the epithelial cell surface (Arroyo et al., 1993). The other gene(s) may be responsive at times other than contact, for instance when different amounts and types of iron sources are available in the vagina, such as during menstruation. Alternatively, adhesin gene expression may be under the control of different, and even multiple, signal pathways. In this scenario, it is envisioned that iron utilization coupled with other signals like pH, receptor density, and medium depletion, mediate the expression of one but not all of the ap65 genes. The present discovery of the cDNAs encoding this important family of genes will allow the clarification of whether the products of the entire families of genes, transcribed coordinately, are translated and expressed on the surface. This will be possible because the present discovery allows the generation of specific antibodies which distinguish between the various adhesins within the family groups.

The deduced amino acid sequences for the AP65 genes and proteins contain a putative leader peptide that shows similarity to the signal sequences of mitochondrial and hydrogenosomal proteins (Lahti et al., 1992; von Heijne et al., 1989). This signal sequence does not appear to be typical of proteins translocated to the membrane (von Heijne, 1986). It is possible however, that this signal, although shorter, is capable of directing the adhesin to the plasma membrane. Since several surface and exported proteins from other organisms also do not have typical N-terminal signal peptides (Lottenberg et al., 1992; Joe et al., 1994), the hydrophobic carboxyl terminus of the AP65 adhesins may play a role in localizing the molecule to the T. vaginalis surface. Alternatively, taking into account that T. vaginalis has four families of adhesins that are coordinately expressed, one might envision that all four types of proteins are placed within a vesicle and exported in this manner. This possibility would allow for efficient simultaneous localization of the four adhesin families, each of which was found essential for cytoadherence (Alderete and Garza, 1985; 1988a; Arroyo, et al., 1992).

Malic Enzyme

A database search for homologous proteins of the AP65 adhesins revealed significant sequence similarity to malic enzymes (38% at the amino acid level and 54% at the nucleotide level) isolated from a variety of sources. Malic enzyme found in T. vaginalis hydrogenosomes normally functions as a metabolic enzyme catalyzing the oxidative carboxylation of malate to pyruvate. It has not been possible to test whether the any of the AP65 recombinant protein adhesins express malic enzyme activity because of the low levels and degradation of recombinant proteins in E. coli. This will be possible in light of the present discovery, as the generation of antibodies specific for each adhesin which do not crossreact with malic enzyme are now possible. Such an antibody reagent will be useful for enrichment, such as by affinity chromatography, of the individual adhesins to allow the performance of malic enzyme assays and other studies, such as localization of the molecules within the parasite.

Malic enzyme is widely distributed among plants, bacteria and animals and has a variety of metabolic roles. It has been found in several forms, including cytoplasmic, mitochondrial and interestingly, membrane-bound (Kendrick and Ratledge, 1992). In some instances, the location of a protein may play a role in its function. One way of regulating protein structure and its function is via ADP-ribosylation (Pancholi and Fischetti, 1993). In the case of GAPDH, the surface form of the enzyme, but not the cytosolic form, is capable of auto-ADP-ribosylation (Pancholi and Fischetti, 1993). This process decreased enzymatic activity without affecting the binding properties of the surface enzyme. The cytosolic form remained catalytic without ADP-ribosylation. It is contemplated that this mechanism may exist in the malic enzyme-like adhesin proteins.

The present data does not exclude the possibility that one of the AP65 proteins represents the bona fide trichomonad malic enzyme. AP65-1, AP65-2 and AP65-3 share with malic enzymes 3 putative dinucleotide-binding domains, the malic enzyme manganese-binding sequence, and the residue believed to be the malate-binding site. Nevertheless, neither purified, commercially-available malic enzyme nor extracts of control E. coli containing malic enzyme interfered with T. vaginalis cytoadherence to host cells, showing a lack of involvement of the enzyme domains as an adhesin. Furthermore, purified malic enzyme did not prevent binding of the trichomonad AP65 to fixed HeLa cells in the ligand assay. Equally noteworthy, a mAb immuno-crossreactive between the adhesins and malic enzyme also failed to inhibit T. vaginalis cytoadherence. These data suggest strongly and support the view that, regardless of whether the adhesins possess malic enzyme-like domains, the receptor-binding epitope(s) for the AP65 adhesins is specific and unique from malic enzymes.

Furthermore, because of the highly conserved nature of malic enzymes and the malic enzyme sequences in the adhesins, the placement of host-like proteins on the surface of this sexually transmitted agent may be significant and play a role in immune evasion. This would represent a form of molecular mimicry, something receiving attention as an important mechanism by which parasites escape recognition by the host immune system (Damian 1989). The immunorecessive nature of the adhesins has previously been reported by the present inventors and preliminary data suggest that the AP65 adhesin is not detected in human serum or vaginal wash. This strategy by the parasite has important implications for vaccine development using biofunctional trichomonad molecules, such as adhesins, which mimic host proteins. Future identification of the receptor-binding epitope, now possible in light of the present disclosure, and the extent of commonality of this epitope with host sequences will be important in the development of these proteins as vaccine candidates.

AP65 Adhesins Appear Unique to *T. vaginalis*

In order to determine whether the AP65 adhesins and genes of *T. vaginalis* were present within the genome of other *trichomonad* species (*Trichomonas suis*-the porcine *trichomonad*, *Tritrichomonas foetus*-the bovine trichomonad, and *Pentatrichomonas hominus*-the intestinal trichomonad of humans), a ligand assay was performed simultaneously with a cross-hybridization study using the cDNA inserts as probes. As a control for the hybridization study, duplicate gels of DNA were stained with ethidium bromide after electrophoresis to ensure identical amounts of DNA in each lane. Total undigested DNA, purified similarly for all species, was electrophoresed and blotted. Only *T. vaginalis* genomic DNA gave a reaction, with a hybridizing band detected with the adhesin cDNAs, when compared with equal amounts of undigested genomic DNA of *P. hominis*, *T. suis*, and *T. foetus*. These results were seen at varying levels of stringency. The absence of any AP65-like proteins in the other species was further demonstrated by the lack of detection in immunoblots of proteins that bound to HeLa cells. Using antisera to the polyclonal rabbit anti-AP65 adhesin serum, only the adhesins were detected readily for *T. vaginalis*. Under no circumstances were proteins immuno-crossreactive with anti-AP65 serum detected for the other species, even when 10-fold greater amounts of extracts were used in the ligand assay for blotting with anti-AP65 antiserum.

Methodology

Microorganisms and culture conditions

*Trichomonas vaginalis* isolate T016N was a fresh clinical isolate that expressed high amounts of adhesins under iron-replete growth conditions (Arroyo et al., 1993; Lehker et al., 1991). The growth medium of Trypticase-yeast extract-maltose with 10% heat-inactivated horse serum (Diamond, 1957) was supplemented with 250 $\mu$M ferrous ammonium sulfate-hexahydrate (Sigma Chemical Co., St. Louis, Mo.), which was prepared as a 100-fold stock solution made in 50 mM sulfosalicylic acid (Lehker et al., 1991). *T. vaginalis* organisms of other fresh isolates that were used for all studies were grown to the late-logarithmic-phase of growth.

Recombinant *Escherichia coli* INV$\alpha$F' (Invitrogen Corp., San Diego, Calif.) harboring the phagemid vector pcDNAII (Invitrogen) with the cDNA clones F11.2 or F11.5, which encode for AP65 adhesins were cultured in Luria-Bertani (LB) broth or LB agar plates (Sambrook et al., 1989) with 60 $\mu$g/ml ampicillin (Sambrook et al., 1989). Also used as a host cell for recombinant plasmids containing cDNAs was *Escherichia coli* strain HB101.

Nucleic acid isolation of *T. vaginalis*

Total RNA from high-iron-grown parasites was isolated by the procedure of Chomczynski and Sacchi (1987), incorporated herein by reference, using acid phenol. In the preferred procedure, $10^8$ parasites were washed and immediately lysed by addition of solution D (4M guanidinium thiocyanate, 25 mM sodium citrate, pH 7.0, 0.5% sarcosyl and 100 mM 2-mercaptoethanol). Then, 2M sodium acetate, pH 4.0, acid phenol, and a chloroform-isoamyl alcohol mixture were added sequentially (Chomczynski and Sacchi, 1987) and the lysate mixed by inversion after each addition. The final suspension was shaken vigorously for 10 sec and cooled on ice for 15 min. Samples were centrifuged at 10,000×g for 20 min at 4° C. After centrifugation, RNA in the aqueous phase was precipitated by ethanol. The RNA pellet was dissolved in solution D, re-precipitated and rinsed by ethanol before dissolving in 0.5% sodium dodecyl sulfate (SDS) at 65° C. for 10 min. RNA was stored at −70° C. The mRNA was purified with oligo (dT)-cellulose type 7 (Pharmacia LKB Biotechnology, Alameda, Calif.).

Total genomic DNA from trichomonads was isolated by standard procedures. In the preferred procedure, $10^8$ parasites were lysed with 0.2% SDS in buffer consisting of 100 mM NaCl, 10 mM ethylene diaminetetraacetic acid (EDTA) and 10 mM Tris-HCl, pH 8.0 before extracting four times with a phenol-chloroform mixture. After extraction two additional times with chloroform, DNA was precipitated by ethanol. The DNA pellet was resuspended and incubated in TE buffer (1 mM EDTA and 10 mM Tris-HCl, pH 8.0) containing 200 $\mu$g per ml of RNase A for 10 min at 37° C. Then, proteinase K (100 $\mu$g per ml final concentration) was added prior to incubation for 45 min at 37° C. DNA was phenol-chloroform extracted and precipitated again by ethanol and dissolved in TE buffer for storage at 4° C.

Generation and isolation of cDNAs

A *T. vaginalis* cDNA expression library was constructed for directional cloning into the pcDNAII phagemid vector, as recommended by the manufacturer (InVitrogen). Recombinant colonies were screened (Sambrook et al., 1989) with rabbit antiserum and mAb raised against the purified adhesins (Arroyo et al., 1992; 1993; Lehker et al., 1991). Antiserum was adsorbed with *E. coli* lysate before screening. Ten cDNAs obtained from immunoreactive colonies were isolated and purified (Table 2). Recombinant plasmids were recovered by alkaline lysis (InVitrogen) as recommended by the manufacturer. Insert analysis was performed by treatment of plasmids with XmaIII and subsequent electrophoresis of DNA on 1% agarose gels in TAE buffer (1 mM EDTA in 40 mM Tris-acetate, pH 8.0) (Sambrook et al., 1989).

DNA Sequencing and Analysis

DNA sequencing was performed by the dideoxy chain termination method using the Sequenase 2.0 DNA Sequencing kit (United States Biochemical, Cleveland, Ohio) as recommended by the manufacturer. Sequence information was obtained by stepwise sequencing. Initially, universal and reverse M13 primers (Promega, Madison, Wis.) were used. As new sequence data became available, cDNA specific oligonucleotides were synthesized (U.T.H.S.C. Center for Advanced DNA Technologies, San Antonio, Tex. and Genosys Biotechnologies, The Woodlands, Tex.) and utilized to continue the sequence determination. Both strands of the cDNA were sequenced at least 3 times. Any problem areas or compressions were resolved by substituting 7-deaza-dGTP or dITP for dGTP. Computer analysis of the sequence was carried out using PC/GENE (Release 6.8) (IntelliGenetics, Inc., Mountain View, Calif.).

Rapid amplification of F11.2 and F11.5 cDNAs 5' ends (RACE)

The 5'-ampliFINDER RACE kit (Clontech Lab, Inc., Palo Alto, Calif.) was used as recommended by the manufacturer to generate highly specific probes for differentiation of the adhesin genes. Partially purified mRNA (5 $\mu$g) was used for first-strand cDNA synthesis, which was performed by priming the RNA with an oligo (P1) common for both F11.2 and F11.5 cDNA clones. The oligo P1 represented AP65 antisense nucleotides with the sequence 5'-GCGGATACGAGCAGCTTGTTCATCC-3', SEQ ID NO:15. An anchor with an EcoRI restriction site (Clontech) was then ligated to the first strand cDNA. Amplification was then performed using the anchor primer (Clontech) and the second oligo (P2) representing the internal AP65 antisense sequence of F11.2 containing two internal EcoRI sites (5'-GAATTCGAATTCGAGGAGGCCACGAAGATTGAA GCGG-3', SEQ ID NO:16) and of F11.5 without EcoRI sites (5'-CTCCTTTGTGAAGGCAGAACCC-3', SEQ ID NO:17). Using the P2 primers, the F11.2- and F11.5-specific cDNA sequences were amplified during 35 cycles of the polymerase chain reaction (PCR) at 94° C. for 45 sec, 60° C. for 45 sec, and 72° C. for 2 min, with a final extension time of 7 min (Clontech). The amplified products were analyzed on Metaphor agarose gels (FMC BioProducts, Rockland, Md.) and subcloned directly into pCRII (Invitrogen) . The existence of primer sequences and F11.2- and F11.5-specific sequences was confirmed by cross-hybridization of PCR products. The PCR products were sequenced, both strands, $\geq 3$ times using universal M13 primers and sequence-specific oligonucleotides.

Southern and Northern analysis

For Southern analysis, cDNA or trichomonad genomic DNA digested with specific restriction enzymes was transferred to a Zeta-probe membrane (Bio-Rad Laboratories, Richmond, Calif.) as recommended by the manufacturer. Hybridizations were carried out with purified, representative nick-translated cDNA inserts used as probes (Sambrook et al., 1989). Blots were first treated in prehybridization solution (50% formamide, 120 mM Na$_2$HPO$_4$, 250 mM NaCl, 7% SDS and 1 mM EDTA) at 42° C. Radiolabeled probes were then added to new prehybridization solution and incubated with the blots for 18 h at 42° C. Filters were then sequentially washed with 2×SSC (1×SSC is 150 mM NaCl and 15 mM Na$_3$citrate, pH 7.0)-0.1% SDS, 0.5×SSC-0.1% SDS and 0.1×SSC-0.1% SDS at 42° C. for 30 min each wash. Blots were then exposed to Kodak XRP-5 X-ray film.

Transcripts were detected by performing Northern blot analysis of electrophoresed total trichomonad RNA on 1% agarose in 2M formaldehyde gels (Sambrook et al., 1989) that was transferred to a Zeta-probe membrane (Bio-Rad). Blots were probed with nick-translated cDNA inserts from each adhesin. Hybridization reactions were performed as for Southern analysis and as previously described before (Khoshnan and Alderete, 1993, incorporated herein by reference).

SDS-polyacrylamide gel electrophoresis (PAGE) and immunoblotting of recombinant proteins One milliliter of overnight (o/n) cultures of recombinant E. coli was pelleted and suspended in 200 μl of electrophoresis sample buffer (Laemmli, 1970) and boiled for 3 min (Sambrook et al., 1989). Aliquots of 10 μl of recombinant E. coli lysates were subjected to SDS-PAGE using 10% separating and 4% stacking gels (Alderete and Garza, 1985). Following electrophoresis, gels were stained with Coomassie brilliant blue. Duplicate gels were transferred to nitrocellulose (NC) for immunoblotting (Towbin et al., 1979).

The NC blots were rinsed with TNT buffer (100 mM Tris-HCl, pH 7.4, 150 mM NaCl and 0.05% Tween 20) and blocked with TNT buffer containing 5% skim milk (BLOTTO) for 1 h at RT (Sambrook et al., 1989). The filters were incubated with rabbit anti-adhesin serum diluted 1:50 in BLOTTO for 18 h at 4° C. followed by five washings in TNT buffer for 5 min each. The filters were then incubated at RT for 1 h with alkaline phosphatase-conjugated goat anti-rabbit IgG (Bio-Rad) diluted 1:4000 in TNT buffer-3% skim milk. Studies were performed similarly with mAb F11 reactive to AP65, in which case alkaline phosphatase-conjugated goat anti-mouse IgG (Bio-Rad) diluted 1:4000 was used. As negative controls, prebleed rabbit serum diluted 1:50 in BLOTTO or undiluted culture supernatant from the NS-1 cloned mouse myeloma cell (ATCC) was used. After incubation, the filters were washed five times with TNT buffer. Color development was observed upon incubation in alkaline phosphatase buffer (100 mM Tris-HCl, pH 9.5, 100 mM NaCl, and 5 mM MgCl$_2$) with nitroblue tetrazolium and 5-bromo-4-chloro-3-indolyl phosphate (both from Sigma). The reaction was stopped with 20 mM EDTA in PBS (Harlow, 1988).

Preparation of French press E. coli extracts

Recombinant E. coli single colonies grown o/n at 37° C. in 50 ml LB broth-ampicillin cultures were harvested, washed once, and resuspended to one-tenth the original volume in cold 10 mM N-2-hydroxyethylpiperazine-N'-2 ethanesulfonic acid (HEPES), pH 7.4, and kept at 4° C. The suspension was passed through a French pressure cell at 1260 psi in three separate cycles to lyse the bacteria. The lysate was centrifuged at 4,300×g for 10 min to remove intact bacteria and large debris. The concentration of protein in each lysate was ~2 mg/ml as calculated using the BCA Protein Assay (Pierce, Rockford, Ill.). This clarified bacterial lysate was used for the ligand assay as described below.

The ligand assay

French press bacterial lysate (1 ml) was incubated with $10^6$ fixed HeLa cells for 18 h at 4° C. followed by washing five times with TDSET buffer [10 mM Tris-HCl, pH 7.0, 0.2% sodium deoxycholate (DOC), 0.1% SDS, 10 mM EDTA and 1% Triton X-100]. Fixed host cells were prepared as previously described (Alderete and Garza, 1985; 1988; Arroyo et al., 1992, all incorporated herein by reference). Bacterial proteins avidly bound to fixed HeLa cells were eluted by boiling in electrophoresis sample buffer (Arroyo et al., 1992) for 3 min. After SDS-PAGE, proteins were blotted onto NC for detection with adhesin antiserum or mAb (Arroyo et al., 1992; Lehker et al., 1991).

To further show that the recombinant proteins were the parasite adhesins, a competition study was performed. In this case, lysates of parasites metabolically labeled for 20 h at 37° C. with EXPRE$^{35}$S$^{35}$S-Protein labeling mix (sp act. 37.0 TBq)/mmol) (Du Pont, NEN Research Products, Boston, Mass.) (2.5 mCi per 50 ml of culture medium) were prepared as described (Arroyo et al., 1992; Lehker et al., 1991, incorporated herein by reference). In this procedure, $2 \times 10^7$ radiolabeled trichomonads were suspended in 500 μl NET buffer (50 mM Tris-HCl, pH 7.4, 50 mM NaCl and 5 mM EDTA) containing 1 mM N-α-p-tosyl-L-lysine chloromethyl ketone (TLCK) (Sigma) and 100 μg/ml leupeptin (Sigma). Trichomonads were incubated in buffer with inhibitors for 10 min on ice before lysing with 1% DOC (Sigma). After 20 min on ice, the extract was vortexed for 1 min. TDSET buffer with proteinase inhibitors was then added to a 1 ml volume. The suspension was vortexed and then clarified by centrifugation over a sucrose cushion at 14,000×g for 30 min at 4° C. (Arroyo et al., 1992; Lehker et al., 1991).

Glutaraldehyde-stabilized HeLa cells ($10^6$) were first treated with different amounts of recombinant bacterial lysate for 18 h at 4° C. in order to ensure saturation of HeLa cell receptors before addition of $^{35}$S-labeled T. vaginalis extract (Alderete and Garza, 1988; Arroyo et al., 1992). After washing the fixed HeLa cells five times with TDSET buffer to eliminate non-specifically bound E. coli proteins, cells were again fixed with 2.5% glutaraldehyde in PBS for 1 h at 4° C. This was done to more accurately determine the extent of competition between recombinant proteins and adhesins. These HeLa cells were then treated with 0.2M glycine in PBS for 1 h at RT. Finally, HeLa cells were incubated with detergent extracts containing $^{35}$S-labeled trichomonad adhesins for 18 h at 4° C. and then washed five times with TDSET buffer. Proteins bound to HeLa cells were eluted by boiling in electrophoresis sample buffer for 3 min, (Arroyo et al., 1992; Lehker et al., 1991) and separated by SDS-PAGE. Gels were stained and prepared for fluorography. Cell lysates of E. coli containing the plasmid without any cDNA inserts were used identically as controls. Finally, the fluorographic patterns of the T. vaginalis adhesins were scanned using the NIH Image 1.55b program in order to quantitate the extent of competition between recombinant proteins and trichomonad adhesins.

N-Terminal Amino Acid Sequencing of Purified Trichomonad AP65 Adhesin

Trichomonad adhesin proteins purified by the ligand assay were subjected to SDS-PAGE. The proteins were electrotransferred to a polyvinylidene difluoride membrane (Immobilon-P; Millipore Corp., Bedford, Mass.). Protein bands were stained with Coomassie Brilliant blue. The AP65 adhesin band was excised. Microsequencing by automated Edman chemistry was performed with an Applied Biosystems model 470-A gas-phase sequencer with an on line 120-A PTH analyzer (UTHSCSA Protein Chemistry Core Facility).

Analysis of recombinant adhesins for proteinase activity

Recombinant E. coli lysates were prepared as above from 1 ml of overnight cultures. E. coli were resuspended in 200 μl of electrophoresis sample buffer (Laemmli, 1970) and heated at 37° C. for 15 min (Neale and Alderete, 1990). Aliquots of 6 μl of recombinant E. coli lysates were subjected to substrate-SDS-PAGE using a 10% separating gel with acrylamide co-polymerized with gelatin (Neale and Alderete, 1990). Following electrophoresis, gels were treated with 2.5% Triton X-100 for 1 h at RT and then soaked in activation buffer (100 mM sodium acetate buffer, pH 4.5 with 1 mM dithiothreitol) for 2 h at 37° C. To visualize the proteinase bands, gels were stained with Coomassie brilliant blue. As controls, T. vaginalis lysates with and without inhibitors of cysteine proteinases (Neale and Alderete, 1990; Arroyo and Alderete, 1989) were always included. Also E. coli with the plasmid but without cDNA inserts was used. Duplicate immunoblots of SDS-PAGE gels of recombinant E. coli were done to insure the presence of adhesins in the gels used for the proteinase assay.

Purification of antibody from recombinant adhesins

Recombinant E. coli colonies bound to NC (Sambrook et al., 1989) were fixed with chloroform and treated with lysis buffer (100 mM Tris-HCl, pH 7.8, 150 mM NaCl, 5 mM MgCl$_2$, 1.5% bovine serum albumin (BSA), 1 μg/ml pancreatic DNase I, 40 μg/ml lysozyme, and 20% fetal bovine serum) for 18 h at RT. Membranes were rinsed with TNT buffer and blocked with BLOTTO containing 1.5% BSA (blocking buffer). Filters containing recombinant proteins were incubated for 18 h at 4° C. with rabbit antiserum generated against T. vaginalis isolate T106. Previous work by the present inventor (Alderete and Garza, 1988) had shown that antibody to adhesins from anti-T. vaginalis serum was present in low-titer and difficult to detect by immunoblot. Nonetheless, enrichment of specific antibody was attempted from rabbit antiserum generated to the isolate from which mRNA was derived for cDNA synthesis. The antiserum was diluted 1:100 in 0.5% Tween 20 in PBS in order to avoid non-specific binding of rabbit antibody. As before, antiserum was adsorbed with E. coli lysate prior to use. After extensive washing of the NC membranes with TNT buffer, specific antibody was eluted by incubation for 5 min with elution buffer (200 mM glycine, 200 mM NaCl and 0.1% BSA, pH 2.8). Eluted antibody was immediately neutralized with 5M NaOH and diluted 1:1 with blocking buffer (Dailey and Alderete, 1991), and used in immunoblot with NC membranes containing T. vaginalis adhesins purified by the ligand assay (Arroyo et al., 1992). Preimmune serum used throughout as a control.

Antibodies

In another aspect, the present invention contemplates an antibody that is immunoreactive with a polypeptide of the invention. An antibody can be a polyclonal or a monoclonal antibody, and is preferably a monoclonal antibody. Means for preparing and characterizing antibodies are well known in the art (See, e.g., Antibodies "A Laboratory Manual, E. Howell and D. Lane, Cold Spring Harbor Laboratory, 1988).

A polyclonal antibody may be prepared by immunizing an animal with an immunogen comprising a polypeptide of the present invention and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

Antibodies, both polyclonal and monoclonal, specific for the adhesin polypeptides of the present invention may be prepared using conventional immunization techniques, as will be generally known to those of skill in the art. A composition containing antigenic epitopes of the adhesin proteins can be used to immunize one or more experimental animals, such as a rabbit or mouse, which will then proceed to produce specific antibodies against the adhesin polypeptide. Polyclonal antisera may be obtained, after allowing time for antibody generation, simply by bleeding the animal and preparing serum samples from the whole blood.

To obtain monoclonal antibodies, one would also initially immunize an experimental animal, often preferably a mouse, with an adhesin polypeptide composition. One would then, after a period of time sufficient to allow antibody generation, obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to the desired adhesin polypeptide.

Following immunization, spleen cells are removed and fused, using a standard fusion protocol (see, e.g., The Cold Spring Harbor Manual for Hybridoma Development, incorporated herein by reference) with plasmacytoma cells to produce hybridomas secreting monoclonal antibodies against the adhesin polypeptides. Hybridomas which produce monoclonal antibodies to the selected antigens are identified using standard techniques, such as ELISA and Western blot methods.

Hybridoma clones can then be cultured in liquid media and the culture supernatants purified to provide the adhesin-specific monoclonal antibodies. It is contemplated that the antibodies may be utilized as discussed herein to distinguish the various members of each adhesin protein family to determine the variation in expression. This information would then be useful in preventing adhesion by blocking adhesion by the antibody binding, or by producing conditions that are non-conducive to Trichomonas adhesion.

Biological Functional Equivalents

Modification and changes may be made in the structure of the encoded polypeptides used in the vectors and DNA segments of the present invention and still obtain a functional molecule that encodes a protein or peptide with desirable characteristics. For example, the adhesin proteins disclosed herein may be designed to have substitutions, deletions or additions in the amino acid sequence through the use of site directed mutagenesis. Alternatively, the nucleic acid sequence may be altered without altering the encoded amino acid sequence. Such alterations in a nucleic acid or amino acid sequence are well known in the art, and such altered sequences with an equivalent biological activity would fall within the scope of the appended claims. The following is a discussion based upon changing the amino acids of a protein to create an equivalent, or even an improved, second-generation molecule. The amino acid changes may be achieved by changing the codons of the DNA sequence, according to the following codon table:

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

For example, certain amino acids may be substituted for other amino acids in a protein structure without appreciable loss of interactive binding capacity with structures such as, for example, binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the adhesin proteins, or corresponding DNA sequences which encode said proteins without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0 ±1); glutamate (+3.0 ±1); serine (+0.3); asparagine (+0.2); glutamine (+0.2); glycine (0); threonine (−0.4); proline (−0.5 ±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Isolation of cDNAs and Recombinant AP65

Successful isolation of recombinant *E. coli* colonies immunoreactive with antisera and mabs to the adhesins (Arroyo et al., 1992) was possible only when mRNA, derived from high-iron-grown parasites (Lehker et al., 1991), was used to generate a cDNA library. Table 2 summarizes the characterization of the cloned recombinant *E. coli* expressing putative adhesins. Three cDNAs (numbered 1 through 3) encoded AP65, one (numbered 4) encoded AP51, and six (numbered 5 through 10) encoded AP33. No colonies were immunoreactive with AP23 antiserum, possibly due to the reported sensitivity of this adhesin to the denaturing conditions of solubilization and blotting (Arroyo et al., 1992).

Plasmid DNAs purified from immunoreactive colonies listed in Table 2 were digested with XmaIII. Single inserts that range from ~500 bp to ~1800 bp were observed after electrophoresis in TAE buffer and EtBr staining of 1% agarose gels. The plasmid vector DNA without insert was digested similarly as a control. Various insert sizes ranging from ~500 base pairs (bp) to ~1800 bp (Table 2) were visualized in ethidium bromide (EtBr)-stained gels. The largest inserts of the AP65 and AP33 clones were of sufficient size to possibly encode full-length adhesins based on known $M_r$s of the proteins (Arroyo et al., 1992). Restriction mapping of the cDNAs was also performed, and the maps of representative cDNAs for AP65 (F11.2) and AP33 (F5.5) with AP51 are illustrated in FIG. 1. The maps show the uniqueness of the cDNAs, indicating at this time that the adhesins are from different genes.

TABLE 2

Characterization of the cDNA clones and recombinant adhesins.

| # cDNA clone[a] (Ab) | cDNA designation | approximate insert size (bp)[b] | $M_r$ (KDa)[c] | over-expression[d] |
|---|---|---|---|---|
| 1 (anti-AP65) | F11.1 | 1200 | 47 | ±[e] |
| 2 (anti-AP65) | F11.2 | 1750 | 63, 51, 47 | − |
| 3 (anti-AP65) | F11.5 | 1700 | 63, 51, 47 | − |
| 4 (anti-AP51) | AP51.2 | 1000 | 38 | + |
| 5 (anti-AP33) | F5.1 | 550 | 21 | + |
| 6 (anti-AP33) | F5.2 | 950 | 40 | + |
| 7 (anti-AP33) | F5.3 | 850 | 38 | + |
| 8 (anti-AP33) | F5.4 | 900 | 36 | + |
| 9 (anti-AP33) | F5.5 | 900 | 42 | + |
| 10 (anti-AP33) | F5.6 | 750 | 32 | + |

[a]The cDNA clones were classified based on the reactivity with monospecific antiserum or monoclonal antibody (Arroyo et al., 1992) to each *T. vaginalis* adhesin.
[b]The insert size in base pairs (bp) was deduced from a standard curve using HindIII-digested λ DNA as molecular weight markers from ethidium bromide-stained agarose gels (McDonnell et al., 1977; Southern, 1979).
[c]Relative molecular weight ($M_r$) of recombinant proteins in kilodaltons (kDa) from electrophoresis in a 10% denaturing polyacrylamide-SDS gels was deduced from a standard curve using high and low molecular weight markers (Bio-Rad Laboratories). Recombinant AP65 proteins that are not over-expressed were immunoblotted for estimation of $M_r$.
[d]The degree of protein expression of the recombinant adhesins was evaluated based on the ability to readily detect protein bands on Coomassie blue-stained polyacrylamide.
[e]Abbreviations: +, over-expression; ±, low expression; −, no visible band of expected size.

EXAMPLE 2

Characterization of Adhesin cDNA Clones
Molecular Sequence Analysis

Figure 2A:
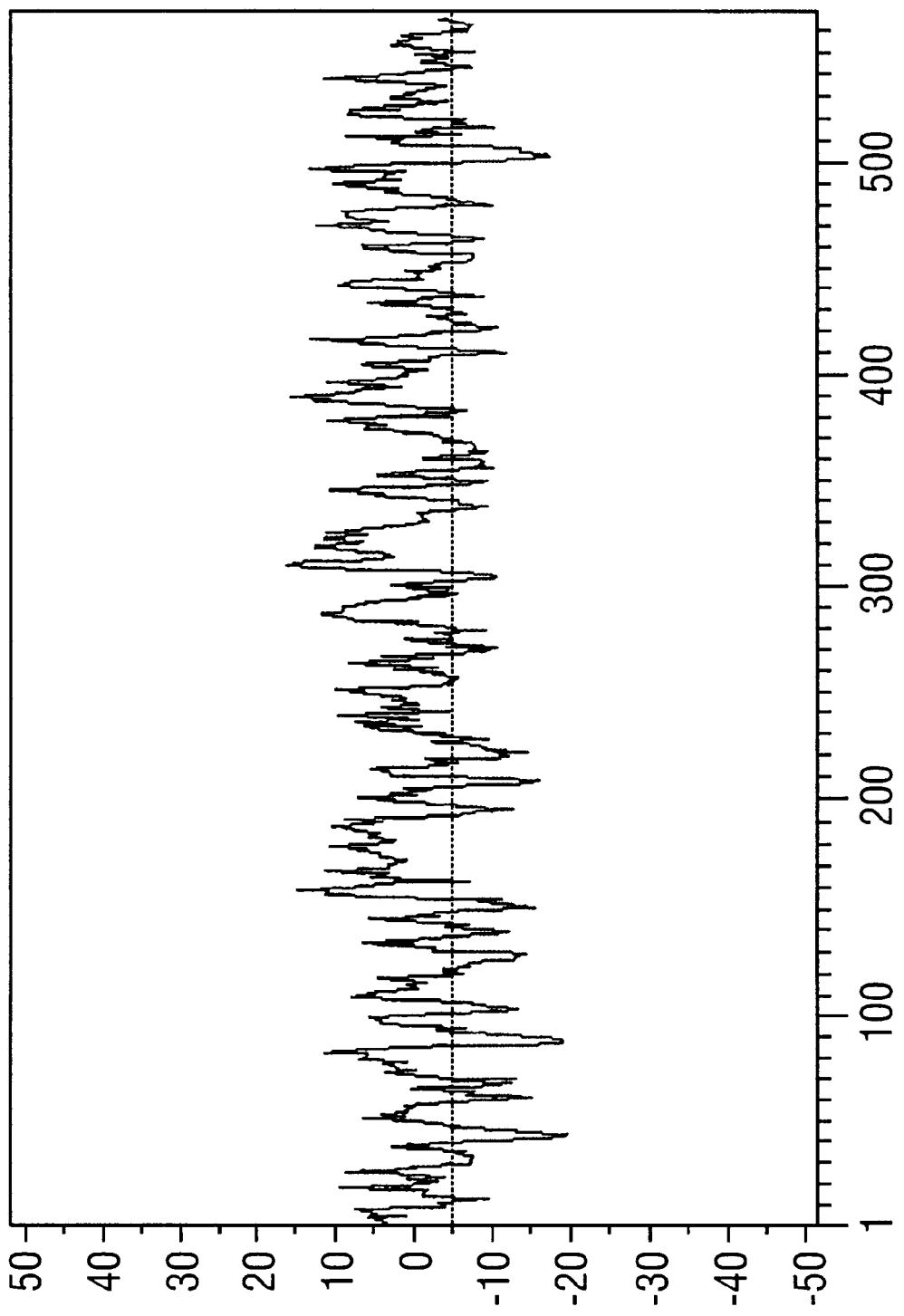
FIG. 2A. Hydropathy plot of the AP65-1 translated protein. Hydropathy and amino acid sequence analysis reveals possible membrane domains. Shading indicates those areas predicted to be associated with the membrane using the methods of Eisenberg et al. (1984), Rao and Argos (1986), and Klein et al. (1985).
Figure 2B:
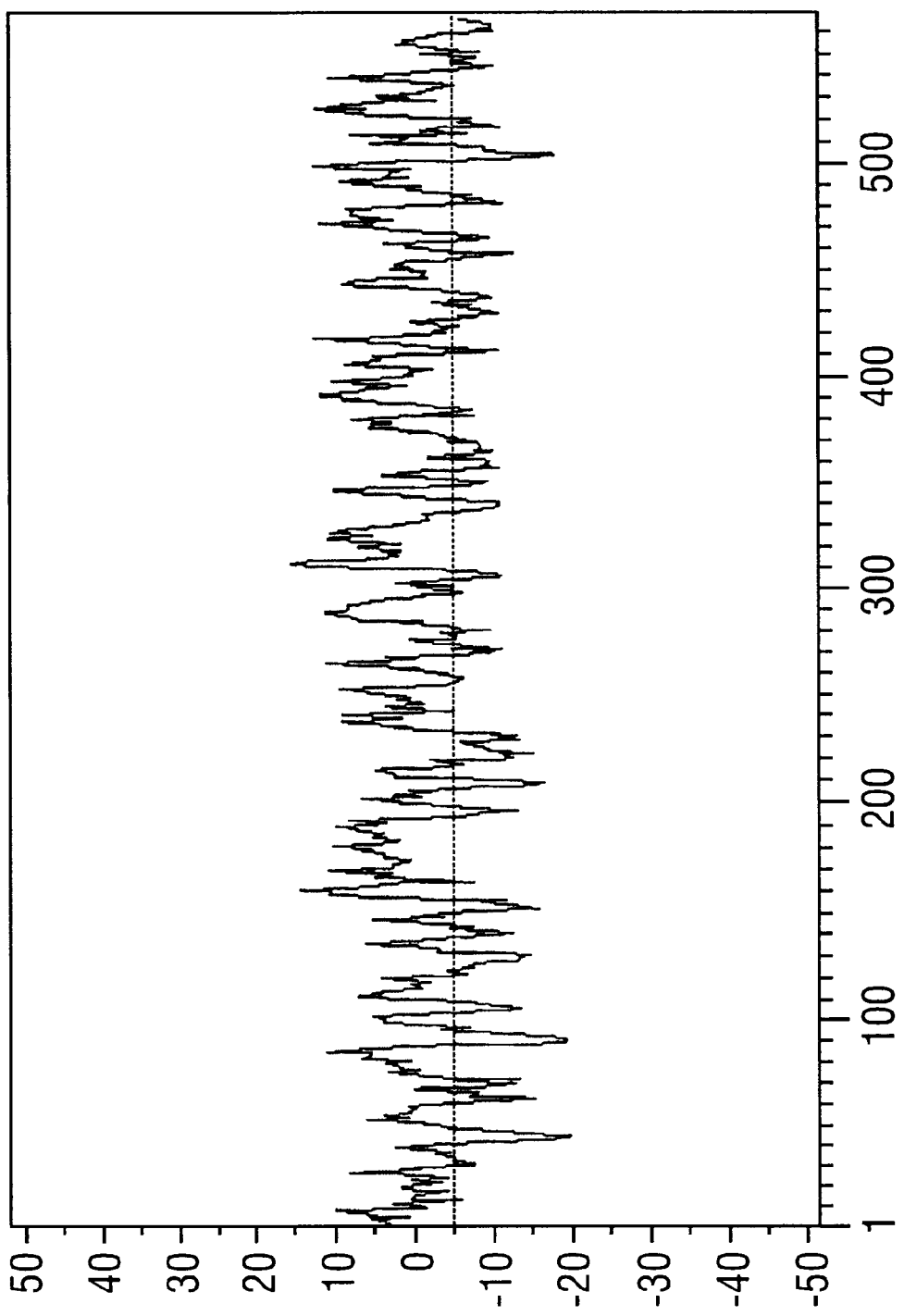
FIG. 2B. Hydropathy plot of the AP65-2 translated protein as in FIG. 2A.
Figure 2C:
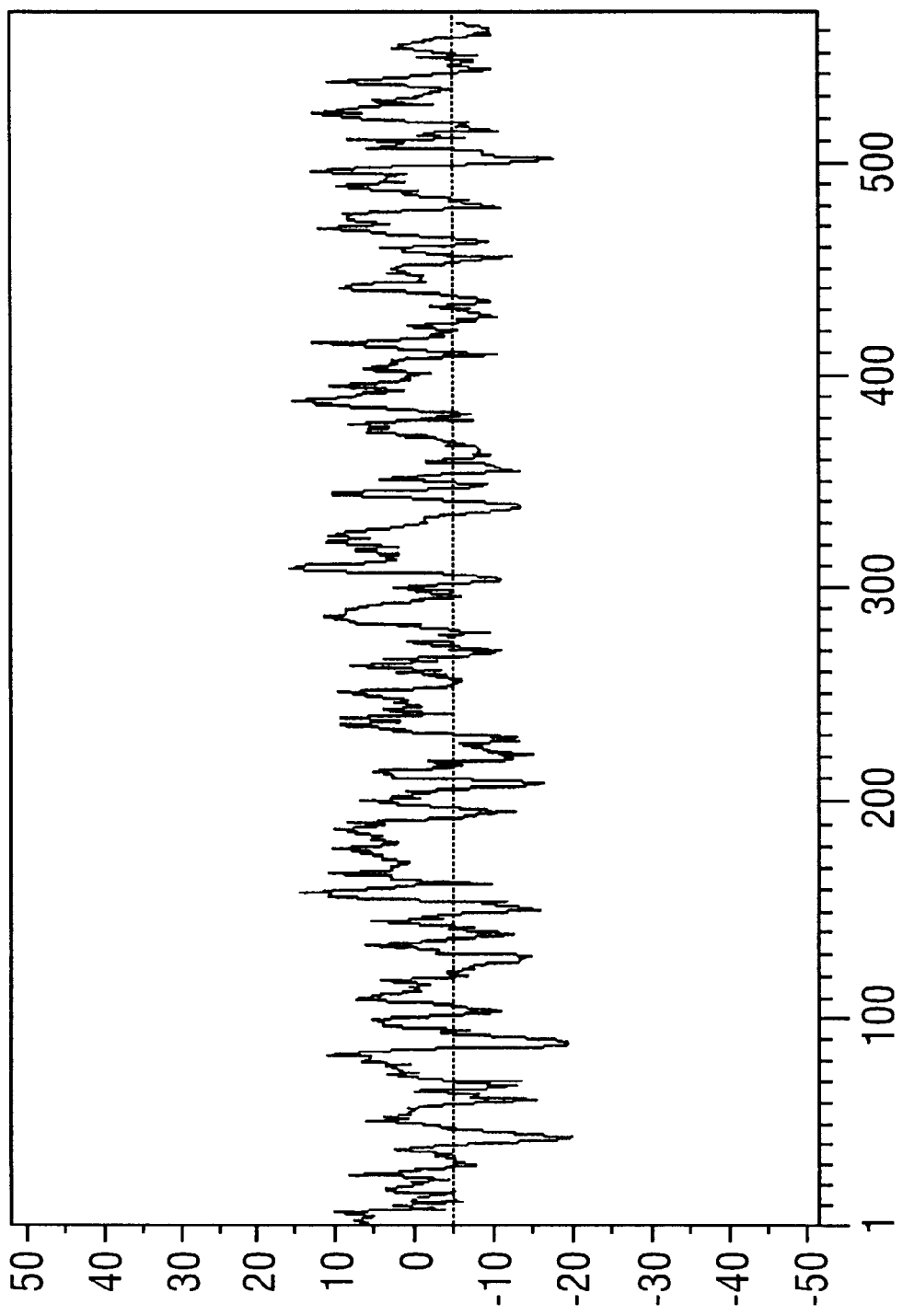
FIG. 2C. Hydropathy plot of the AP65-3 translated protein as in FIG. 2A.

The nucleotide sequences of the complete ap65 genes originally represented by cDNA clones, F11.1, F11.2 and F11.5, as seen in Table 2, are presented in FIG. 2A, FIG. 2B, and FIG. 2C. The size of the complete inserts, derived by using AmpliFINDER on the original cDNAs F11.1, F11.2 and F11.5, were 1766 bp, 1764 bp, and 1804 bp in length, respectively. All sequences contained a 1629 nucleotide open reading frame (ORF) that encoded a protein of 543 amino acids. Sequence analysis showed that the genes were similar but not identical, with 87% identity at the DNA level and 91% identity at the protein level. Neither of the cDNAs were A+T rich; both had an A+T/G+C ratio of approximately 1. The presence of a poly-A tail on the cDNAs indicated that the 3' end of the transcript was complete. The AP65-1 and AP65-2 predicted proteins had pIs of 7.29 and 8.12, respectively.

Restriction Enzyme Analysis

High resolution mapping of the AP65 cDNAs using various endonuclease restriction enzymes showed clear differences, confirming the sequence data. The cDNAs were defined on the basis of cutting and non-cutting restriction enzymes. For example, for F11.2 the cutting enzymes were BamHI, BstXI, SphI and XcmI and for F11.5 the cutting enzymes were BamHI, BstXI, EcoRI and PmaCI. These data and the fact that both cDNAs encoded for immunocrossreactive recombinants indicated that distinct proteins, now called AP65-1 and AP65-2, were encoded by the F11.2 and F11.5 cDNAs, respectively. The same strategy was used to show the distinctness between the F11.1 cDNA with the F11.2 and F11.5 cDNAs encoding the AP65 adhesins.

The restriction maps allowed the demonstration by Southern analysis that HindII, HindIII, PmaCI, SacII and XcmI cleaved internal fragments of either F11.2 or F11.5 cDNAs or of both. Based on these findings, three restriction enzymes (PmaCI, SacII and XcmI), which generated unique-sized internal fragments for F11.2 and F11.5 cDNAs, were chosen. Fragments a (~640 bp) and b (~600 bp) were designated as F11.2-specific, and fragments c (~840 bp) and d (~920 bp) were specific for F11.5. These bands were readily visible due to the molecular size differences and the intensities of hybridization when the distinct cDNA inserts were used as probes. Again, the same approach demonstrated that F11.1 cDNA encoded for a distinct AP65 gene (called ap65-3 encoding for adhesin AP65-3).

Next each of the ap65 genes were confirmed to be present in the genome of *T. vaginalis* as distinct genes present in multiple copies. To first demonstrate this, purified plasmid DNA harboring each cDNA insert was restricted and electrophoresed in agarose. Southern analysis of digested plasmids using $^{32}$P-labeled F11.2 and F11.5 cDNA inserts as probes 1 and probe 2, respectively, revealed all of the expected fragments. Fragments a and b were detected in F11.2 cDNA digested by PmaCI and SacII. Similarly, fragments c and d were detected in F11.5 cDNA digested with SacII and XcmI. The band intensities reflected the recognition of the restricted DNA fragment by the homologous radiolabeled cDNA from which the band was derived.

Southern analysis of restricted genomic DNA also gave the expected four fragments. Fragment a (~640 bp) was present only in the PmaCI digest and showed, as expected, strong homology to F11.2 cDNA (probe 1). Fragment d (~920 bp), detected in the XcmI digest, strongly hybridized to F11.5 cDNA (probe 2), as expected. SacII-digested DNA contained both b (~600 bp) and c (~800 bp) fragments; the first showed strong reactivity to F11.2 cDNA (probe 1) and the second to F11.5 (probe 2), as predicted. In both the plasmid and genomic DNA studies, the hybridization of cDNA probes with large-sized DNA is likely due to hybridization to digested DNA still harboring common cDNA sequences.

Genomic organization of the adhesin genes

Southern analysis of trichomonad genomic DNA treated with restriction endonucleases that did not digest within the cDNAs were performed along with controls. Genomic DNA digested with these and other non-cutting restriction endonucleases always gave multiple bands. In each case, at least two bands were seen for each cDNA used as a probe. Importantly, the same patterns were seen regardless of the AP65 or AP33 cDNAs used.

Southern analysis was also performed on genomic DNA treated with cutting enzymes (EcoRI for F11.2 and PstI and SphI for F11.5) and non-cutting enzymes (BamHI and BstXI for both F11.2 and F11.5), based on the restriction maps. When non-cutting enzymes for F11.2 and F11.5 were employed, hybridization patterns with either $^{32}$P-labeled F11.2 or F11.5 cDNA probes gave multiple bands. As expected, digestion with internal cutting enzymes yielded a greater number of hybridizing bands for the respective probes.

However, since F11.2 and F11.5 cross-hybridized, it became necessary to repeat the studies using probes specific for each cDNA. This was possible using oligonucleotides derived from the 5' regions of each cDNA, which had little homology at the nucleotide sequence level. Two types of PCR products from the 5' region of each gene were generated. Use of the F11.2 primer resulted in 30 new nucleotides and a 142 nucleotide overlap identical with the F11.2 cDNA. Use of the F11.5 primer gave 40 extra bases with a 100 bp overlap with the F11.5 cDNA sequence. A new translational start site was found for both genes.

Each blotted 5'-end PCR product was shown to hybridize only with the corresponding radiolabeled cDNA from which it was derived. In addition, Southern analysis was done with plasmid containing F11.2 or F11.5 digested with HindII or HindIII and probed with radiolabeled 5'-end PCR product. Hybridization of the nick-translated 5'-end products occurred with the plasmid digested with HindII, which retained the 5' of the homologous cDNA reactive with the 5'-end PCR product. The small band detected with each PCR product after HindIII digestion was the expected size of DNA. This small band was derived from the HindIII sites at the multiple cloning site of the plasmid and within each cDNA.

Finally, Southern analysis of the restricted genomic DNA using each of the F11.2 and F11.5 PCR products as probes generated multiple bands. Since BamHI, BstXI, EcoRI and SphI do not cut within the 5'-end PCR products nor digest either F11.2 or F11.5 cDNAs, these data illustrate the likely multiple copy nature of both adhesin genes. The different banding patterns further reaffirmed the distinct nature of the two AP65 genes. The approach just described for the AP65-1 (encoded by F11.2 cDNA) and AP65-2 (encoded by F11.5 cDNA) proteins and corresponding genes were performed similarly for the AP65-3 adhesin (encoded by the F11.1 cDNA).

A Single Transcript For Each Expected Size Of AP65 Genes

The isolation of three different and independent cDNA clones, in addition to the existence of probes from the 5' ends of the genes that only react from the gene from which it was derived, indicated that the three distinct AP65 genes were transcribed. Northern analysis was performed on RNA isolated from trichomonads, and the results showed representative results of transcripts of ~1.8 kb detected in two representative fresh isolates. Radiolabeled F11.5 cDNA or F11.5-specific 5'-end PCR product were used to probe the RNA blots. Detection of the transcript occurred only with total RNA from high-iron-grown trichomonads, as expected (Lehker et al., 1991). Longer exposures of X-ray film did detect basal levels of transcripts in RNA derived from low-iron-grown organisms. Densitometric scanning comparison of the levels of transcripts between high- versus low-iron-grown trichomonads revealed a 30% level of transcription under low-iron conditions when compared to high-iron parasites. Identical results were obtained when using the F11.1 and F11.2 cDNAs as probes as well as when using the highly unique 5'-end products of all adhesin genes as probes, as shown above for the F11.5 cDNA. Examination of numerous other isolates also gave similar results. Quantitation of total purified RNA and ethidium bromide-stained duplicate gels showed identical amounts of total RNA in all lanes.

The different adhesin cDNAs do not cross-hybridize

Southern analysis was done on all of the cDNA clones with the same or different radiolabeled cDNAs as probes. The analysis was performed on blots of restriction endonuclease-digested plasmid cDNA probed with the F11.2, AP51.2 and F5.5 cDNA probes. Approximately 2 μg of recombinant plasmid DNA was digested with XmaIII, electrophoresed on 1% agarose gels, and blotted onto Zeta-probe membranes. Hybridization was performed with nick-translated cDNA probes. The results of these analyses showed that the cDNA clones hybridized only to themselves and the other cDNAs encoding for the same adhesin but not with cDNAs of the other adhesins. None of the $^{32}$P-radiolabeled cDNA inserts hybridized to vector alone, which was handled similarly. These data are consistent with the lack of any immuno-crossreactivity between the recombinant proteins, shown later and consistent with data previously reported (Arroyo et al., 1992).

5' Leader Sequence and Promoter Region

Data indicated that 12 amino acids encoded by the cDNAs were not present on the mature protein, as evidenced by N-terminal amino acid sequencing data of the AP65 adhesin purified from the ligand assay. This suggested that the AP65 protein was synthesized with a leader sequence that was cleaved to form the mature polypeptide. The AP65-1 and AP65-2 N-terminal sequences were similar with 9 of 12 amino acids identical. The AP65 putative signal peptides (amino acids 1–12 of SEQ ID NO:2, AP65-1 and SEQ ID NO:4, AP65-2, were compared to leader sequences from several sources including *T. vaginalis* hydrogenosomal proteins β-succinyl CoA synthetase 53 (β-SCS53) and β-SCS1, (Johnson et al., 1993; Lahti et al., 1992), α-succinyl CoA synthetase 1 (α-SCS1) and α-SCS2 (Lahti et al., 1994), ferredoxin (Fd) (Johnson et al., 1990), and adenylate kinase (AK) (Lange et al., 1994). Cleavage sites were determined by N-terminal sequencing. A comparison of the leader peptides revealed that all of the sequences begin with Met-Leu and have an arginine at the −2 position relative to the cleavage site, consistent with that previously reported (Johnson et al., 1992). Thus, the AP65 leader sequences do not appear characteristic of secretory signal peptides.

The 5' untranslated regions of the AP65 clones were unusually short (nucleotides 1–13 of SEQ ID NO:1, AP65-1 and 1–14 of SEQ ID NO:3, AP65-2). No typical eukaryotic promoter elements, such as the TATA box, were found. However, an examination of the sequence 5' to the start site revealed similarity to the promoter elements of other *T. vaginalis* protein coding genes that have been reported (Quon et al., 1994). Alignment with the 13 bp consensus sequence for *T. vaginalis* promoters TCAYTWYTCATTA, SEQ ID NO:18, showed that between 8 and 10 bases of each AP65 5' adhered to the pattern.

Hydropathy Plots and Sequence Reveals Possible Membrane Domains

Figure 3:
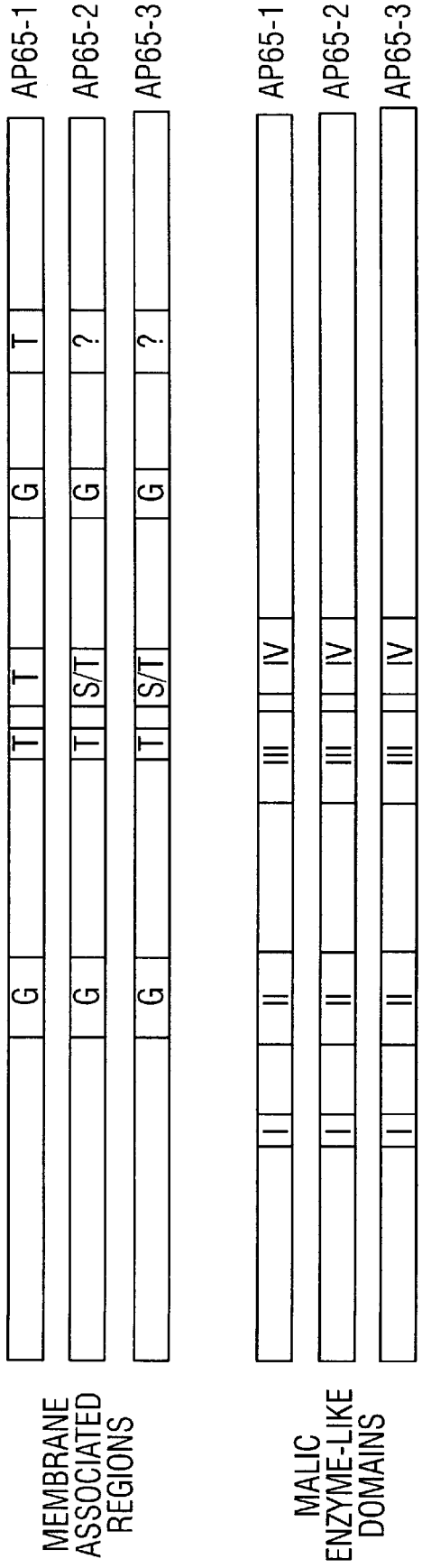
FIG. 3. Positioning of amino acid membrane-spanning domains and malic enzyme-like domains revealed by amino acid sequence analysis. In the top line, predicted membrane-associated areas for each adhesin are indicated. The segments were classified as globular (G), transmembrane (T), and/or surface (S), based on the algorithms used for the hydropathy analysis. In line 2, regions that show strong homology to malic enzyme based on amino acid similarities are indicated. These domains include the NADP-binding region (I), the βαβ-ADP binding fold (II), the malic enzyme manganese-binding site (III), and the NADP βαβ-binding fold (IV).
Figure 4A:
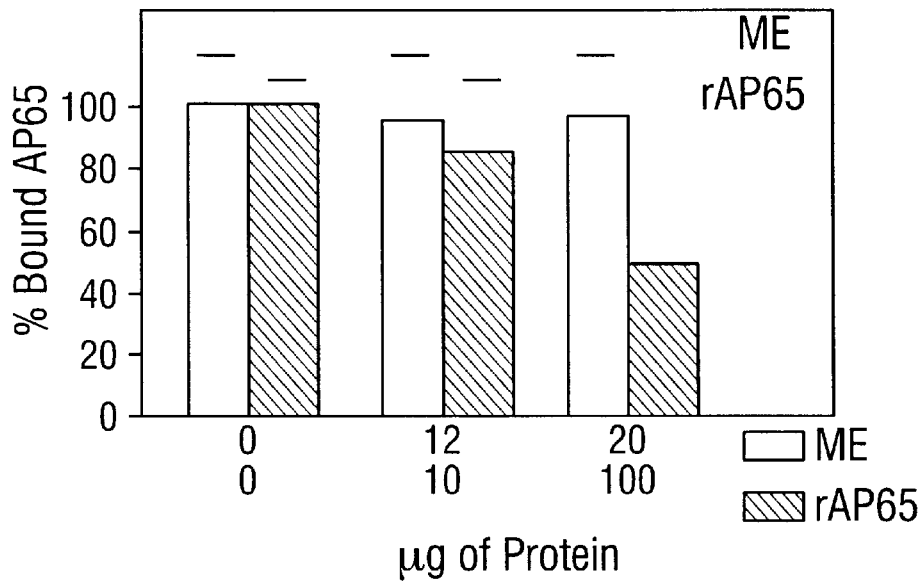
FIG. 4A. Adhesins AP65-1 and AP65-2 express biofunctionality and have receptor-binding epitopes unique from malic enzyme-like sequences. Recombinant AP65 protein, but not malic enzyme, inhibits binding of $^{35}$S-labeled trichomonad AP65 to host cells. Fluorograms of the competition experiment are shown above the bar graph. Trichomonad AP65 from $^{35}$S-labeled *T. vaginalis* extracts were added to fixed HeLa cells in the ligand assay as previously reported (Arroyo et al., 1992), which were first pretreated with either malic enzyme (ME) or extracts of recombinant *E. coli* expressing AP65 from the F11.2 cDNA. Only the recombinant AP65 from *E. coli* extracts competed with $^{35}$S-labeled trichomonad adhesin, as shown in the corresponding densitometry results. Increasing amounts of purified malic enzyme (clear box) did not inhibit the binding of *T. vaginalis* AP65 to HeLa cells. In contrast, the addition of recombinant AP65 (spotted box) inhibited the binding of trichomonad AP65 in a concentration-dependent manner. One hundred micrograms of *E. coli* lysate containing recombinant adhesin (rAP65) decreased parasite AP65 binding to fixed HeLa cells by ~55%.
Figure 4C:
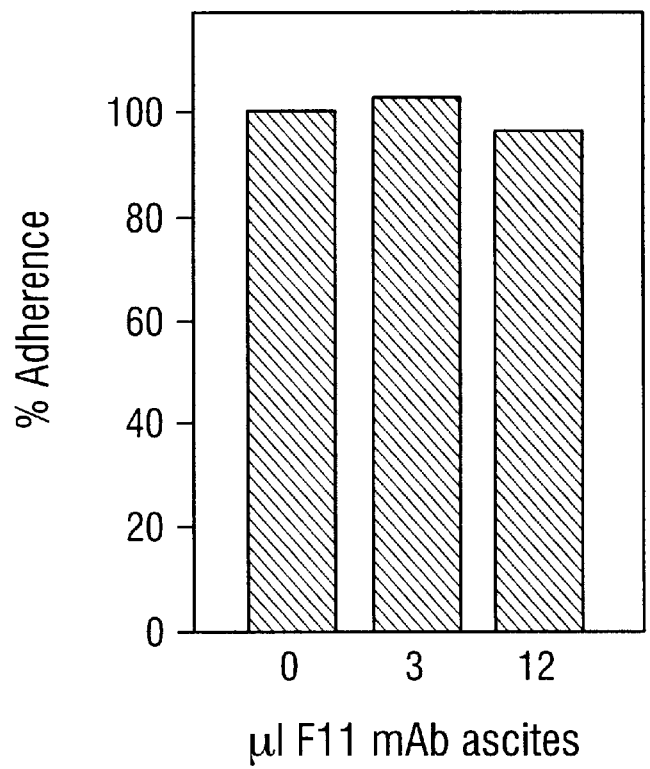
FIG. 4C. The mAb (F11) to AP65 that is immunocrossreactive with malic enzyme does not inhibit cytoadherence of *T. vaginalis* to HeLa cells. Ascites of F11 mAb had a concentration of antibody exceeding 1 mg/ml of specific anti-AP65 IgG antibody.
Figure 4B:
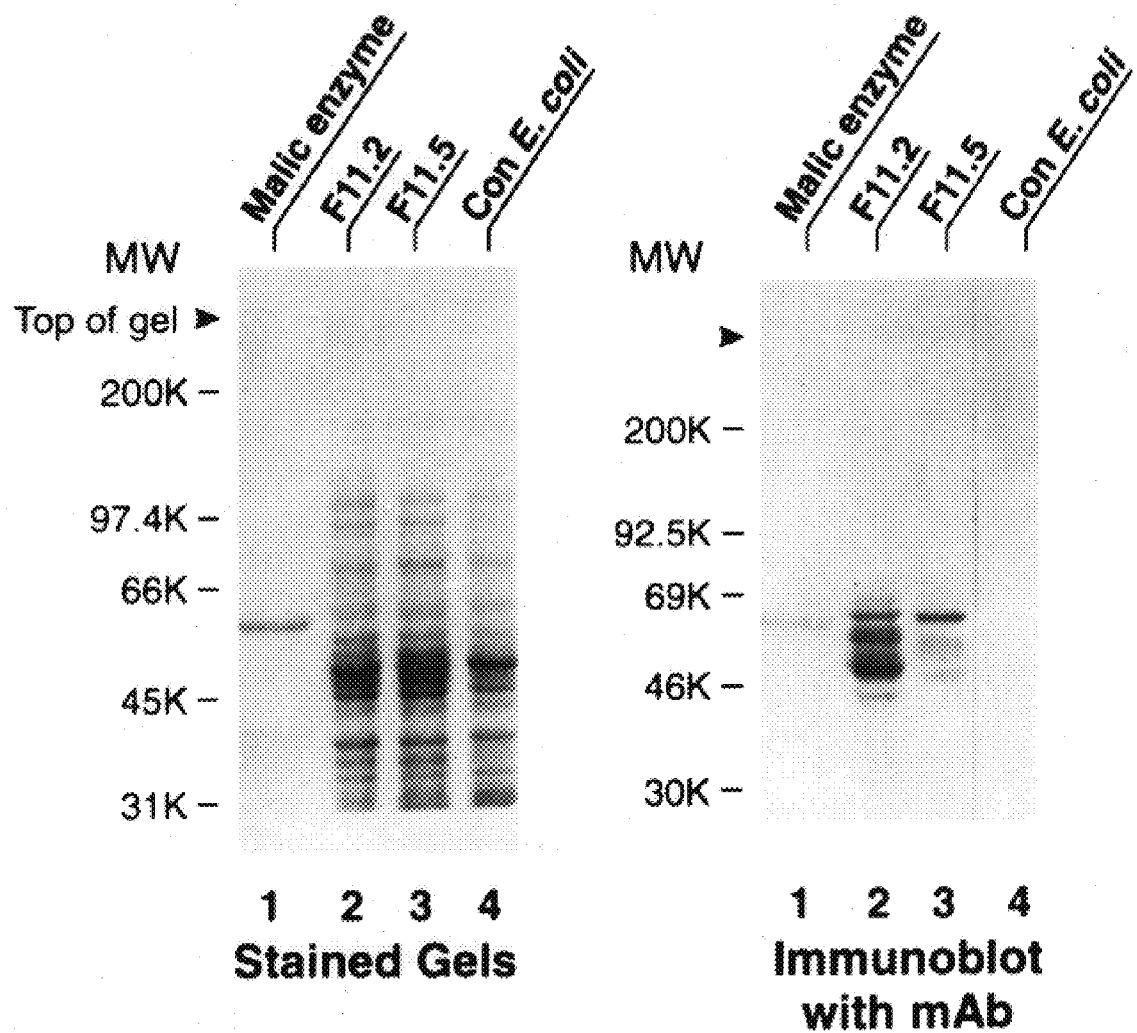
FIG. 4B. Conditions for cytoadherence of isolate T016 were identical to those recently reported (Arroyo et al., 1992b). Levels of inhibition seen with the antiserum to AP65 were similar to those previously reported.

The hydropathy plots (Kyte and Doolittle 1982) of AP65-1, AP65-2 and AP65-3 are very similar with only a few distinctions as shown in FIG. 3A, FIG. 3B and FIG. 3C. Analysis of the plots (See Table 3) revealed 5 regions in AP65-1 that might be associated with the membrane. Of those 5 regions, 4 are present in AP65-2. The existence of possible membrane-associated segments was supported by identification of sequences which vary only slightly between the clones (Table 3). The first two regions were identical in both AP65-1 and AP65-2. The fourth area was classified as globular for both, despite amino acid differences. The variations in the third region, although small, resulted in a different classification for each clone. It is contemplated that these distinctions in sequence and hydropathy correspond to differences in membrane topology. Importantly, the identification of at least one possible membrane-spanning segment in both proteins is consistent with the surface localization of AP65 (Arroyo et al., 1992). Finally, the relative position within the proteins of each membrane-associated domain is shown for each of the AP65 proteins in FIG. 4.

TABLE 3

Membrane Associated Regions of the AP65 Clones

| REGION | cDNA | SEQUENCE (ID NO:) | LOCATION | PREDICTION |
|---|---|---|---|---|
| 1 | F11.2 | ILGLGKLGASGLGIPVGKLML (SEQ ID NO:19) | 166–186 | Globular |
|  | F11.5 | ILGLGDLGASGLGIPVGKLML (SEQ ID NO:20) | 166–186 | Globular |
|  | F11.1 | ILGLGDLGASGLGIPVGKLML (SEQ ID NO:20) | 166–186 | Globular |
| 2 | F11.2 | GTAAVAAATLASAT (SEQ ID NO:21) | 282–295 | Transmembrane |
|  | F11.5 | GTAAVAAATLASAT (SEQ ID NO:21) | 282–295 | Transmembrane |
|  | F11.1 | GTAAVAAATLASAT (SEQ ID NO:21) | 282–295 | Transmembrane |
| 3 | F11.2 | IIFIGAGSAAIGIANLIVDMTV (SEQ ID NO:22) | 308–329 | Transmembrane multimeric |
|  | F11.5 | IIFIGAGSAATGIANLIVDMAV (SEQ ID NO:23) | 308–329 | Surface/Transmembrane |
|  | F11.1 | IIFIGAGSAATGIANLIVDMAV (SEQ ID NO:23) | 308–329 | Surface/Transmembrane |
| 4 | F11.2 | CVIGVSGVPGLITKEIVQATL (SEQ ID NO:24) | 387–407 | Globular |
|  | F11.5 | VIGVSGVPGLITKEIVQAACA (SEQ ID NO:25) | 388–408 | Globular |
|  | F11.1 | VIGVSGVPGLITKEIVQATCA (SEQ ID NO:26) | 388–408 | Globular |

TABLE 3-continued

Membrane Associated Regions of the AP65 Clones

| REGION | cDNA | SEQUENCE (ID NO:) | LOCATION | PREDICTION |
|---|---|---|---|---|
| 5 | F11.2 | VITAQANNSWIFPAVGYALVT (SEQ ID NO:27) | 458–478 | Transmembrane multimeric |
|  | F11.5 | TITAQANNSWIFPAVGYALVT (SEQ ID NO:28) | 458–478 | ? |
|  | F11.1 | TITAQANNSWIFPAVGYALVT (SEQ ID NO:28) | 458–478 | ? |

AP65-1 and AP65-2 Have Malic Enzyme-Like Sequences

A scan of the SWISS-PROT (Release 28) and EMBL (Release 37) databases using the FSTPSCAN and FST-NSCAN programs based on the algorithm of Lipman and Pearson (1985) revealed significant similarity between the AP65 clones and various malic enzymes. When compared to human malic enzyme, for example, each of the AP65 genes and proteins showed ~54% identity at the nucleotide level and 38% identity at the amino acid level, respectively. The homology was limited principally to 4 regions: residues 111 to 119, 163 to 196, 276 to 292, and 312 to 330. The identity in areas homologous to malic enzyme was as high as 78%. In these conserved domains, AP65-1 and AP65-2 were almost identical with only 3 total amino acid differences.

Sequence analysis revealed that 3 of the regions corresponded to the dinucleotide-binding sites found in malic enzymes and other enzymes. The region between amino acids 111 to 119 shows homology to the putative NADP-binding sites of human and murine malic enzyme, goose fatty acid synthetase, and human glyceraldehyde 3-phosphate dehydrogenase. Residue 120 in all AP65 proteins (FIG. 2) is a cysteine amino acid conserved among all malic enzymes; this residue is believed to be the malate-binding site (Satterlee and Hsu, 1991). Since modification of the cysteine impairs binding of L-malate, but not NADPH, the involvement of this region in binding NADP is unlikely (Satterlee and Hsu, 1991). A segment spanning residues 163 to 196 matched a number of elements from the consensus sequence for the ADP-binding βαβ fold (Wierenga et al., 1985). The AP65 sequences contain the essential GXGXXG (SEQ ID NO:29) motif prerequisite for NAD-binding. AP65 also shows homology to the NADP-specific βαβ binding fold (Scrutton et al., 1990). Amino acids 312 to 330 of AP65-1 and AP65-2 include the GXGXXA, SEQ ID NO:30, sequence necessary for the binding of NADP in other proteins. Finally, all but one amino acid from residues 276 to 292 corresponded to the malic enzymes signature sequence, a pattern conserved among all malic enzymes so far investigated. It is noteworthy that the amino acid positions of all these regions are similar for the AP65 clones and the malic enzymes.

Iron-regulated expression of the adhesin genes.

Northern analysis revealed transcripts of approximately 1.8 kb, 1.4 kb, and 0.9 kb for the AP65, AP51 and AP33 adhesins, respectively. These sizes were consistent with that predicted based on $M_r$s of the adhesins purified from the ligand assay, as published earlier. (Arroyo et al., 1992). Bands on autoradiograms were more readily detectable, however, only in total RNA from parasites grown under high-iron conditions, as compared to low-iron conditions, reaffirming earlier work on the transcriptional regulation of expression of the adhesin gene by iron (Lehker et al., 1991). Densitometric scanning revealed six to ten-fold greater levels of transcript under iron-replete versus iron-limiting growth conditions. EtBr-stained agarose gels showed loading of equivalent amounts of total RNA.

In the Northern analysis, a single transcript complementary to the cDNA probe for each member of the three adhesins (AP65, AP51, and AP33). Each cDNA, when used as a probe individually, detected a corresponding transcript of the expected size for the respective adhesin. Northern analysis was performed on 30 μg of total RNA from $T.$ $vaginalis$ isolate T106 grown under iron-replete medium conditions. Identical results were obtained with numerous other fresh isolates as well as when the other cDNAs for the respective recombinant adhesins (Table 2) were used to probe the same or duplicate blots. Longer exposure of X-ray film showed the presence of a basal level of transcript in total RNA of low-iron parasites. EtBr-stained total RNA after electrophoresis in 1% agarose revealed identical amounts of RNA in all lanes, as evidenced by the intensities of the ribosomal RNA bands.

EXAMPLE 3

Recombinant Adhesins Expressed by $E.$ $coli$

Four adhesin proteins purified from the ligand assay were immunoblotted with pooled antiserum to each of the adhesins (Arroyo et al., 1992). The immunoblots showed reactivity with only three of the four adhesins. The absence of antibody detection of AP23 was as previously reported (Arroyo et al., 1992) presumably due to the sensitivity of the adhesin to the denaturing conditions of solubilization and blotting (Arroyo et al., 1992). Stained total protein patterns from recombinant $E.$ $coli$ with cDNAs for AP51 and for AP33 showed readily visible bands, indicating over expression in comparison to control $E.$ $coli$ proteins. In contrast, no similar increase in amounts of protein bands above the control was obtained for recombinant AP65, suggesting a lack of over-expression or a high turnover of the protein encoded by these cDNAs.

Immunoblot analysis was performed with respective antiserum as well as with mAbs to each of the adhesins on total proteins of control and recombinant $E.$ $coli$. Strong reactions were seen for AP51 and each of the recombinant AP33 proteins. This was expected based on the over-expression of the stained proteins. Recombinant AP65, on the other hand, gave an intense band by immunoblot with the expected $M_r$ of the protein for the smaller-sized F11.1 cDNA. A triplet of poorly-reactive proteins, however, was consistently seen for the larger-sized AP65 cDNAs. This was the case under a variety of growth conditions. The multiple bands indicative of degradation of a larger AP65 protein may reflect the reported sensitivity of this adhesin to proteinases (Alderete and Garza, 1988; Arroyo et al., 1992) or that the recombinant may adversely affect $E.$ $coli$.

Proteins of $E.$ $coli$ harboring the vector without any inserts were used as controls in immunoblots and never reacted with anti-adhesin serum. In addition, a pooled preparation of prebleed rabbit serum from each of the antisera failed to detect any recombinant proteins. Finally, antibody to any of the trichomonad adhesins, e.g. AP65, reacted only with the homologous recombinant proteins and not to the heterologous recombinant proteins.

EXAMPLE 4

Biofunctionality of Recombinant Adhesins

Recombinant *E. coli* extracts were incubated with fixed HeLa cells in the ligand assay. Proteins that bound to HeLa cells were eluted and electrophoresed for immunoblotting with specific anti-adhesin antibody. Each of the representative recombinant proteins bound to HeLa cells and was detected by respective anti-adhesin antibody. No similar protein recognition in immunoblots was seen with control, prebleed serum or myeloma culture supernatant. Incubation of cells with extract from control *E. coli* gave no detectable bands in similar studies.

A competition study for binding to HeLa cells was performed with recombinant *E. coli* lysates and $^{35}$S-labeled adhesins of *T.vaginalis*. Pretreatment of HeLa cells with lysates of *E. coli* expressing each recombinant protein decreased the amount of radiolabeled *T. vaginalis* adhesin binding to host cells. Binding of $^{35}$S-labeled trichomonad adhesins was not similarly inhibited when HeLa cells were first treated with control *E. coli* lysate.

The strong homology between the AP65 adhesins and malic enzymes raised questions as to the possible role of malic enzyme activity in *T. vaginalis* cytoadherence. In order to determine whether malic enzyme influenced *T. vaginalis* cytoadherence, it was important to perform a ligand assay with malic enzyme and recombinant AP65 proteins (Arroyo et al., 1992).

Figure 5A:
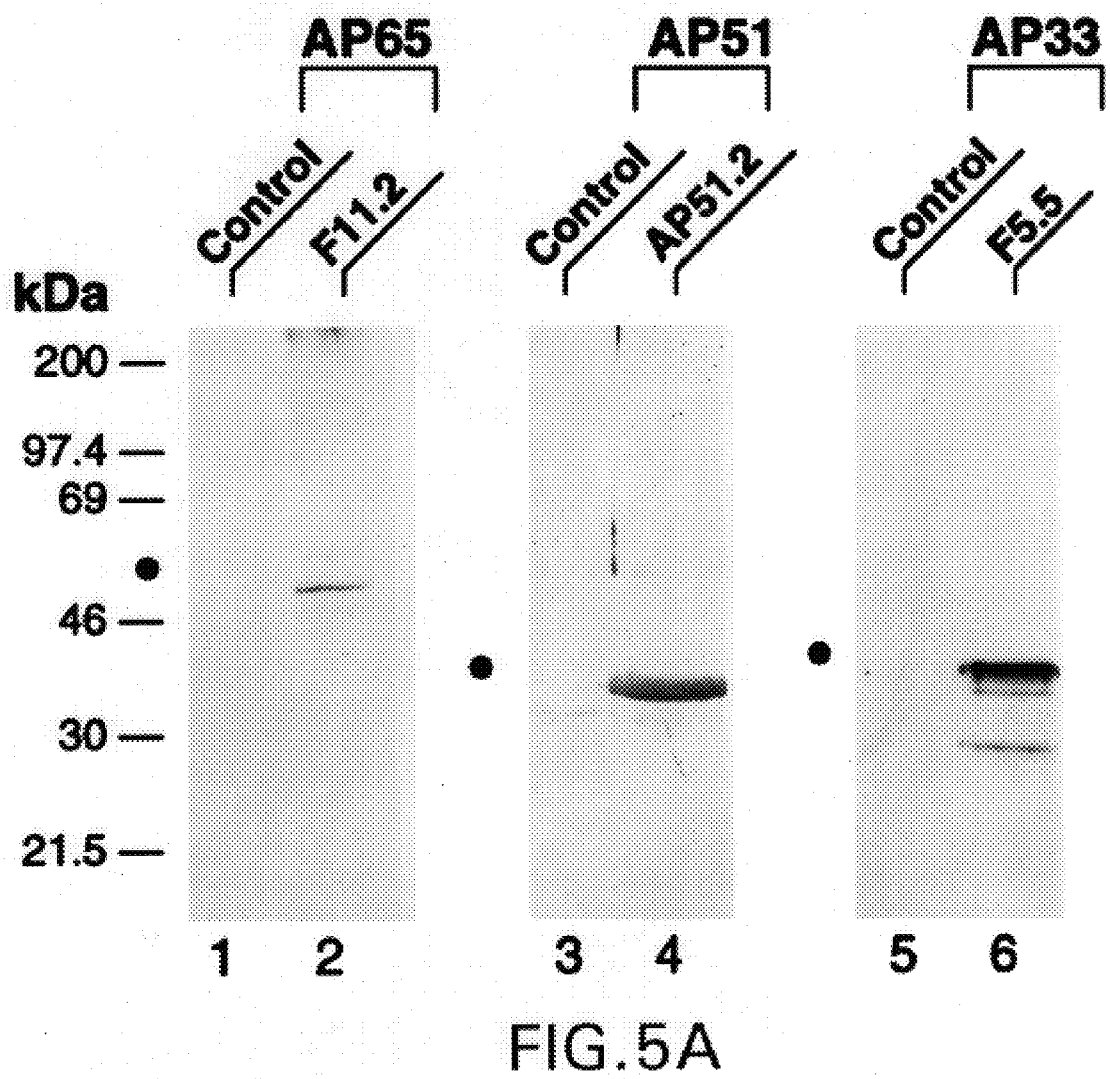
FIG. 5A. Representative studies showing recombinant proteins, AP65, AP51 and AP33 binding to HeLa cells. The recombinant E. coli lysate used for the studies is designated above each lane. Control refers to E. coli harboring the vector without inserts used as a negative control (lanes 1, 3 and 5). Each recombinant protein bound and released from HeLa cell surfaces was electrophoresed and blotted onto nitrocellulose for detection with specific antiserum or mAb. Control prebleed rabbit serum or myeloma culture supernatant failed to detect any of the bound recombinant proteins. Dots designate the major recombinant adhesin bound to fixed HeLa cells. The numbers on the left show the size in kilodaltons (kDa) (×1000) of the prestained Rainbow molecular weight markers (Amersham Corp., Arlington, Ill.).

A competition experiment was performed with recombinant *E. coli* lysates and $^{35}$S-labeled adhesins of *T. vaginalis*. Pretreatment of HeLa cells with lysates of *E. coli* expressing each recombinant protein decreased the amount of radiolabeled *T. vaginalis* adhesin binding to host cells (FIG. 5). Binding of $^{35}$S-labeled trichomonad adhesin was not similarly inhibited when HeLa cells were first treated with the same amounts of protein from control *E. coli* lysate. Similar competition experiments were carried out using increasing amounts of commercially available malic enzyme. No inhibition of $^{35}$S-labeled trichomonad AP65 was evident when excess (up to 120 μg) purified malic enzyme (FIG. 5A) was first used to pretreat cells or in co-incubation experiments. In addition, malic enzyme at high concentrations did not inhibit binding of recombinant AP65s to HeLa cells. Activity of malic enzyme was monitored throughout to insure the conditions did not denature the protein.

Figure 5B:
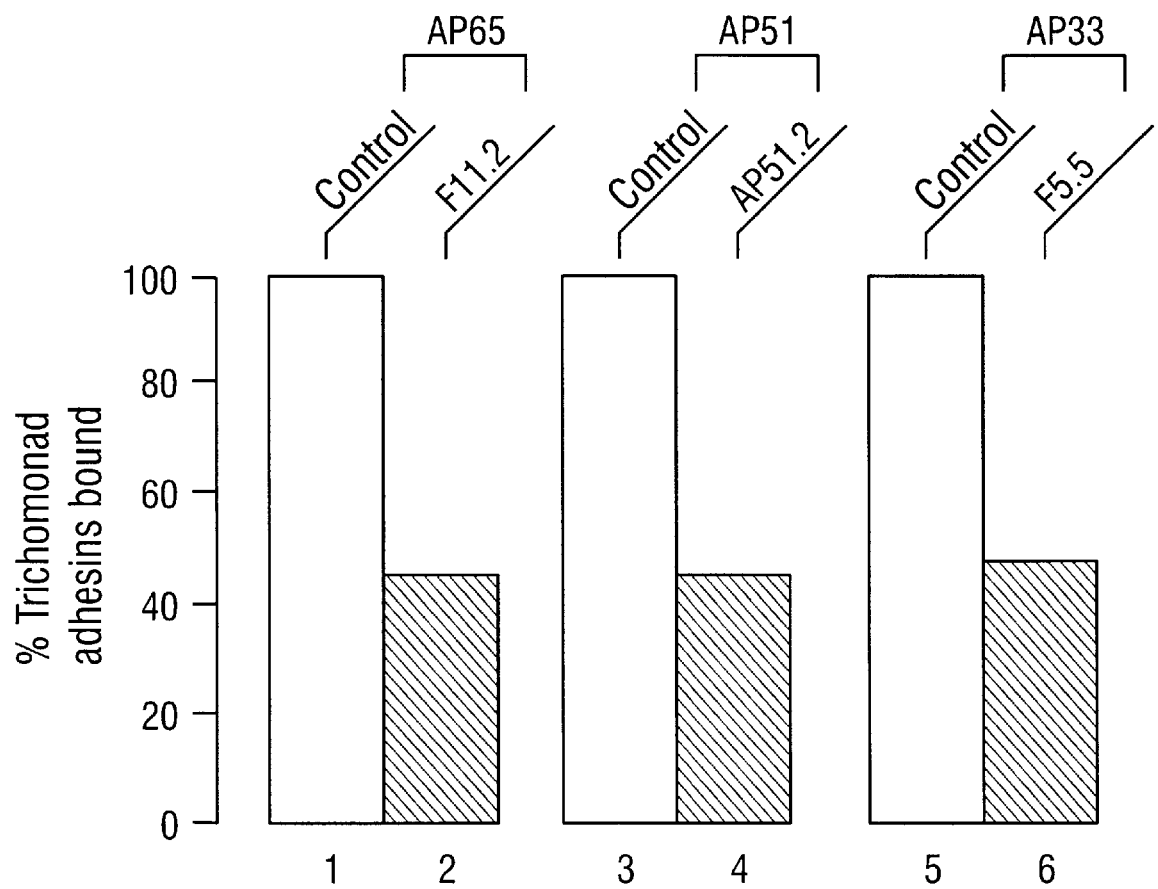
FIG. 5B. Representative studies showing recombinant proteins AP65, AP51 and AP33, competing with $^{35}$S-labeled adhesins in T. vaginalis extract for HeLa cell binding. Fixed HeLa cells were interacted first with recombinant E. coli lysates and then with solubilized radiolabeled trichomonads in a ligand assay as described herein. Densitometric scanning analysis of the resulting fluorogram was used to determine the percentage of $^{35}$S-labeled trichomonad adhesins bound to HeLa cells. The percentage of trichomonad adhesins binding after first interacting HeLa cells with control E. coli lysates represents 100% binding (lanes 1, 3 and 5). This study was repeated three times, and representative results are shown.

A mAb (called F11) previously generated to AP65 purified from the ligand assay (Arroyo et al., 1992) was found to be immuno-crossreactive with malic enzyme. As seen in FIG. 5B, immunoblots with mAb F11 of malic enzyme (lane 1) and recombinant *E. coli* lysates (lanes 2 and 3) revealed recognition of an epitope common between malic enzyme and the adhesins. This same mAb was ineffective at inhibiting *T. vaginalis* organisms attaching to HeLa cells in monolayer cultures (FIG. 5, part C2). In contrast, monospecific rabbit antiserum to AP65 blocked cytoadherence to levels achieved before (FIG. 5, part C1) (Arroyo et al., 1992).

Finally, commercially purchased malic enzyme was used in a competition experiment in a cytoadherence assay (Arroyo et al., 1992). No decrease in levels of trichomonal attachment to HeLa cells was ever observed when pure malic enzyme, or other serum proteins such as albumin were used as controls (Arroyo et al., 1992), was added to the coincubation medium in excess amounts. Only the addition of IgG derived from rabbit anti-AP65 serum (Arroyo et al., 1992) readily inhibited adherence, as shown before.

Figure 6A:
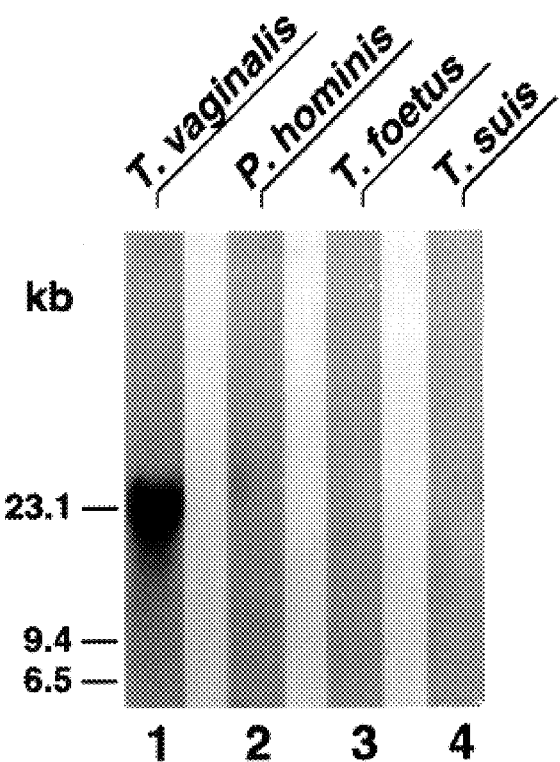
FIG. 6A. Cross-hybridization using cDNA inserts of AP65 adhesins show no cross-reactivity with other trichomonal species.
Figure 6B:
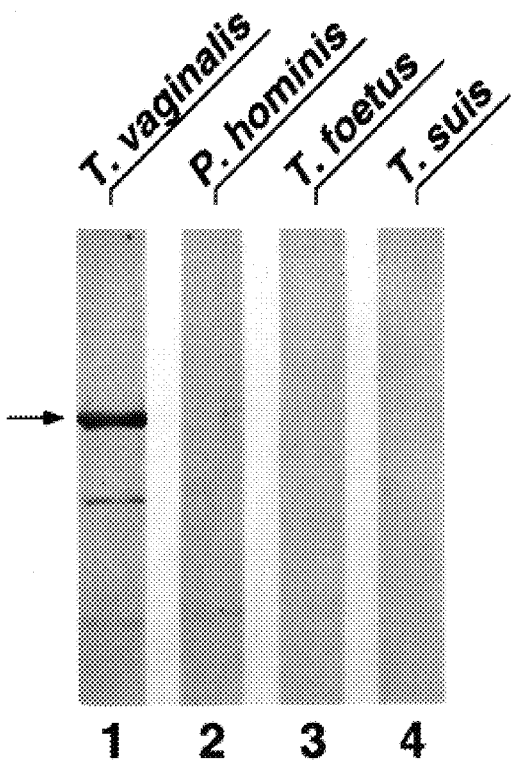
FIG. 6B. A ligand assay was performed with the cDNAs as in FIG. 6A. Again, no cross-reactivity with other trichomonad species is shown.

A similar competition-type experiment was conducted using the recombinant proteins for the other adhesins, i.e. AP51 and the six AP33 recombinant proteins. As shown in FIG. 6A, the other two adhesins also bound to fixed Hela cells. Pretreatment of the HeLa cells with the recombinant proteins (for AP33, represented by cDNA clone F5.5) resulted in inhibition in the binding of the corresponding $^{35}$S-labeled trichomonad adhesins (FIG. 6B).

Furthermore, antibody from rabbit anti-*T. vaginalis* serum (Arroyo et al., 1992) that bound to representative recombinant *E. coli* colonies was recovered. Immunoblots of ligand-purified *T. vaginalis* adhesins were detected with the eluted antibody (Arroyo et al., 1992). These studies, therefore, show that the respective recombinant proteins and purified adhesins are immuno-crossreactive. Furthermore, the recombinant proteins encode for cell-binding domains recognized by the same host receptor as the adhesins (Arroyo et al., 1992).

Recombinant proteins show no proteolytic activity

Because cysteine proteinase activity is required for cytoadherence (Arroyo and Alderete, 1989), it was contemplated by the inventors that the recombinant adhesin proteins may possess proteinase activity. This activity is expected to be detectable by substrate gel electrophoresis using gelatin, as previously done for analysis of cysteine proteinases (Neale and Alderete, 1990). Neither the *E. coli* lysates of recombinant proteins nor the trichomonad adhesins purified by the ligand assay (Arroyo et al., 1992) had such proteinase activity (Neale and Alderete, 1990). As a control, trichomonal lysate was electrophoresed simultaneously during the assay in a separate well and, upon activation, the expected numerous proteinase activities were readily detected. Under these conditions, the adhesins possessed no detectable proteinase activity.

EXAMPLE 5

Isolation of AP23 cDNA

Even though no *E. coli* colonies were detected that were immunoreactive with the AP23 antisera in previous attempts, this method is expected to prove successful in detecting the AP23 adhesin protein(s) under blotting conditions. The present inventors have previously reported on the relative inability of anti-AP232 antiserum to detect AP23 in immunoblots, however, the combination of enhancing the blot reaction and the availability of new antisera has allowed for recognition of AP23 under denaturing conditions. It is expected therefore, that immunoreactive clones from the cDNA library will be detected.

An alternative method may be employed is the ligand assay disclosed herein. Utilizing the ligand assay, sufficient quantities of purified AP23 adhesins will be available for N-terminal sequencing. The proteins will be electrotransferred to a polyvinylidene difluoride membrane (Immobilon-P; Millipore Corp., Bedford, Mass.). Protein bands will be stained with Coomassie Brilliant blue. The AP23 adhesin band will be excised. Microsequencing by automated Edman chemistry will be performed with an Applied Biosystems model 470-A gas-phase sequencer with an on line 120-A PTH analyzer.

Because the nucleotide-codon usage has been established for *T. vaginalis*, N-terminal amino acid sequence will allow for synthesis of oligonucleotides, which in turn can be used as probes for screening the cDNA library. This will be done using standard protocols. Reactive clones will be purified and examined as described for the other cDNAs and recombinant proteins in the previous examples.

EXAMPLE 6

Isolation of Genomic Adhesin Genes
Generation of a genomic library of *T. vaginalis*

Cloning of the genomic copy of each adhesin will be the first step in identifying gene structure, including possible introns, promoter elements, and other regulatory sequences. It will also allow for the comparisons on the structure of the adhesin genes among different isolates, i.e. in Type I (virus-negative) and Type II (virus-positive) isolates; for the determination of the number of copies; and for generating information about the plasticity of the genome of this ancient eukaryote. It is contemplated that two genomic libraries may be constructed from agar-cloned Type I and Type II isolates.

The availability of a genomic copy encoding for all or parts of the adhesin gene repertoire(s), which includes AP65-1, AP65-2, AP65-3, AP51, AP33-1, AP33-2 and AP33-3 and those of the AP23 adhesin(s) will allow the mapping of the location of the individual adhesin genes relative to one another in the trichomonal genome. The *T. vaginalis* genomic library may preferably be constructed in the λ phage replacement vector Lambda GEM™-11 (Promega Corp., Madison, Wis.). This vector is preferred because of the presence of the rare-cutting restriction enzyme recognition sequence of SfiI and the flanking T7 and Sp6 promoter sites. The SfiI sites would allow in most cases excision of large inserts (10–20 kb) as single fragments. The flanking promoters would allow for generation of in vitro-transcribed products, which can then be used as probes in chromosome walking. High-purity trichomonad DNA will be extracted using established procedures. Purified DNA may be digested with Sau3A and fragments of 10–20 kb may be purified from agarose gels using agarase enzyme (New England Biolabs). The sized DNA may be filled in with Klenow and co-precipitated with λ phage vector that has been digested with XhoI, partially filled in with Klenow and dephosphorylated. Various vector to insert ratios may be used. Ligated DNA may then be packaged (GigaGold, Strategene). Phage may be propagated on the permissive, rec⁻ host strain KW251. Background with this system has been reported to be 100 pfu/μg with recombinant efficiency of 7×10⁶ pfu/μg, eliminating the need for spi selection and allowing the use of a rec⁻ host strain.

The quality of the library may be evaluated by screening duplicate lifts with an actin hybridization probe. As another control, recombinant λ phage harboring the phenotypically variable protein (P270) gene, which will be known to exist in the genomic library, may be identified by plaque hybridization to existing DNA. Reactive plaques may be purified through several rounds until all plaques are reactive on duplicate lifts. The insert(s) may be subjected to high resolution restriction mapping.

In cases where the original clone does not contain the entire gene, overlapping clones will be isolated using in vitro transcripts from the T7 and Sp6 promoter as hybridization probes. Purified λ phage DNA may be digested with restriction enzymes that cut within a 1 kb region downstream of the transcription promoters. The radiolabeled probe may be used to isolate λ phage inserts extending upstream or downstream of the original insert. It is anticipated that up to 10 kb extending from the 5' and 3' end of the repeat element might be needed to clone the entire structural gene. Larger regions of the genome may need to be cloned in the event of the presence of large intervening sequences.

EXAMPLE 7

Inhibition of *Trichomonas vaginalis* Adherence

The blocking of *Trichomonas vaginalis* cytoadhesion by the recombinant adhesion proteins that are an embodiment of the present invention demonstrates the utility of the nucleic acid and amino acid molecules disclosed herein as therapeutic or prophylactic agents in Trichomonas infection. For example, recombinant adhesin proteins or peptides may be formulated into a creme, lotion or douche for the prevention of Trichomonas adhesion. The preparation of cremes, lotions and douches containing the adhesin proteins or peptides will be generally known to those of skill in the art. For example, the preparation of vaginal suppositories and cremes is described in Remington's Pharmaceutical Sciences, Mack Publishing Company, Easton, Pa., 18th Edition, 1990, pages 1609–1614 (incorporated herein by reference). The adhesins may also be administered in conjunction with standard drug therapy such as administration of Metronidazole.

The polypeptides to be administered may preferably comprise the entire amino acid sequence of one or more of the adhesin proteins disclosed herein as SEQ ID NO:2, SEQ ID NO:4, SEQ ID NO:6, SEQ ID NO:8, SEQ ID NO:10, SEQ ID NO:12 or SEQ ID NO:14, or they may be a portion of said sequences. Particularly preferred will be those sequences identified as relatively hydrophilic as determined by the method of Kyte and Doolittle, such as SEQ ID NO:23, for example (See FIG. 3A, FIG. 3B, FIG. 3C, and Table 3).

The adhesin polypeptides may be used by administering in an amount that is effective in a preventative manner. In this sense, an "effective preventative amount" means an amount of composition that contains an amount of a Trichomonas adhesin polypeptide sufficient to significantly inhibit or prevent *Trichomonas vaginalis* adhesion to cells in an uninfected subject or to prevent propagation of an active infection.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Alderete, J. F., Newton, E., Dennis, C., Engbring, J., and Neale, K. A. (1991) Vaginal antibody of patients with trichomoniasis is to a prominent surface immunogen of *Trichomonas vaginalis*. Genitourin Med 67: 220–225.

Alderete, J. F., Demes, P., Gombosova, A., Valent, M., Janoska, A., Fabusova, M., Kasmala, L., Garza, G. E., and Metcalfe, E. C. (1988) Phenotypes and protein/epitope phenotypic variation among fresh isolates of *Trichomonas vaginalis*. *Infect Immun* 55: 1037–1041.

Alderete et al., "Specific parasitism of purified vaginal epithelial cells by *Trichomonas vaginalis*," *Infect. Immun.*, 56: 2558–2562, 1988.

Alderete and Garza, "Identification and properties of *Trichomonas vaginalis* proteins involved in cytoadherence," *Infect. Immun.* 56: 28–33, 1988.

Alderete, J. F., Suprun-Brown, L., and Kasmala, L. (1986a) Monoclonal antibody to a major surface glycoprotein immunogen differentiates isolates and subpopulations of *Trichomonas vaginalis*. *Infect Immun* 52: 70–75.

Alderete, J. F., Kasmala, L., Metcalfe, E., and Garza, G. E. (1986b) Phenotypic variation and diversity among *Trichomonas vaginalis* isolates and correlation of phenotype with trichomonal virulence determinants. *Infect Immun* 53: 285–293.

Alderete and Garza, "Specific nature of *Trichomonas vaginalis* parasitism of host cell surfaces," *Infect. Immun.*, 50: 701–708, 1985.

Arroyo et al., "Signalling of *Trichomonas vaginalis* for amoeboid transformation and adhesin synthesis follows cytoadherence," *Mol. Microbiol.*, 7: 299–309, 1993.

Arroyo, R., Engbring J., and Alderete, J. F. (1992) Molecular basis of host epithelial cell recognition by *Trichomonas vaginalis*. *Mol Microbiol* 6: 853–862.

Arroyo, R., and Alderete, J. F. (1989) *Trichomonas vaginalis* proteinase activity is necessary for parasite cytoadherence. *Infect Immun* 57: 2991–2997.

Ausubel, F. M., Brent, R., Kingston, R. E., Moore, D. D., Seidman, J. G., Smith, J. A., and Struhl, K. (1991) Current Protocols in Molecular Biology. Current Protocols (Greene & Wiley). Harvard Medical School.

Buttle, D. J., Ritonja, A., Pearl, L. H., Turk, V., and Barrett, A. J. (1990) Selective cleavage of glycyl bonds by papaya proteinase IV. *FEBS* 260: 15–197.

Camara, M., Boulnois, G. J., Andrew, P. W., and Mitchell, T. J. (1994) A neuraminidase from *Streptococcus pneumoniae* has the features of a surface protein. *Infect Immun* 62: 3688–3695.

Chomczynski, P., and Sacchi, N. (1987) Single-step method of RNA isolation by acid guanidinium thiocyanate-phenol-chloroform extraction. *Anal Biochem* 162: 156–159.

Dailey and Alderete, "The phenotypically variable surface protein of *Trichomonas vaginalis* has a single, tandemly repeated immunodominant epitope," *Infect. Immun.*, 59: 2083–2088, 1991.

Damian, R. T. (1989) Molecular mimicry: parasite evasion and host defense. *Current Topics in Microbiol and Immunol* 145: 101–115.

Diamond, L. S. (1957) The establishment of various trichomonads of animals and man in axenic cultures. *J Parasitol* 43: 488–490.

Eisenberg, D., Schwarz, E., Komavomy, M., and Wall, R. (1984) Analysis of membrane and surface protein sequences with the hydrophobic moment plot. *J. Molec. Biol.* 179: 125–142.

Goudot-Crozel, V., Caillol, D., Djabali, M., and Dessein, A. J. (1989) The major parasite surface antigen associated with human resistance to schistosomiasis is a 37-kD glyceraldehyde-3P-dehydrogenase. *J Exp Med* 170: 2065–2080.

Harlow, E. Da Lane. (1988) Antibodies: A laboratory manual. Cold Spring Harbor Laboratory Press. Cold Spring Harbor, N.Y.

Huitorel, P., and Pantaloni, D. (1985) Bundling of microtubules by glyceraldehyde-3-phosphate dehydrogenase and its modulation by ATP. *Eur J Biochem* 150: 265–269.

Joe, A., Murray, C. S., and McBride, B. C. (1994) Nucleotide sequence of a *Porphyromonas gingivalis* gene encoding a surface-associated glutamate dehydrogenase and construction of a glutamate dehydrogenase-deficient isogenic mutant. *Infect Immun* 62: 1358–1368.

Johnson, P. J., Lahti, C. J., and Bradley, P. J. (1993) Biogenesis of the hydrogenosome: An unusual organelle found in the anaerobic protist, *Trichomonas vaginalis*. *J Parasitol* 79: 664–670.

Johnson, P. J., d'Oliveira, C. E., Gorrel, T.E., and Müller, M. (1990) Molecular analysis of the hydrogenosomal ferredoxin of the anaerobic protist, *Trichomonas vaginalis*. *Proc Natl Acad Sci USA* 87: 6097–6101.

Katiyar, S. S. and Porter, J. W. (1983) Fatty acid synthetase, malic enzyme and other $NADP^+$ binding dehydrogenases have similar antigenic determinant(s) at the NADPH binding domain. *Biochem and Biophys Res Com* 112: 1007–1012.

Kawamoto, R. M., and Caswell, A. H. (1986) Autophosphorylation of glyceraldehydephosphate dehydrogenase and phophorylation of protein from skeletal muscle microsomes. *Biochemistry* 25: 656–661.

Kendrick, A., and Ratlege, C. (1992) Desaturation of polyunsaturated fatty acids in *Mucor circinelloides* and the involvement of a novel membrane-bound malic enzyme. *Eur J Biochem* 209: 667–673.

Khoshnan and Alderete, "Multiple double-stranded RNA segments are associated with virus particles infecting *Trichomonas vaginalis*," *J. Virol.*, 67: 6950–6955, 1993.

Khoshnan, A., and Alderete, J. F. (1993) *Trichomonas vaginalis* with a double-stranded RNA virus has upregulated levels of phenotypically variable immunogen mRNA. *J Virol* 68: 4035–4038.

Klein, P., Kanchisa, M., and DeLisi, C. (1985) The detection and classification of membrane-spanning proteins. *Biochim Biophys Acta* 815: 468–476.

Kyte, J., and Doolittle, R. F. (1982) Simple method for displaying the hydropathy character of a protein. *J Mol Biol* 157: 105–132.

Laemmli, "Cleavage of structural proteins during the assembly of the head of bacteriophage $T_4$," *Nature*, 227: 680–685, 1970.

Lahti, C.J., d'Oliveira, C. E., and Johnson, P. J. (1992) Beta-succinyl Coenzyme A synthetase from *Trichomonas vaginalis* is a soluble hydrogenosomal protein with an amino terminal sequence that resembles mitochondrial presequences. *J Bacteriol* 174: 6822–6830.

Länge, S., Rozario, C., and Müller, M. (1994) Primary structure of the hydrogensomal adenylate kinase of *Trichomonas vaginalis* and its phylogenetic relationships. *Mol Biochem Parasitol* 66: 297–308.

Lehker, M. W., Arroyo, R., and Alderete, J. F. (1991) The regulation by iron of the synthesis of adhesins and cytoadherence levels in the protozoan *Trichomonas vaginalis*. *J Exp Med* 174: 311–318.

Lehker, M. W., and J. F. Alderete (1992) Iron regulates growth of *Trichomonas vaginalis* and the expression of immunogenic proteins. *Mol Microbiol* 6: 123–132.

Lipman, D. J., and Pearson, W. R. (1985) Rapid and sensitive protein similarity searches. *Science* 227: 1435–1441.

Loeber, G., Infante, A. A., Maurer-Fogy, I., Krystek, E., and Dworkin, M. B. (1991) Human $NAD^+$-dependent mitochondrial malic enzyme. *J Biol Chem* 266: 3016–3021.

Lottenberg, R., Broder, C. C., Boyle, M. D. P., Kain, S. J., Schroeder, B. L., and Curtis, R., III. (1992) Cloning, sequence analysis, and expression in *Escherichia coli* of a streptococcal plasmin receptor. *J Bacteriol* 174: 5204–5210.

Mallinson, D. J.,. Lockwood, B. C., Coombs, G. H., and North, M. J. (1994) Identification and molecular cloning of four cysteine proteinase genes from the pathogenic protozoon *Trichomonas vaginalis*. *Microbiol* 140: 2725–2735.

Markos, A., Miretsky, A., and Müller, M. (1993) A glyceraldehyde-3-phosphate dehydrogenase with eubacterial feature in the amitochondriate eukaryote, *Trichomonas vaginalis*. *J Mol Evol* 37: 631–643.

McDonell, M. W., Simon, M. N., and Studier, F. W. (1977) Analysis of restriction fragments of T7 DNA and determination of molecular weights by electrophoresis in neutral and alkaline gels. *J Mol Biol* 110: 119–146.

Meyer-Siegler, K., Mauro, D. J., Seal, G., Wurzer, J., DeRiel, J. K., and Sirover, M. M. (1991) A human nuclear uracil DNA glycosylase is the 37-kDa subunit of glyceraldehyde-3-phosphate dehydrogenase. *Proc Natl Acad Sci USA* 88: 8460–8464.

Miles, L. A., Dahlberg, C. M., Plescia, J., Felez, J., Kato, K., and Plow, E. F. (1991) Role of cell-surface lysines in plasminogen binding to cells: identification of α-enolase as a candidate plasminogen receptor. *Biochemistry* 30: 1682–1691.

Mohana Rao, J. K., and Argos, P. (1986) A conformational preference parameter to predict helices in integral membrane proteins. *Biochim Biophys Acta* 869: 197–214.

Neale, K. A., and Alderete, J. F. (1990) Analysis of the proteinases of representative *Trichomonas vaginalis* isolates. *Infect Immun* 58: 157–162.

Pancholi, V., and Fischetti, V. A. (1993) Glyceraldehyde-3-phosphate dehydrogenase on the surface of group A streptococci is also on ADP-ribosylating enzyme. *Proc Natl Acad Sci USA* 90: 8154–8158.

Pancholi, V., and Fischetti, V. A. (1992) A major surface protein on group A streptococci is a glyceraldehyde-3-phosphate-dehydrogenase with multiple binding activity. *J Exp Med* 176: 415–426.

Piatigorsky, J., and Wistow, G. J. (1989) Enzyme/crystallins: gene sharing as an evolutionary strategy. *Cell* 57: 197–199.

Quon, D. V. K., Delgadillo, M. G., Khachi, A., Smale, S. T., and Johnson, P. J. (1994) Similarity between a ubiquitous promoter element in an ancient eukaryote and mammalian initiator elements. *Proc Natl Acad Sci USA* 91: 4579–4583.

Rubino, S., Muresu, R., Rappelli, P., Fiori, P. L., Rizzu, P., Erre, G. and Cappuccinelli, P. (1991) Molecular Probe for Identification of *Trichomonas vaginalis* DNA, *Journal of Clinical Microbiology* 29: 702–706.

Sambrook et al., "Molecular Cloning: a laboratory manual," Cold Spring Harbor Laboratory Press. Cold Spring Harbor, N.Y. 1989.

Satterlee, J., and Hsu, R. Y. (1991) Duck liver malic enzyme: sequence of a tryptic peptide containing one cysteine residue labeled by the substrate analog bromopyruvate. *Biochim Biophys Acta* 1079: 247–252.

Southern, "Gel electrophoresis of restriction fragments," *Meth. Enzymd.* 68: 152–177, 1979.

Struhl. (1991) Current Protocols in Molecular Biology. Current Protocols (Greene & Wiley). Harvard Medical School.

Towbin, H., Staehelin, T., and Gordon, J. (1979) Electrophoretic transfer of proteins from polyacrylamide gels to nitrocellulose sheets: procedure and some applications. *Proc Natl Acad Sci. USA.* 76: 4350–4354.

Vacca-Smith, A. M., Jones, C. A., Levine, M. J., and Stinson, M. W. (1994) Glucosyltransferase mediates adhesion of *Streptococcus gordonii* to human endothelial cells in vitro. *Infect Immun* 62: 2187–2194.

von Heijne, G., Steppuhn, J., and Herrmann, R. G. (1989) Domain structure of mitochondrial and chloroplast targeting peptides. *Eur J Biochem* 180: 535–545.

von Heijne, G. (1986) *Nucleic Acids Res* 14: 4683–4690.

Wagner, R. W., Matteucci, M. D., Lewis, J. G., Gutierrez, A. J., Moulds, C. and Froehler, B. C. 1993, *Science*, 260, 1510–1513.

Wang, A., and Wang, C. C. (1986) The double-stranded RNA in *Trichomonas vaginalis* may originate from virus-like particles. *Proc Natl Acad Sci USA* 83: 7956–7960.

Wang, A. L., Wang, C. C., Alderete, J. F. (1987) *Trichomonas vaginalis* phenotypic variation occurs only among trichomonad infected with the double-stranded RNA virus. *J Exp Med* 166: 142–150.

Wierenga, R. K., De Maeyer, M. C. H., and Hol, W. G. J. (1985) Interaction of pyrophosphate moities with α-helixes in dinucleotide-binding proteins. *Biochemistry* 24: 1346–1357.

Wistow, G. (1993) Lens crystallins: gene recruitment and evolutionary dynamism. *Trends Biochem Sci* 18: 301–306.

Wistow, G. and Piatigorsky, J. (1987) Recruitment of enzymes as lens structural proteins. *Science* 236: 1554–1555.

Wood, W. I., Gitschier, J., Lasky, L. A. and Lawn, R. M. (1985) Base composition-independent hybridization in tetramethylammonium chloride: A method for oligonucleotide screening of highly complex gene libraries, *Proc. Natl. Acad. Sci. USA,* 82: 1585–1588.

Zhou, C., Yang, Y., and Jong, A. Y. (1990) Mini-Prep in Ten Minutes. *Biotechniques* 8: 172–173.

What is claimed is:

1. An isolated nucleic acid segment encoding a *Trichomonas vaginalis* adhesin protein, and wherein said isolated nucleic acid segment hybridizes under a high stringency condition comprising hybridzing in a solution comprising 50% formamide, 120 mM sodium diphosphate, 250 mM sodium chloride, 7% sodium dodecyl sulfate and 1 mM EDTA at 42° C. to a nucleic acid segment having the sequence or the complement of SEQ ID NO:1, SEQ ID NO:3, SEQ ID NO:5, SEQ ID NO:7, SEQ ID NO:9, SEQ ID NO:11 or SEQ ID NO:13.

2. The nucleic acid segment of claim 1, wherein said *Trichomonas vaginalis* adhesin protein has an amino acid sequence in accordance with SEQ ID NO:2, SEQ ID NO:4 or SEQ ID NO:6.

3. The nucleic acid segment of claim 2, wherein said nucleic acid segment comprises the sequence of SEQ ID NO:1, SEQ ID NO:3 or SEQ ID NO:5.

4. The nucleic acid segment of claim 2, wherein said nucleic acid segment has the sequence of SEQ ID NO:1, SEQ ID NO:3 or SEQ ID NO:5.

5. The nucleic acid segment of claim 1, wherein said adhesin protein has an amino acid sequence in accordance with SEQ ID NO:8, SEQ ID NO:10, SEQ ID NO:12 or SEQ ID NO:14.

6. The nucleic acid segment of claim 5, wherein said nucleic acid segment comprises a nucleic acid sequence in accordance with SEQ ID NO:7, SEQ ID NO:9, SEQ ID NO:11 or SEQ ID NO:13.

7. The nucleic acid segment of claim 6, wherein said nucleic acid segment has a nucleic acid sequence in accordance with SEQ ID NO:7, SEQ ID NO:9, SEQ ID NO:11 or SEQ ID NO:13.

8. An isolated nucleic acid segment comprising a sequence region that consists of at least a 14 nucleotide long contiguous sequence that has the same sequence as, or is complementary to, a 14 nucleotide long contiguous sequence of positions 1–1754 of SEQ ID NO:1, positions 1–1739 of SEQ ID NO:3, positions 1–1745 of SEQ ID NO:5, positions 1–927 of SEQ ID NO:9, positions 1–936 of SEQ ID NO:11 or positions 1–919 of SEQ ID NO:13.

9. The nucleic acid segment of claim 8, further defined as comprising a sequence region that consists of at least a 17 nucleotide long contiguous sequence that has the same sequence as, or is complementary to, a 17 nucleotide long contiguous sequence of positions 1–1754 of SEQ ID NO:1, positions 1–1739 of SEQ ID NO:3, positions 1–1745 of SEQ ID NO:5, positions 1–927 of SEQ ID NO:9, positions 1–936 of SEQ ID NO:11 or positions 1–919 of SEQ ID NO:13.

10. The nucleic acid segment of claim 9, further defined as comprising a sequence region that consists of at least a 20 nucleotide long contiguous sequence that has the same sequence as, or is complementary to, a 20 nucleotide long contiguous sequence of positions 1–1754 of SEQ ID NO:1, positions 1–1739 of SEQ ID NO:3, positions 1–1745 of SEQ ID NO:5, positions 1–927 of SEQ ID NO:9, positions 1–936 of SEQ ID NO:11 or positions 1–919 of SEQ ID NO:13.

11. The nucleic acid segment of claim 10, further defined as comprising a sequence region that consists of at least a 30 nucleotide long contiguous sequence that has the same sequence as, or is complementary to, a 30 nucleotide long contiguous sequence of positions 1–1754 of SEQ ID NO:1, positions 1–1739 of SEQ ID NO:3, positions 1–1745 of SEQ ID NO:5, positions 1–927 of SEQ ID NO:9, positions 1–936 of SEQ ID NO:11 or positions 1–919 of SEQ ID NO:13.

12. The nucleic acid segment of claim 11, further defined as comprising a sequence region that consists of at least a 50 nucleotide long contiguous sequence that has the same sequence as, or is complementary to, a 50 nucleotide long contiguous sequence of positions 1–1754 of SEQ ID NO:1, positions 1–1739 of SEQ ID NO:3, positions 1–1745 of SEQ ID NO:5, positions 1–927 of SEQ ID NO:9, positions 1–936 of SEQ ID NO:11 or positions 1–919 of SEQ ID NO:13.

13. The nucleic acid segment of claim 12, further defined as comprising a sequence region that consists of at least a 75 nucleotide long contiguous sequence that has the same sequence as, or is complementary to, a 75 nucleotide long contiguous sequence of SEQ ID NO:1, SEQ ID NO:3, SEQ ID NO:5, SEQ ID NO:7, SEQ ID NO:9, SEQ ID NO:11 or SEQ ID NO:13.

14. The nucleic acid segment of claim 13, further defined as comprising a sequence region that consists of at least a 100 nucleotide long contiguous sequence that has the same sequence as, or is complementary to, a 100 nucleotide long contiguous sequence of SEQ ID NO:1, SEQ ID NO:3, SEQ ID NO:5, SEQ ID NO:7, SEQ ID NO:9, SEQ ID NO:11 or SEQ ID NO:13.

15. The nucleic acid segment of claim 14, further defined as comprising a sequence region that consists of at least a 200 nucleotide long contiguous sequence that has the same sequence as, or is complementary to, a 200 nucleotide long contiguous sequence of SEQ ID NO:1, SEQ ID NO:3, SEQ ID NO:5, SEQ ID NO:7, SEQ ID NO:9, SEQ ID NO:11 or SEQ ID NO:13.

16. The nucleic acid segment of claim 15, further defined as comprising a sequence region that consists of at least a 300 nucleotide long contiguous sequence that has the same sequence as, or is complementary to, a 300 nucleotide long contiguous sequence of SEQ ID NO:1, SEQ ID NO:3, SEQ ID NO:5, SEQ ID NO:7, SEQ ID NO:9, SEQ ID NO:11 or SEQ ID NO:13.

17. The nucleic acid segment of claim 16, further defined as comprising a sequence region that consists of at least a 500 nucleotide long contiguous sequence that has the same sequence as, or is complementary to, a 500 nucleotide long contiguous sequence of SEQ ID NO:1, SEQ ID NO:3, SEQ ID NO:5, SEQ ID NO:7, SEQ ID NO:9, SEQ ID NO:11 or SEQ ID NO:13.

18. The nucleic acid segment of claim 17, further defined as comprising a sequence region that consists of at least a 700 nucleotide long contiguous sequence that has the same sequence as, or is complementary to, a 700 nucleotide long contiguous sequence of SEQ ID NO:1, SEQ ID NO:3, SEQ ID NO:5, SEQ ID NO:7, SEQ ID NO:9, SEQ ID NO:11 or SEQ ID NO:13.

19. The nucleic acid segment of claim 18, further defined as comprising a sequence region that consists of at least a 947 nucleotide long contiguous sequence that has the same sequence as, or is complementary to, a 947 nucleotide long contiguous sequence of SEQ ID NO:1, SEQ ID NO:3, SEQ ID NO:5, SEQ ID NO:7, SEQ ID NO:9, SEQ ID NO:11 or SEQ ID NO:13.

20. The nucleic acid segment of claim 9, further defined as comprising a sequence region that consists of at least a 974 nucleotide long contiguous sequence that has the same sequence as, or is complementary to, a 974 nucleotide long contiguous sequence of SEQ ID NO:1, SEQ ID NO:3, SEQ ID NO:5, SEQ ID NO:7, SEQ ID NO:9, or SEQ ID NO:13.

21. The nucleic acid segment of claim 20, further defined as comprising a sequence region that consists of at least a 976 nucleotide long contiguous sequence that has the same sequence as, or is complementary to, a 976 nucleotide long contiguous sequence of SEQ ID NO:1, SEQ ID NO:3, SEQ ID NO:5, SEQ ID NO:7 or SEQ ID NO:9.

22. The nucleic acid segment of claim 21, further defined as comprising a sequence region that consists of at least a 1319 nucleotide long contiguous sequence that has the same sequence as, or is complementary to, a 1319 nucleotide long contiguous sequence of SEQ ID NO:1, SEQ ID NO:3, SEQ ID NO:5 or SEQ ID NO:7.

23. The nucleic acid segment of claim 22, further defined as comprising a sequence region that consists of at least a 1764 nucleotide long contiguous sequence that has the same sequence as, or is complementary to, a 1764 nucleotide long contiguous sequence of SEQ ID NO:1, SEQ ID NO:3 or SEQ ID NO:5.

24. The nucleic acid segment of claim 23, further defined as comprising a sequence region that consists of at least a 1766 nucleotide long contiguous sequence that has the same sequence as, or is complementary to, a 1766 nucleotide long contiguous sequence of SEQ ID NO:1 or SEQ ID NO:5.

25. The nucleic acid segment of claim 24, further defined as comprising a sequence region that consists of at least a 1804 nucleotide long contiguous sequence that has the same sequence as, or is complementary to, a 1804 nucleotide long contiguous sequence of SEQ ID NO:5.

26. The nucleic acid segment of claim 1 positioned under the control of a promoter.

27. The nucleic acid segment of claim 26, wherein said promoter is a recombinant promoter.

28. The nucleic acid segment of claim 26, wherein said promoter is up-regulated by iron.

29. The nucleic acid segment of claim 1 further defined as a DNA segment.

30. The nucleic acid segment of claim 8, further defined as a DNA segment.

31. A vector comprising the nucleic acid segment of claim 1.

32. The vector of claim 31, further defined as an expression vector capable of expressing an adhesin peptide or polypeptide in a host cell.

33. A host cell comprising the nucleic acid segment of claim 1.

34. The host cell of claim 33, further defined as an *E. coli* cell.

35. A nucleic acid segment comprising an iron up-regulated promoter and, further defined as comprising nucleotides 1–13 of SEQ ID NO:1, nucleotides 1–14 of SEQ ID NO:3 or nucleotides 1–13 of SEQ ID NO:5.

36. A method of expressing a gene wherein transcription is increased by the presence of iron, comprising the steps of:
 (a) operatively linking said gene to the promoter of claim 35; and
 (b) expressing said gene in the presence of an amount of iron sufficient to increase said transcription.

37. The method of claim 36, wherein said iron is about 250 μM ferrous ammonium sulfate.

38. A method of producing a *Trichomonas vaginalis* adhesin protein comprising the steps of:
 (a) obtaining a nucleic acid segment of claim 1, operatively linked to a promoter;
 (b) transfecting said nucleic acid segment into a host cell; and
 (c) culturing said host cell under conditions effective to produce said *Trichomonas vaginalis* adhesin protein.

39. The method of claim 38, wherein said host cell is an *E. coli* cell.

40. The method of claim 38, further comprising the step of isolating said protein.

41. The nucleic acid segment of claim 12, further defined as comprising a sequence region that consists of at least a 52 nucleotide long contiguous sequence that has the same sequence as, or is complementary to, a 52 nucleotide long contiguous sequence of positions 1-1754 of SEQ ID NO:1, positions 1-1739 of SEQ ID NO:3, positions 1-1745 of SEQ ID NO:5, positions 1-1258 of SEQ ID NO:7, positions 1-927 of SEQ ID NO:9, positions 1-936 of SEQ ID NO:11 or positions 1-919 of SEQ ID NO:13.

\* \* \* \* \*

UNITED STATES PATENT AND TRADEMARK OFFICE
CERTIFICATE OF CORRECTION

PATENT NO.    :   5,922,563
DATED         :   July 13, 1999
INVENTOR(S)   :   John F. Alderete It is certified that error appears in the above-identified patent and that said Letters Patent is hereby corrected as shown below:

In claim 1, column 85, line 19, after 'C', delete --.-- .
In claim 20, column 87, line 10, delete '9', and insert --19-- therefor.

Signed and Sealed this

Fourth Day of January, 2000

Attest:

Attesting Officer            *Acting Commissioner of Patents and Trademarks*